United States Patent
Luan et al.

(10) Patent No.: US 9,387,348 B2
(45) Date of Patent: Jul. 12, 2016

(54) SYSTEM AND METHODS OF PHOTON-BASED RADIOTHERAPY AND RADIOSURGERY DELIVERY

(71) Applicants: Shuang Luan, Albuquerque, NM (US); Lijun Ma, Foster City, CA (US); Zhe Chen, Los Alamos, NM (US)

(72) Inventors: Shuang Luan, Albuquerque, NM (US); Lijun Ma, Foster City, CA (US); Zhe Chen, Los Alamos, NM (US)

(73) Assignee: STC.UNM, Albuquerque, NM (US)

( * ) Notice: Subject to any disclaimer, the term of this patent is extended or adjusted under 35 U.S.C. 154(b) by 225 days.

(21) Appl. No.: 14/293,621

(22) Filed: Jun. 2, 2014

(65) Prior Publication Data

US 2014/0341352 A1 Nov. 20, 2014

Related U.S. Application Data

(63) Continuation of application No. 13/322,327, filed as application No. PCT/US2010/050850 on Sep. 30, 2010.

(60) Provisional application No. 61/277,792, filed on Sep. 30, 2009, provisional application No. 61/365,175, filed on Jul. 16, 2010, provisional application No. 61/365,449, filed on Jul. 19, 2010.

(51) Int. Cl.
*A61N 5/00* (2006.01)
*A61N 5/10* (2006.01)

(52) U.S. Cl.
CPC ............... *A61N 5/1071* (2013.01); *A61N 5/10* (2013.01); *A61N 5/1065* (2013.01); *A61N 5/1081* (2013.01); *A61N 2005/1074* (2013.01)

(58) Field of Classification Search
CPC ..... A61N 5/1071; A61N 5/10; A61N 5/1065; A61N 5/1081; A61N 2005/1074
See application file for complete search history.

(56) References Cited

U.S. PATENT DOCUMENTS

2005/0276377 A1 12/2005 Carol

FOREIGN PATENT DOCUMENTS

WO 2008130634 A1 10/2008

OTHER PUBLICATIONS

Luan et al., "Dynamic gamma knife radiosurgery", Jan. 18, 2009, Phys. Med. Biol. 54 (2009) 1579-1591.
X.Hu et al., "A new Gamma Knife® radiosurgery paradigm: Tomosurgery", Medical Physics, vol. 34, No. 5, May 2007, pp. 1743-1758.

*Primary Examiner* — David J Makiya
*Assistant Examiner* — Dani Fox
(74) *Attorney, Agent, or Firm* — Valauskas Corder LLC

(57) ABSTRACT

Photon-based radiosurgery is widely used for treating local and regional tumors. The key to improving the quality of radiosurgery is to increase the dose falloff rate from high dose regions inside the tumor to low dose regions of nearby healthy tissues and structures. Dynamic photon painting (DPP) further increases dose falloff rate by treating a target by moving a beam source along a dynamic trajectory, where the speed, direction and even dose rate of the beam source change constantly during irradiation. DPP creates dose gradient that rivals proton Bragg Peak and outperforms Gamma Knife® radiosurgery.

13 Claims, 59 Drawing Sheets

SYSTEM AND METHODS OF PHOTON-BASED RADIOTHERAPY AND RADIOSURGERY DELIVERY

STATEMENT CONCERNING FEDERALLY SPONSORED RESEARCH

This invention was made with government support under NSF CBET-0755054. The government has certain rights in the invention.

FIELD OF THE INVENTION

The present invention relates to photon-based radiosurgery and more specifically to dynamic photon painting. The present invention provides for using a dynamically changing radiation beam (such as speed, direction, and/or dose) to irradiate a target thereby significantly increasing a radiation dose falloff rate.

BACKGROUND OF THE INVENTION

Radiosurgery is a non-invasive medical procedure for various kinds of tumors and one of the most effective means for treating local and regional targets such as brain tumors. Instead of a surgical incision, radiosurgery delivers a high dose of high energy photons in radiated beams to destroy the tumor. Radiosurgery is a very efficient method for treating cancers and avoids loss in quality of life compared to other more invasive methods such as surgery or chemotherapy. Since radiated high energy photons can also damage normal cells that are irradiated as the beam passes through a patient to irradiate a tumor, the key of a good radiosurgery plan is to maintain a sharp radiation dose falloff from the high radiation dose regions (high dose regions) inside the tumor to the low radiation dose regions (low dose regions) of nearby healthy structures. The steep radiation falloff rate of dose distribution—known as the "dose falloff rate"—guarantees that normal, healthy tissue and other body parts or structures near the target receive a low dose of radiation while the center of the target or tumor receives a high dose of radiation. Sharper radiation dose falloff will results in better tumor control and less damage to the normal tissue and other body parts surrounding the tumor that are irradiated by the radiation beams.

Focused Beam Geometry:

Currently, most radiosurgeries are performed in a "step-and-shoot" manner and use a number of precisely focused external beams of radiation that are aimed at the target from different directions to increase the dose falloff rate (see FIG. 1). In this technique, as the number of radiation beams increases, the dose falloff rate improves. Therefore, a large number of radiation beams focus on a target to create a high dose region around the target at the point of intersection of the beams. Intuitively, if the number of beams is increased, the contribution of each beam inevitably decreases, resulting in a lower dose to the tissues and structures some distance away from the target. This is because more beams pass through different parts of the body at lower radiation doses but collectively provide the same radiation dose to the target.

However, in these conventional radiation treatments the number of radiation beams is constrained to several hundred beams due to various spatial and physical constraints. For example, in Gamma Knife® radiosurgery, the number of radiation beams is limited to about two hundred beams. Physically, it is not possible to drill a large number of apertures in a fixed size metal screen without eventually causing interference among the beams escaping from the apertures. For intensity-modulated radiation therapy (IMRT), it is usually not practical to deliver more than a dozen beams due to prolonged treatment time. Even with rotational techniques, such as Tomotherapy, intensity-modulated arc therapy (IMAT), volumetric modulated arc therapy (VMAT), and arc-modulated radiation therapy (AMRT), the maximum number of radiation beams is still limited to a few hundred.

Fundamental Physics Underlying Photon Radiosurgery:

The fundamental physics underlying photon-based radiosurgeries includes high energy photon production and photon interactions with matter.

Generally, high energy photons used in current radiosurgeries are produced either by radioactive decay from Cobalt-60 sources or bremsstrahlung interactions in a linear accelerator. In the linear accelerator, electrons are accelerated in an electric field to a high energy and then collide with a metal target. This generates radiation particles or photons in a bremsstrahlung process. The photons produced from Cobalt-60 are called "γ-ray" or gamma rays whereas the photons produced from a linear accelerator are called "X-ray" or X-rays.

Typically photons produced by different sources are heterogeneous in energy. For example, the energies of γ-rays emitted by Cobalt-60 are 1.17 and 1.33 MeV. The energy spectrum of X-rays from a linear accelerator shows a continuous distribution of energies for the bremsstrahlung photons superimposed by characteristic radiation of discrete energies. The energies of photon beams created by a 6 MV accelerator are continuous from 0 to 6 MeV with a large number of photons having energy around 2 MeV. For examples, Gamma Knife®(see FIG. 3) uses γ-rays emitted from radioactive Cobalt-60 sources to irradiate tumors, while Cyberknife® (see FIG. 4), which is essentially a linear accelerator carried by a robotic arm, uses X-rays to irradiate tumors.

When photons pass through matter, they interact in one of three ways: Photoelectric effect, Compton effect and Pair production. For radiosurgery, the predominant interaction is the Compton effect, where the incident photons collide elastically with orbit electrons. During this elastic collision, energy is imparted from the incident photons to orbiting electrons and sets off a chain of reactions. These electrons know as secondary electrons, as they travel through matter, produce ionization and excitation along their path. On a cellular level, these ionizations damage DNA and cause cell death in the body.

Important Beam Characteristics for Treatment Planning:

A percent depth dose curve relates the absorbed dose deposited by a radiation beam into a medium. FIG. 2(a) shows the percent depth dose curve of Cobalt-60 with an 80 cm Source Surface Distance (SSD). Two parameters of a radiation beam are its Tissue Maximum Ratio (TMR) and Off Center Ratio (OCR). TMR is defined as the ratio of the dose at a given point in phantom to the dose at the same point at the reference depth of maximum dose. OCR is the ratio of the absorbed dose at a given off-axis point relative to the dose at the central axis at the same depth. FIG. 2(b) shows the TMR of Cobalt-60 and a 6 MV accelerator. FIG. 2(c) shows the OCR of a 6 MV accelerator.

SUMMARY OF THE INVENTION

The present invention improves the quality of radiosurgery by increasing the dose fall-off rate. The dose fall-off rate is determined from high dose regions inside a target such as a tumor to low dose regions of nearby healthy tissues and body parts or structure.

In order to further improve the focusing power of radiosurgery, dynamic strategies are implemented in the present invention. A beam source is directed around a focused point in a three dimensional (3D) trajectory and may provide a constant change of dose rate, speed, and beam directions to create kernels. The dynamic motion is equivalent to focusing tens of thousands of beams at a focus point and therefore creates kernels with a much sharper dose falloff.

The present invention uses a new optimization paradigm called "kernelling and de-convolution". The paradigm uses two key steps: (1) kernelling, in which a subset of beams is "grouped" together by convolution to form "dose kernels", and then optimized based on the kernels. (2) de-convolution, in which, once kernel level optimization is done, the kernels are de-convolved into individual beams to form a final dynamic plan. Instead of relying on numerical optimization, the present invention uses a hybrid geometric technique that involves geometric routing in both steps, and thus avoids the daunting task of optimizing hundreds of thousands of beams numerically.

Specifically, a radiation beam is moved along a helical type trajectory to dynamically irradiate a target and thereby further improve the dose falloff rate. This approach according to the present invention is termed herein as "dynamic photon painting" (DPP). The dose distribution from this convergence of tens of thousands of beams on a small volume is used as the DPP kernel.

As mentioned previously, the key to radiosurgery is the dose falloff rate. According to the present invention, DPP moves a beam source around an isocenter in a 3D trajectory, which is equivalent to focusing thousands of beams on a single point, to increase the dose falloff rate. FIG. 5 illustrates the trajectories of the radiation beam in DPP. The beam source rotates around the center of the target from latitude angle $\phi_1$ to $\phi_2$, and 360° around in longitude angle.

The present invention also overcomes computational problems using the DPP approach. The least square problem often occurs as a key sub-problem of some larger computational problem, such as radiosurgery treatment planning. The least square problem is defined as min $\|Ax-b\|^2$. Intuitively in this model, each column of A represents a radiation beam, the column vector b represents the ideal dose distribution and the goal of the optimization is to find the optimal "beam on time" for each column (i.e. X) to create a distribution as close to b as possible. Since in reality, "beam on time" must be non-negative, it is required $x \geq 0$, which gives the Non-Negative Least Square (NNLS). The following is a brief discussion of the solution of a least square problem and NNLS problem. If the total treatment time must stay under a given threshold T, we end up with the constrained least square problem with the constraint $$\sum_{x \in X} x \leq T.$$

There are many algorithmic solutions to the least square problems as is known to those skilled in the art.

The present invention and its attributes and advantages further understood, are further appreciated with reference to the detailed description below of some presently contemplated embodiments, taken in conjunction with the accompanying drawings.

BRIEF DESCRIPTION OF THE DRAWINGS

The preferred embodiments of the invention are described in conjunction with the appended drawings provided to illustrate and not to the limit the invention, where like designations denoted like elements, and in which.

DETAILED DESCRIPTION OF THE PREFERRED EMBODIMENTS

Figure 1:
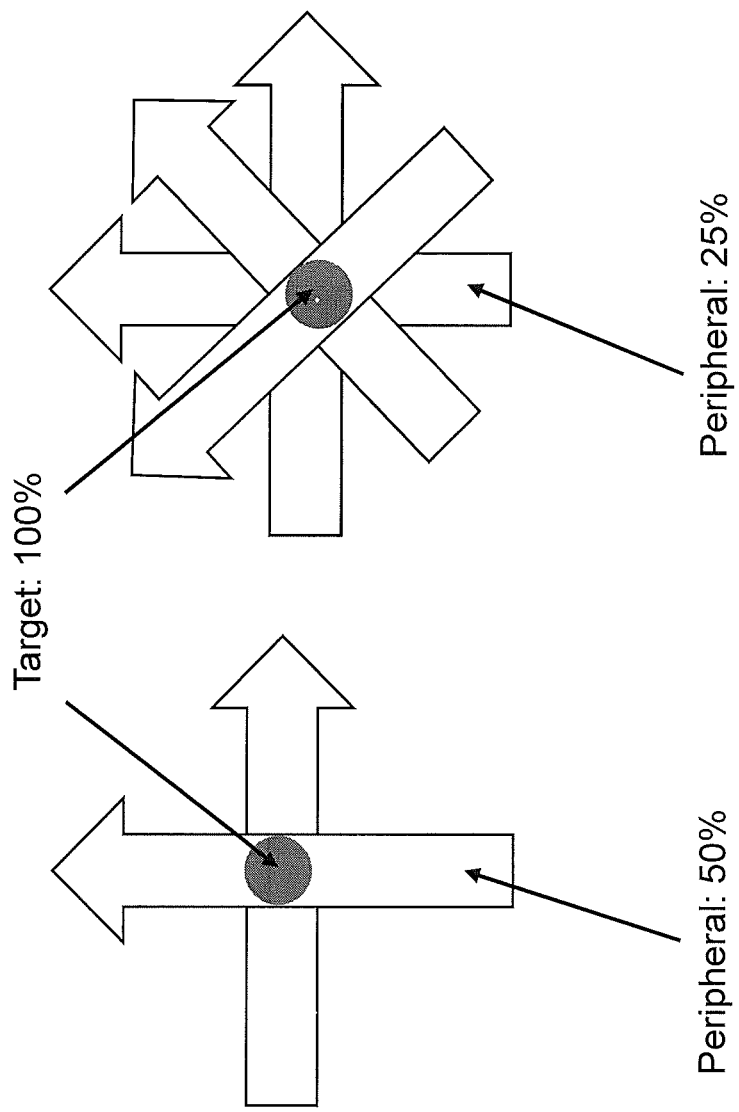
FIG. 1 illustrates the cross-firing technique used in radiosurgery.
Figure 2A:
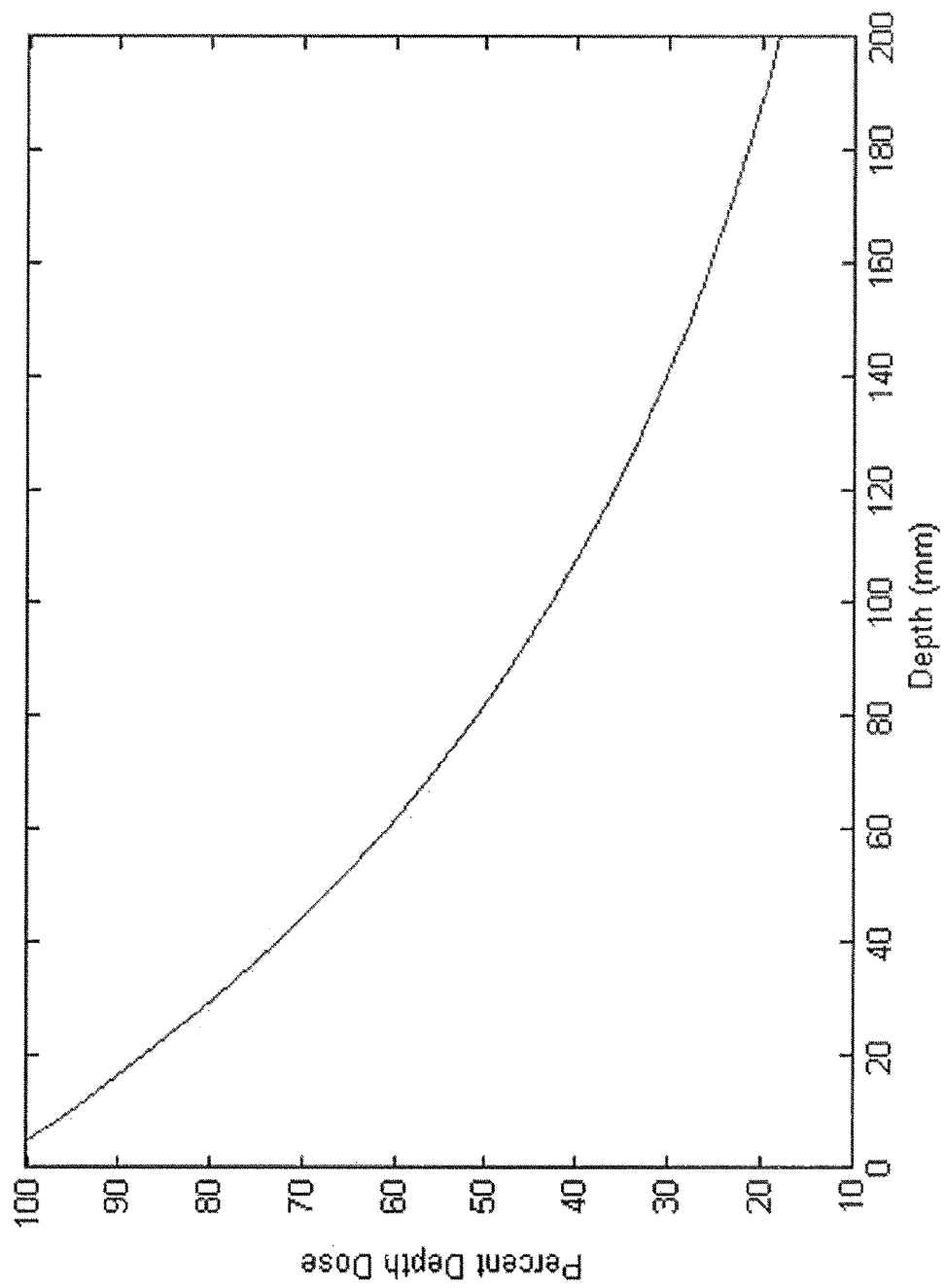
FIGS. 2(a)-(c) illustrate the Percent Depth Dose, Tissue Maximum Ratio and Off Center Ratio curves of Cobalt-60 and 6 MV accelerator sources of radiosurgery.
Figure 2B:
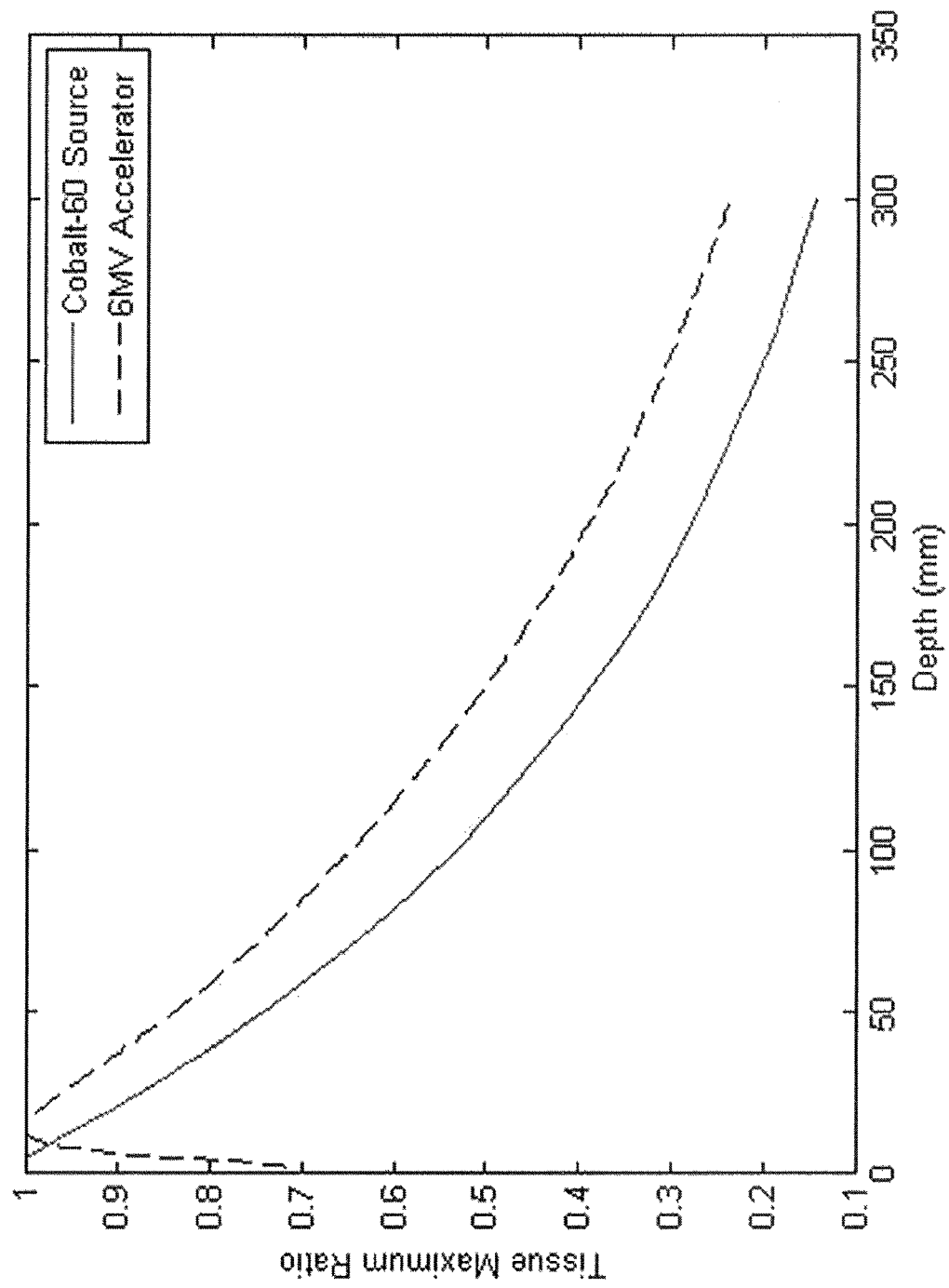
Figure 2C:
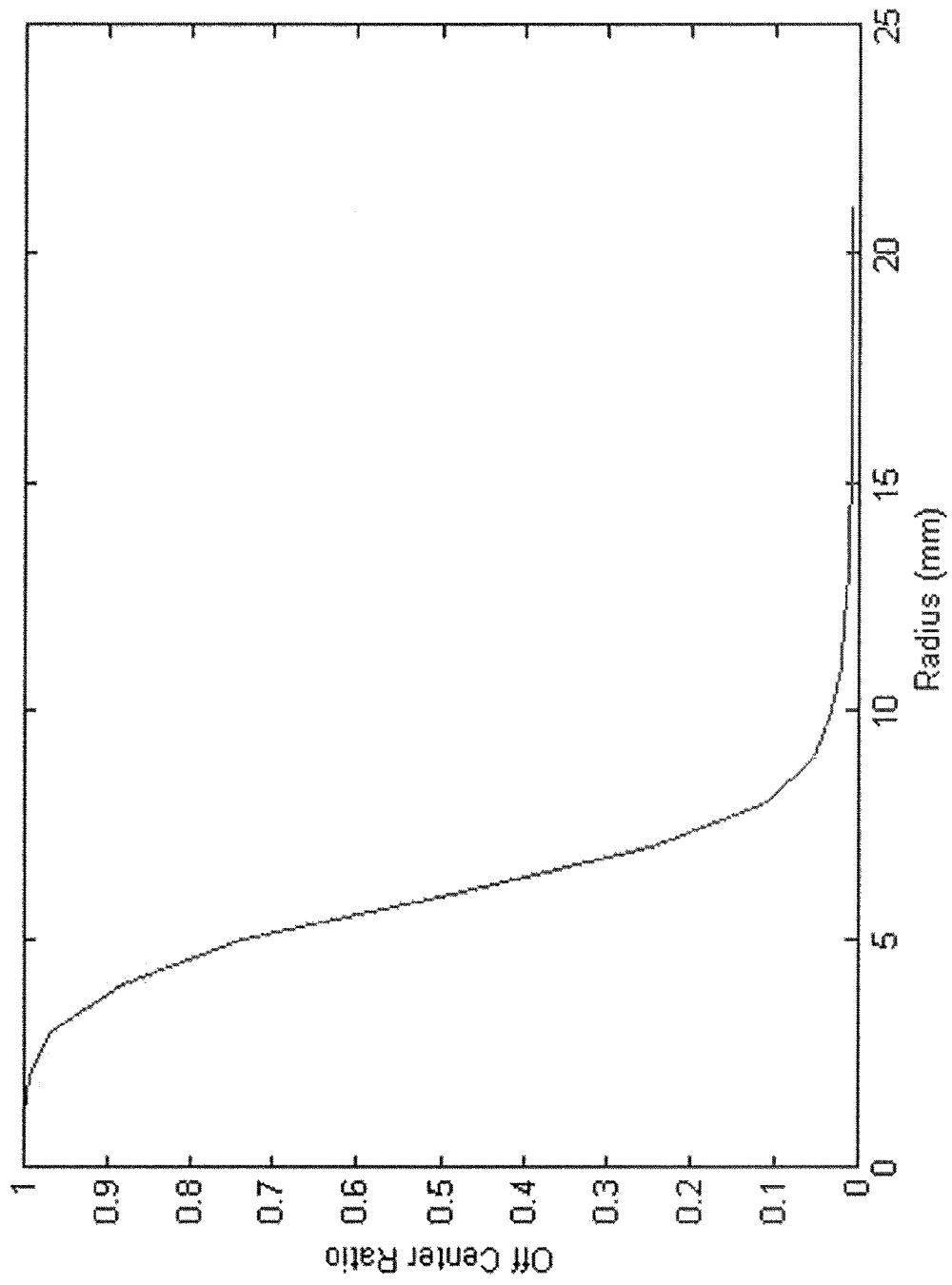
Figure 3:
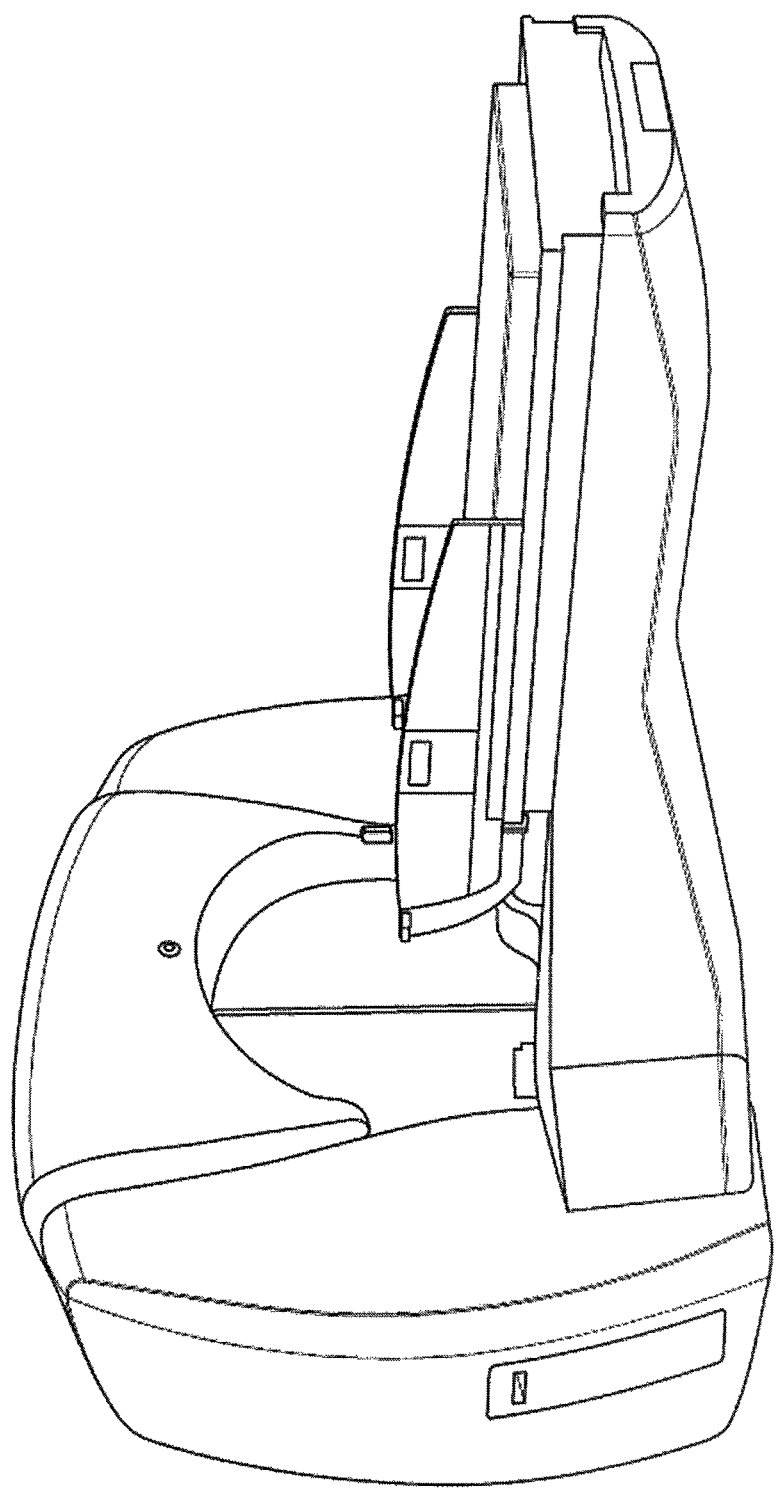
FIG. 3 illustrates a conventional Gamma Knife® machine used in radiosurgery.
Figure 4:
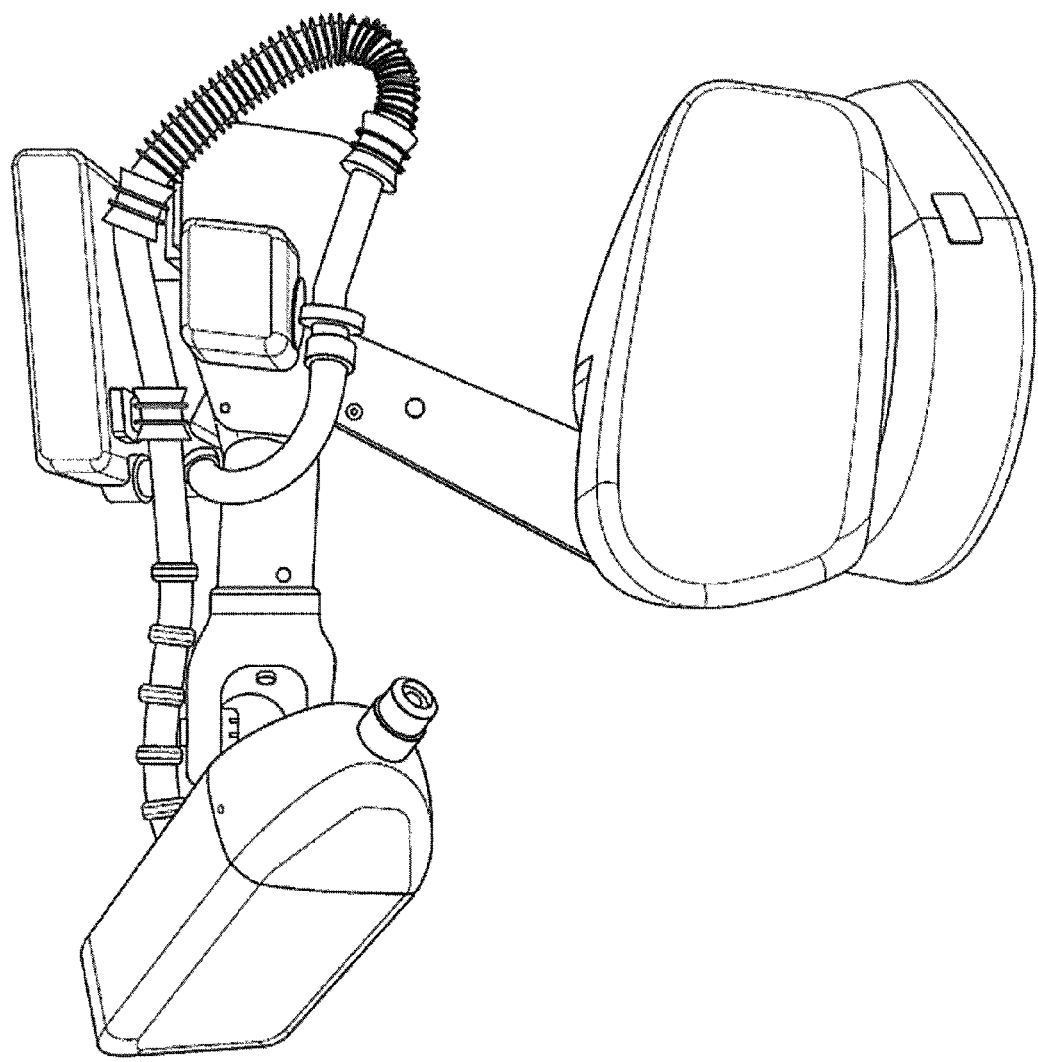
FIG. 4 illustrates a conventional CyberKnife® machine used in radiosurgery.

The present invention is now described in detail with reference to preferred embodiments as illustrated in the accompanying drawings. In the following description, numerous specific details are set forth in order to provide a thorough understanding of the present invention. It is apparent, however, to one skilled in the art, that the present invention may be practiced without some or all of these specific details. In other instances, well known process steps and/or structures are not described in detail in order to not unnecessarily obscure the present invention.

The present invention uses a new optimization paradigm, in which "kernelling and de-convolution" occurs in the following steps: Step 1—(Kernelling) Dose kernels approximating the radiation dose distributions of about 10,000 focused beams are created by convolving thousands of equivalent beams via preset 3D trajectories; Step 2—(Dose painting) The dose kernel is viewed as a 3D "paintbrush" and an optimal route of the paintbrush is calculated to dynamically "paint" the targeted tumor volume; and Step 3—(De-convolution) The kernel is de-convolved along the route from Step 2 into a single or a few merged trajectories extending into a $4\pi$ solid angle of varying source-to-focal distances, which are connected into a dynamic treatment plan using geometric routing algorithms.

One advantage of the present invention kernelling and de-convolution paradigm is routing convolved kernels rather than numerically optimizing individual beams. By doing this process, the daunting task of optimizing hundreds of thousands of beams simultaneously is avoided, which even if implemented may prove to be too computational intensive to be practical.

Kernels are created by convolving 2,000 to 10,000 individual beams along preset 3D trajectories. This step requires a determination of the kind of beam profiles, cross-section shapes, and 3D trajectories that are mostly suited for dynamic radiosurgery in terms of creating the most sharp dose fall-offs in the kernels.

As an integral part of the planning system, a library of kernels is created using different beam shapes, profiles, and trajectories. The characteristics of each kernel in the library can be investigated for producing useful dose focusing powers.

By convolving individual beams into kernels and optimizing kernels rather than individual beams, directly optimizing a large number of beams is avoided, and treatment planning is shifted to routing the kernels to dynamically cover the target. To solve this routing problem, techniques from computational geometry are utilized.

The route calculated in the dose painting step will create a high quality plan, however to deliver it using robotic radio-surgery, this route of the kernels must be converted to a feasible dynamic route of a single beam. To accomplish this process, the kernels to individual beams along the route are de-convolved, which results in a set of beams with different orientation and locations. These individual beams are then connected into a tour, which will be the final dynamic radio-surgery plan. Specifically, the following problem is solved: Given a planar region with the presence of polygonal obstacles (e.g., the robotic arm in a CyberKnife® unit is not allowed in certain region for fear of collision with patient or patient table) and a set of sites, find a tour to visit all the sites.

Figure 5:
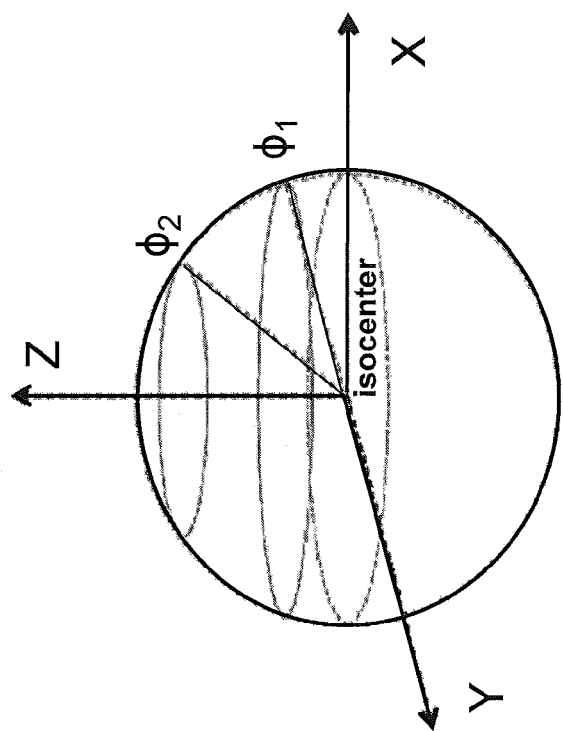
FIG. 5 illustrates the trajectories of the radiation beam in dynamic photon painting according to the present invention.
Figure 5:
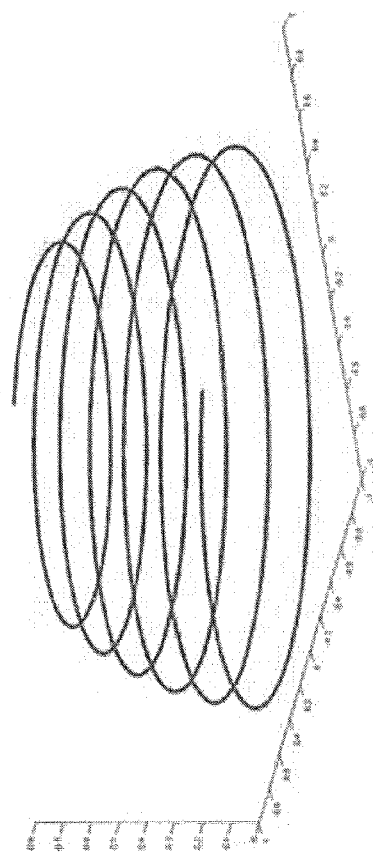

Turning now to FIG. 5, the above process as dynamic photon painting (DPP) may be performed by using a CyberKnife® cone radiation beam that is revolved in a hemispherical trajectory around a target. As shown in FIG. 5 and described above, the beam source rotates around the center of a target from latitude angle $\phi_1$ to $\phi_2$, and 360° around in a longitude angle. The CyberKnife® beam model is obtained from curve fitting of measured Tissue Phantom Ratio (TPR) and Off Center Ratio (OCR) tables.

Figure 6A:
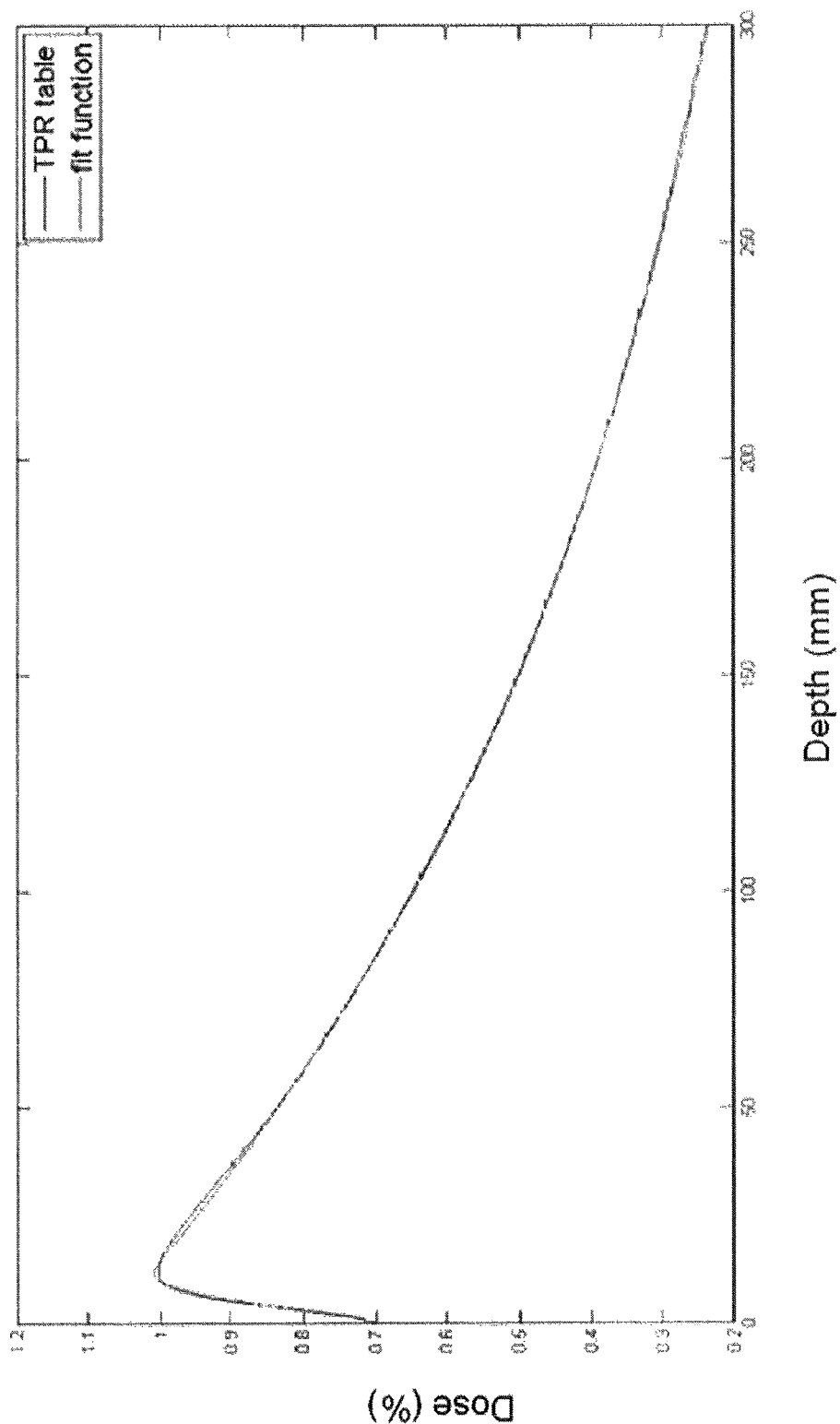
FIGS. 6(a)-(b) illustrate curve fitting results according to the present invention.
Figure 6B:
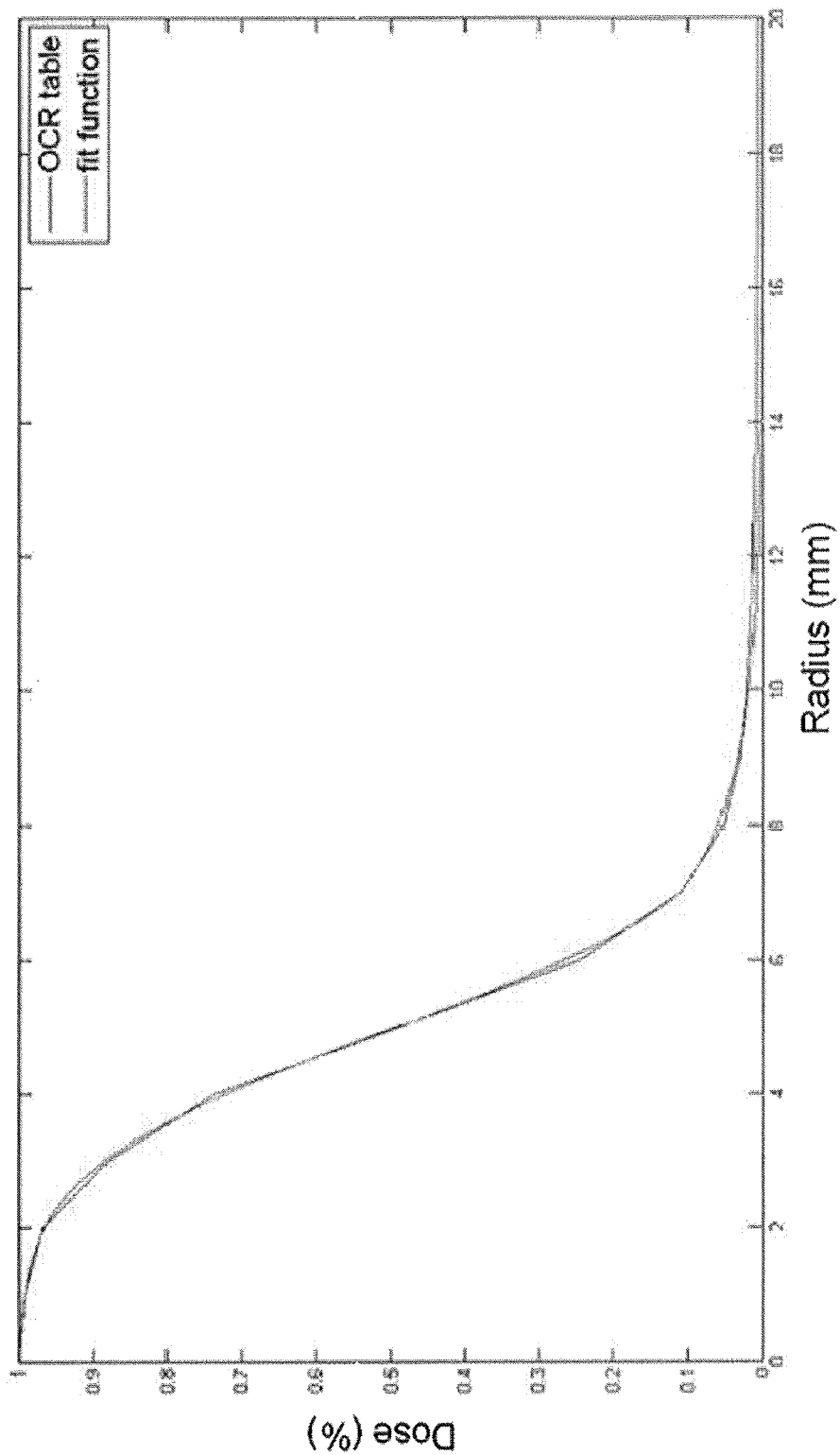

FIG. 6(a) illustrates the curve fitting results for TPR and FIG. 6(b) illustrates the curve fitting results for OCR. The functions used for curve fitting are:

$$TPR(d) = \begin{cases} \sum_{i=1}^{5} a_i d^{i-1} & \text{for } d < d_{max} \\ e^{-a_6 \cdot (d-a_7)} & \text{for } d > d_{max} \end{cases}$$

and $$OCR(SAD, r) = 0.5 \cdot \left( \text{erfc}\left(a \cdot \left(\frac{r \cdot 800}{SAD} - b\right)\right) + \text{erfc}\left(a \cdot \left(\frac{r \cdot 800}{SAD} + b\right)\right) \right),$$

where d is the depth and r is the off-center radius of the calculation point, Source to Axis Distance (SAD)=Source Surface Distance (SSD)+d, and $$\text{erfc}(x) = \frac{2}{\sqrt{\pi}} \int_x^\infty e^{-t^2} dt$$

is the error function. For a 10 mm cone, the curve fitting parameters for TPR are $a_1$=0.8185, $a_2$=0.0203, $a_3$=0.004, $a_4$=−0.0006, $a_5$=0.00002, $a_6$=0.0061, $a_7$=15, and for OCR a=0.4317 and b=4.9375. (Note that the parameter b here is essentially the radius of the field at 800 mm standard SAD).

The motion trajectory of the beam source (see FIG. 5) is described using the following parameters: (1) latitude angular range $[\phi_1, \phi_2]$, (2) longitude angular range $[\theta_1, \theta_2]$, and (3) source to axis distance.

By rotating the radiation beam in a dynamic manner, DPP kernels are created. Comparisons were carried out with Gamma Knife® kernels and proton Bragg Peaks. The DPP kernels were compared with Gamma Knife® Perfexion 4 mm kernels. The Gamma Knife® kernel is a 41×41×41 matrix with 0.5 mm steps.

Figure 7A:
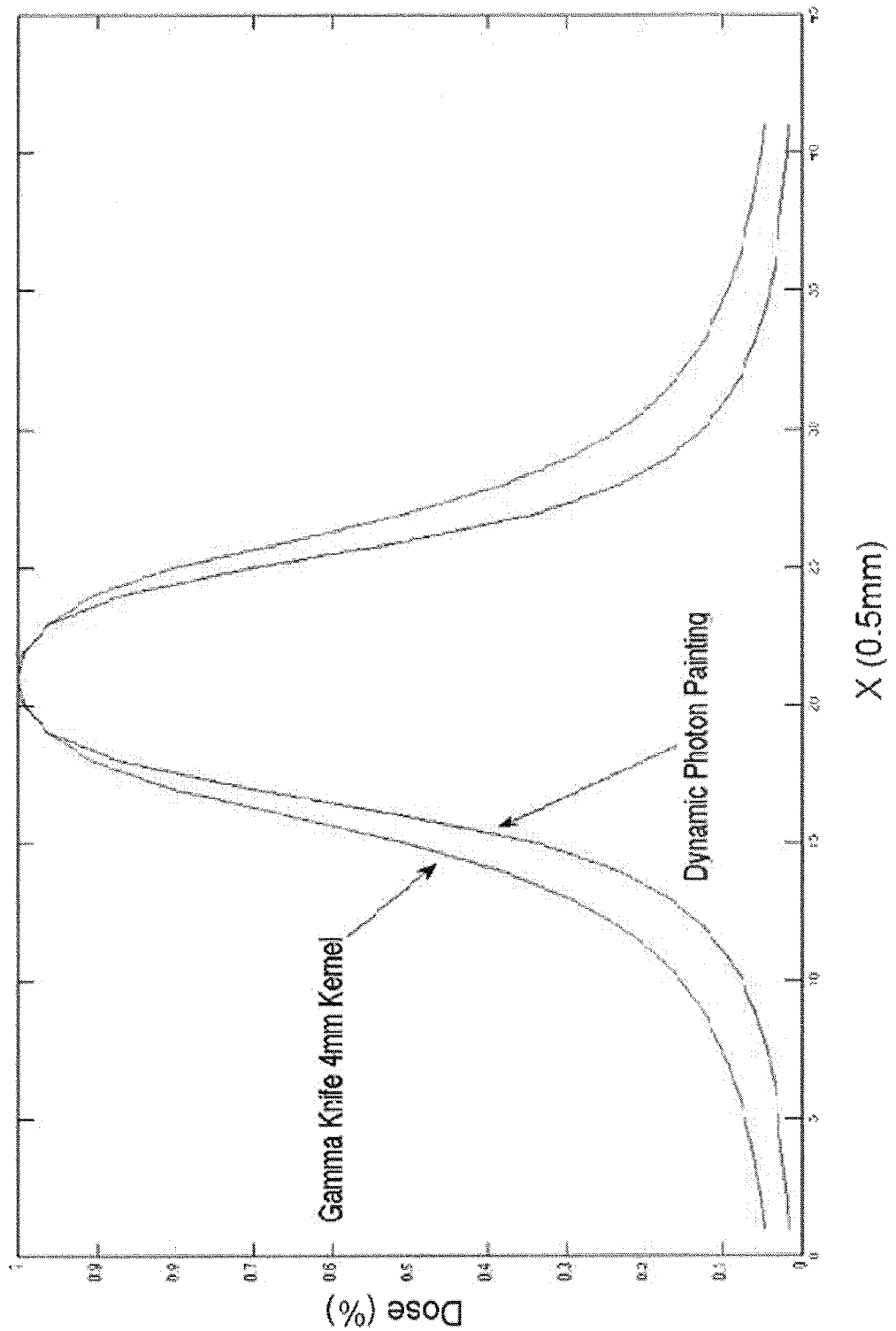
FIGS. 7(a)-(b) illustrate radiation dose profile comparisons between dynamic photon painting (DPP) kernels and Gamma Knife® perfexion 4 mm kernels according to the present invention.
Figure 7B:
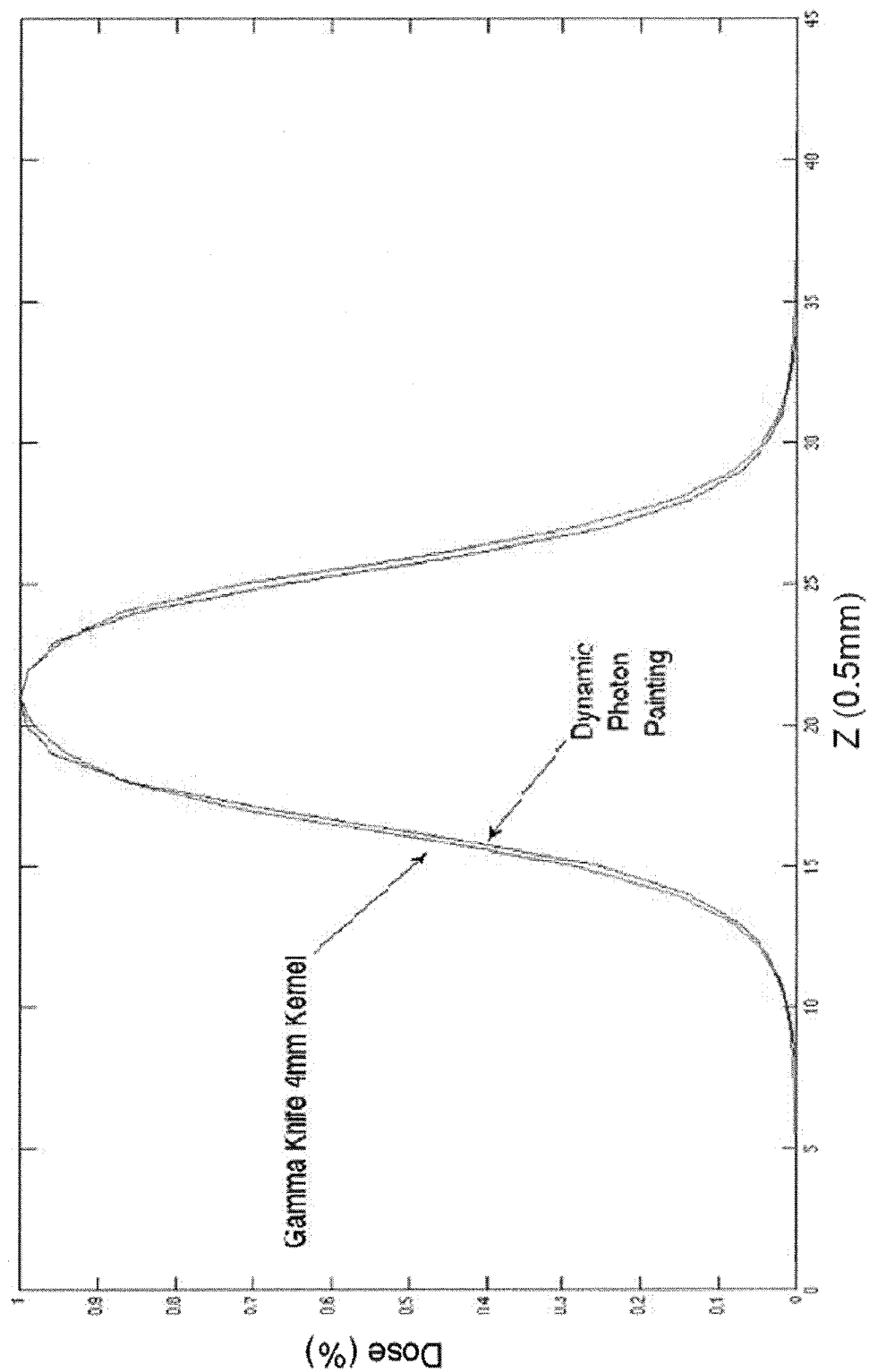

FIGS. 7(a)-(b) show the dose profile comparisons between DPP kernels and Gamma Knife® kernels. As shown, the DPP kernels were created using a 10 mm cone of the CyberKnife® beam model, a SAD of 320 mm, and a latitude angular range of 1° to 50°. The SAD was chosen so that the diameter of the DPP kernel at the isocenter is 4 mm. FIG. 7(a) illustrates the dose profiles in the XY plane (along lateral directions) and FIG. 7(b) illustrates the dose profiles in the XZ plane (along longitudinal directions).

Figure 8A:
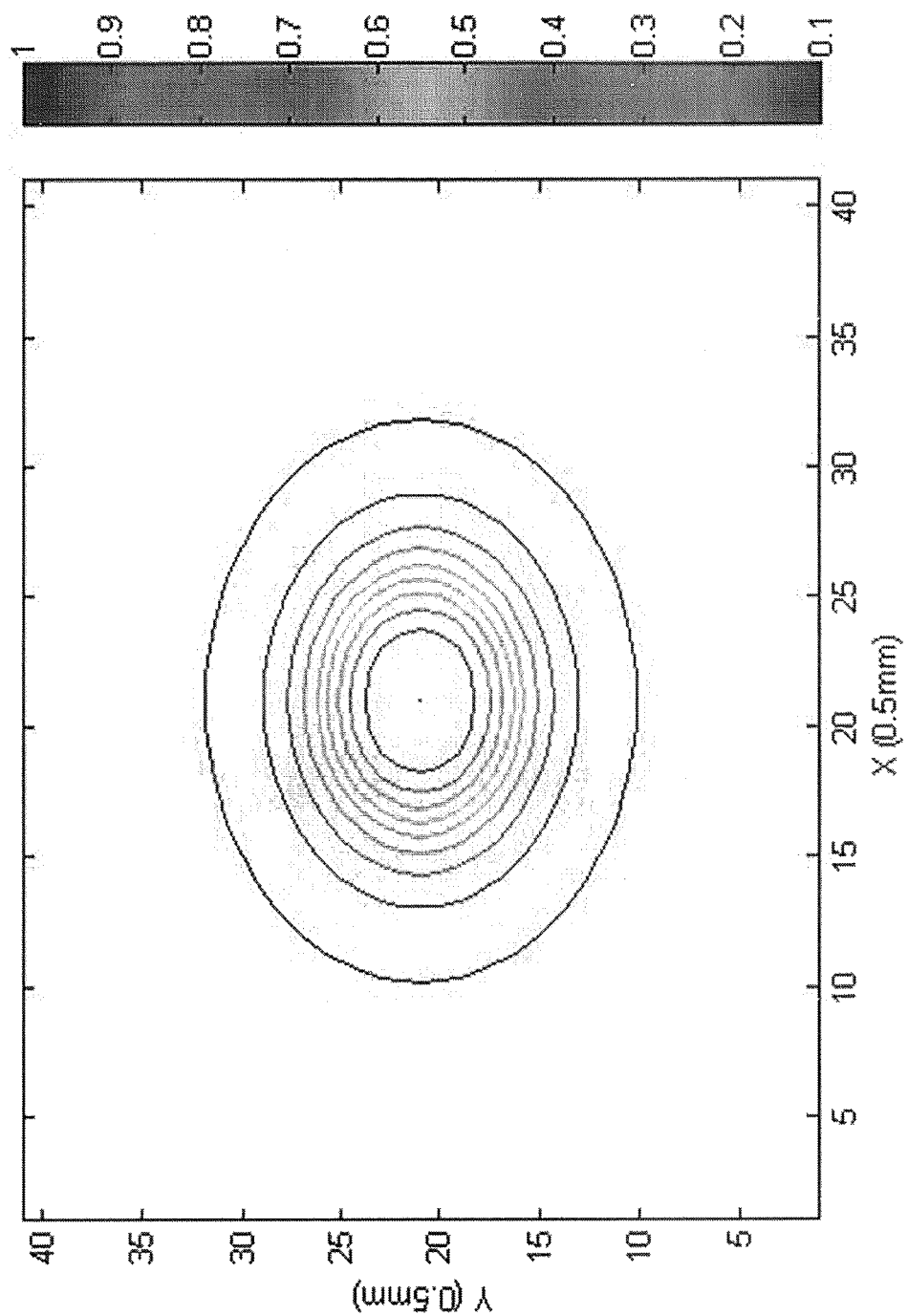
FIGS. 8(a)-(d) illustrate isodose comparisons between DPP kernels and Gamma Knife® perfexion 4 mm kernels according to the present invention.
Figure 8B:
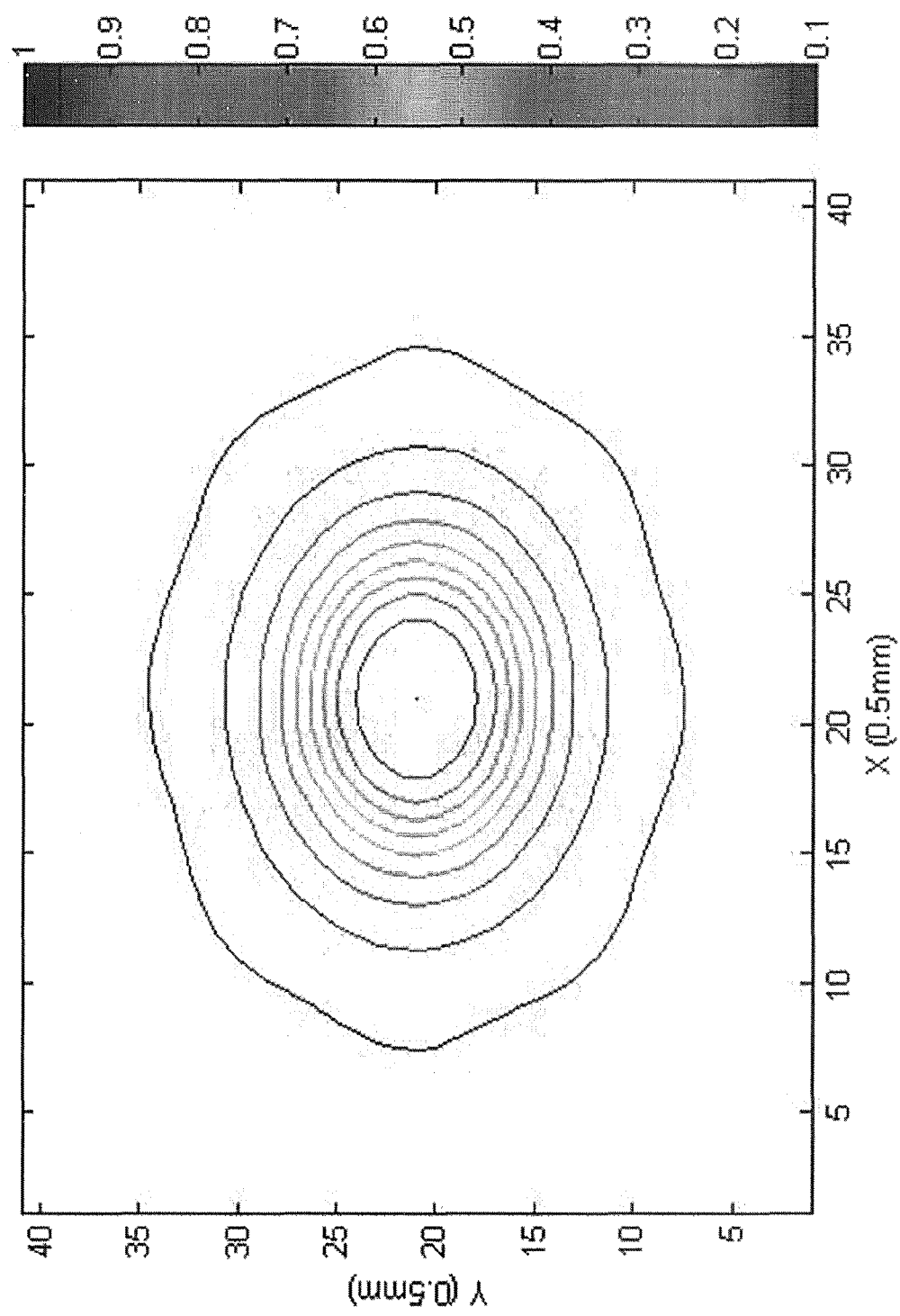
Figure 8C:
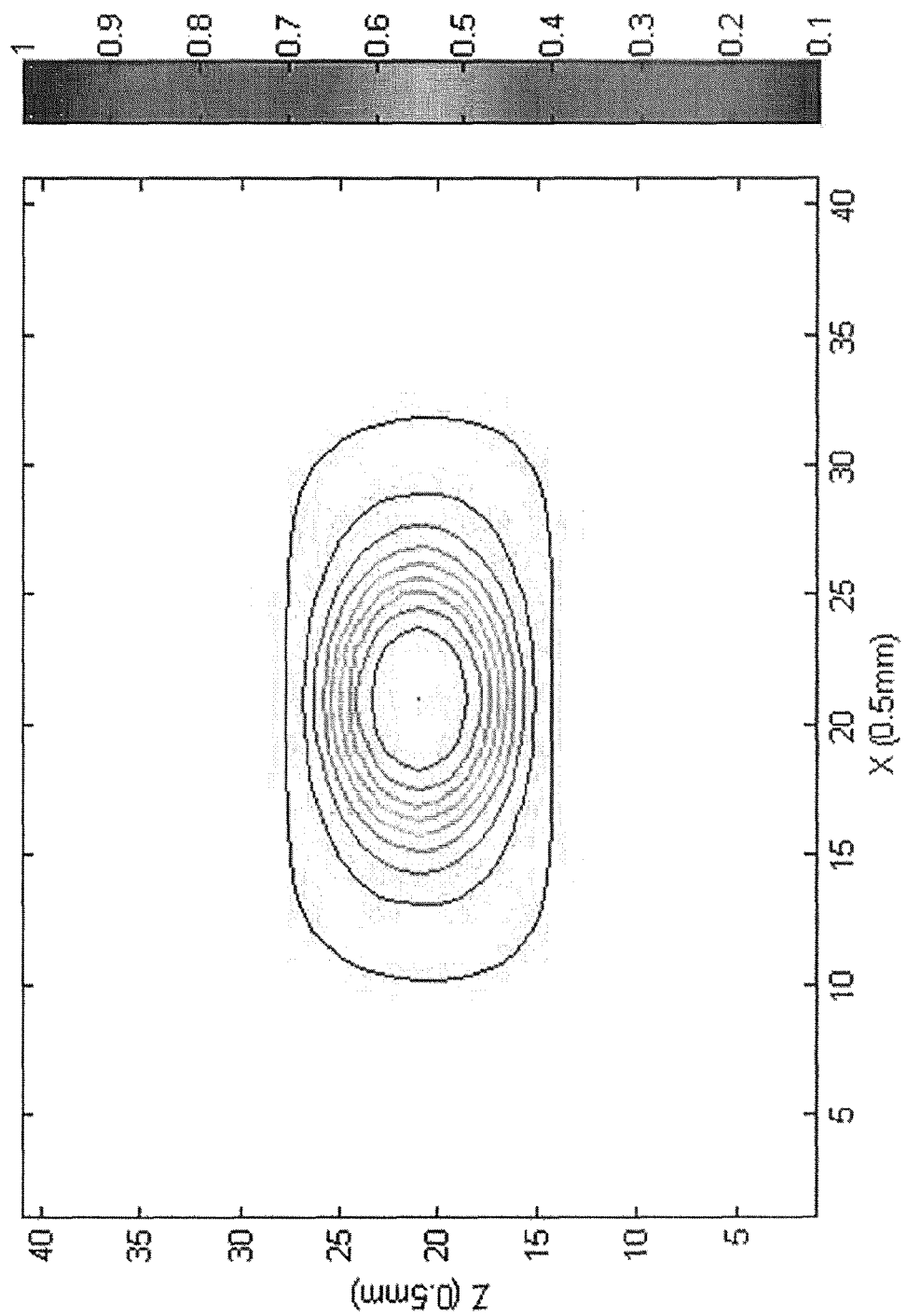
Figure 8D:
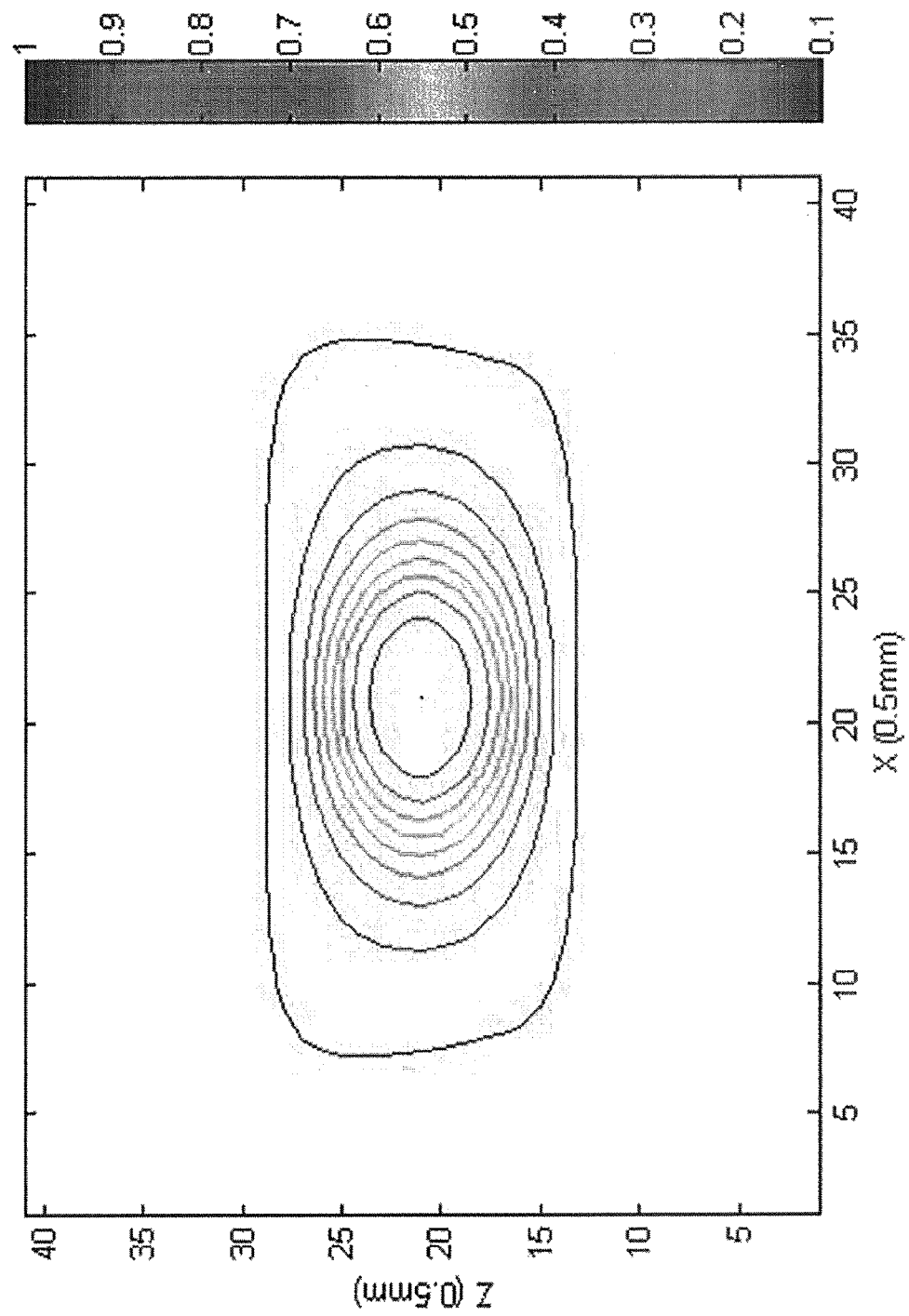

FIGS. 8(a)-(d) show the isodose comparisons of the two kernels, specifically between the DPP kernel and Gamma Knife® Perfexion 4 mm kernels. In these plots, the planes are defined as in FIG. 5. FIG. 8(a) illustrates the DPP kernel in the XY plane. FIG. 8(b) illustrates the Gamma Knife® kernel in the XY plane. FIG. 8(c) illustrates the DPP kernel in the XZ plane. FIG. 8(d) illustrates the Gamma Knife® kernel in the XZ plane. The plot shown contains isodose lines from 10% to 100% with 10% steps. The DPP kernel of the present invention has a sharper lateral fall off than the conventional Gamma Knife® kernel.

Figure 9A:
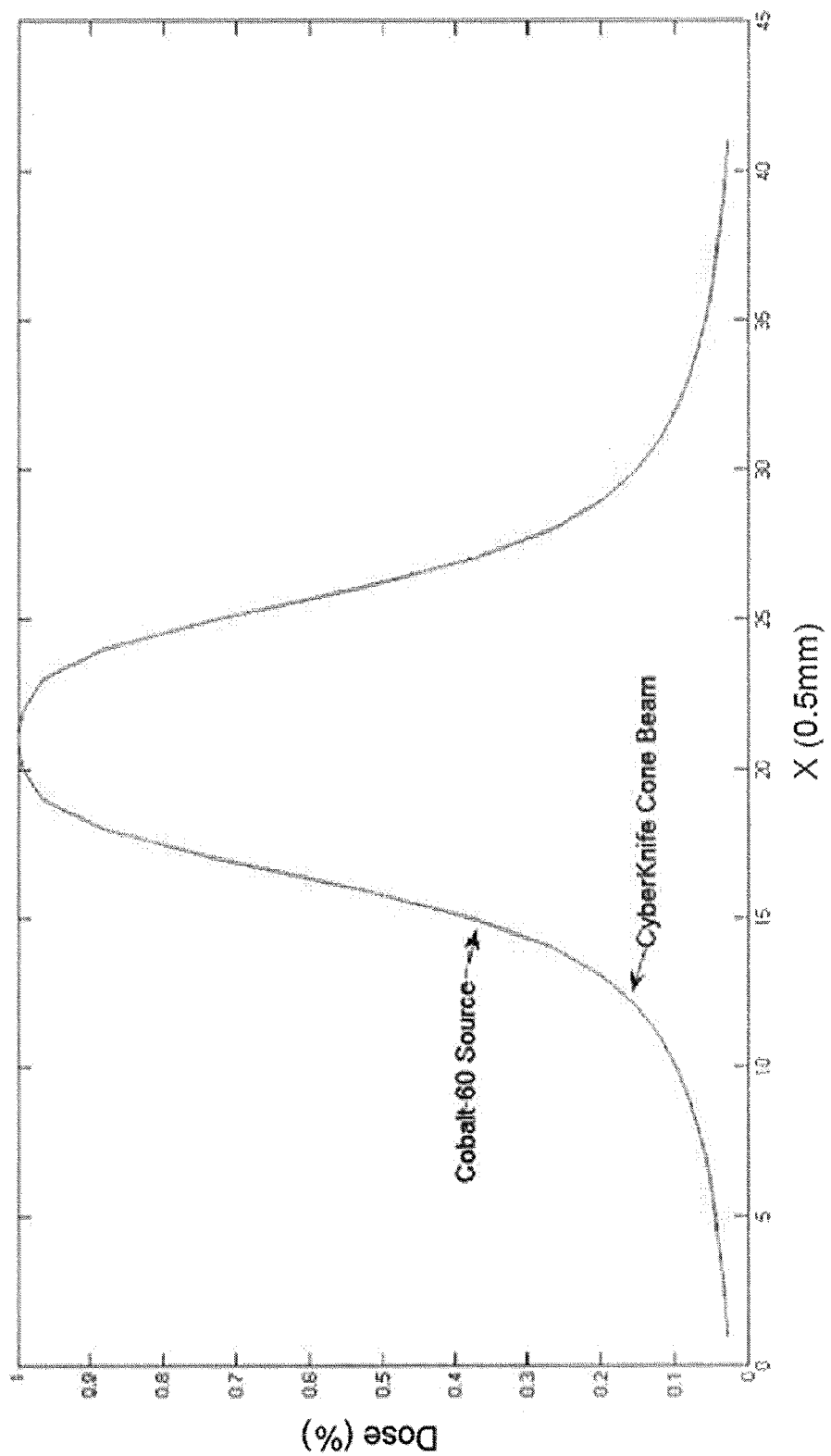
FIGS. 9(a)-(b) illustrate dose profile comparisons between kernels created by Cobalt-60 source and CyberKnife® cone beam according to the present invention.
Figure 9B:
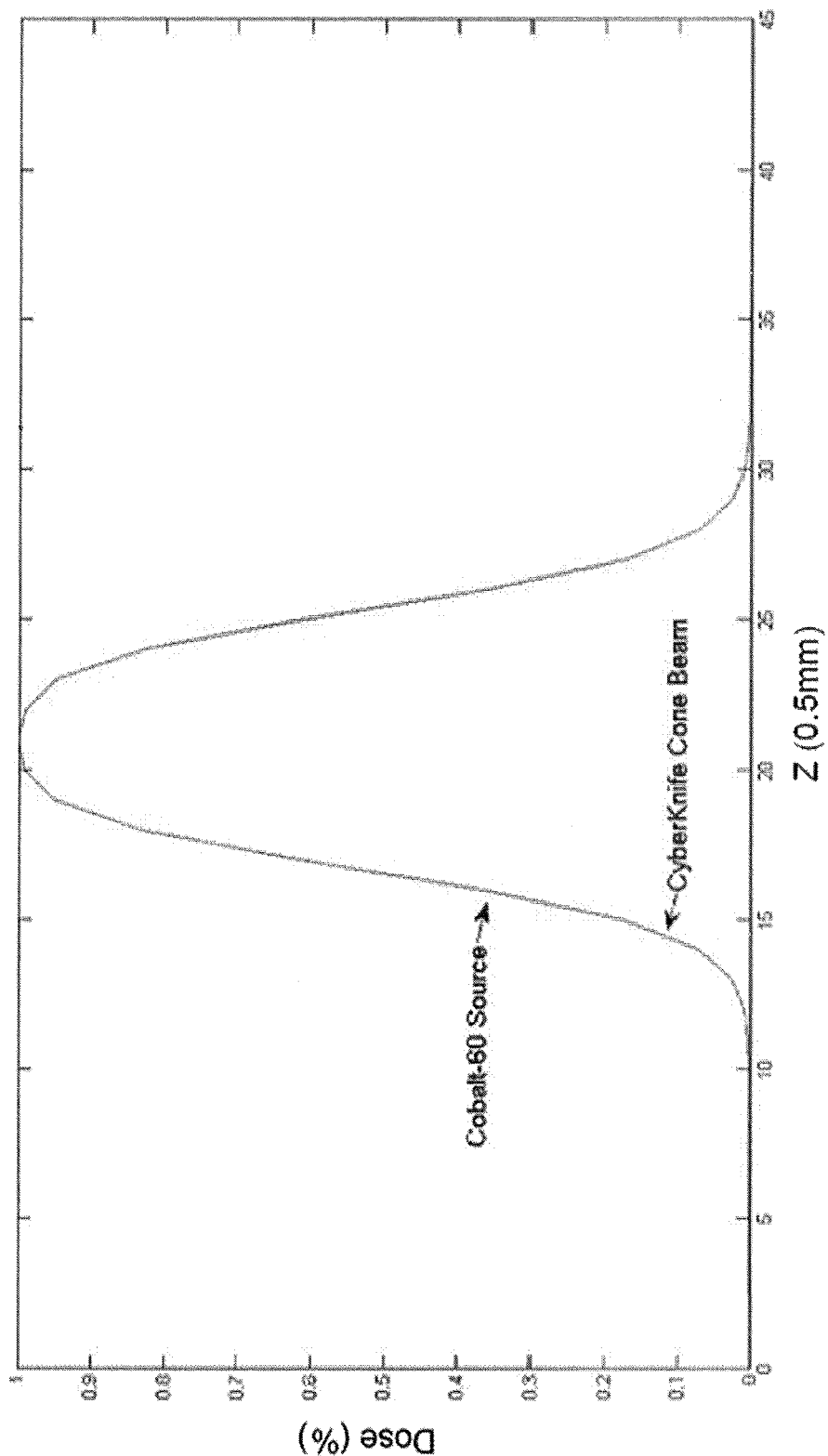

In order to understand whether the DPP strategy or a specific beam source makes the kernel better, the same DPP trajectory was evaluated using a Cobalt-60 Gamma Knife® beam source as the beam source to create kernels and compared to DPP kernels created with the CyberKnife® cone beam. FIGS. 9(a)-(b) show the dose profile comparisons between kernels created by the Cobalt-60 source and the CyberKnife® cone beam. FIG. 9(a) illustrates the dose profiles in the XY plane (along the lateral direction). FIG. 9(b) illustrates the dose profiles in the XZ plane (along the longitudinal direction). The dose profiles are almost identical, which means the impact of beam source is not significant and the DPP strategy causes kernels to have better dose falloff rates.

Figure 10A:
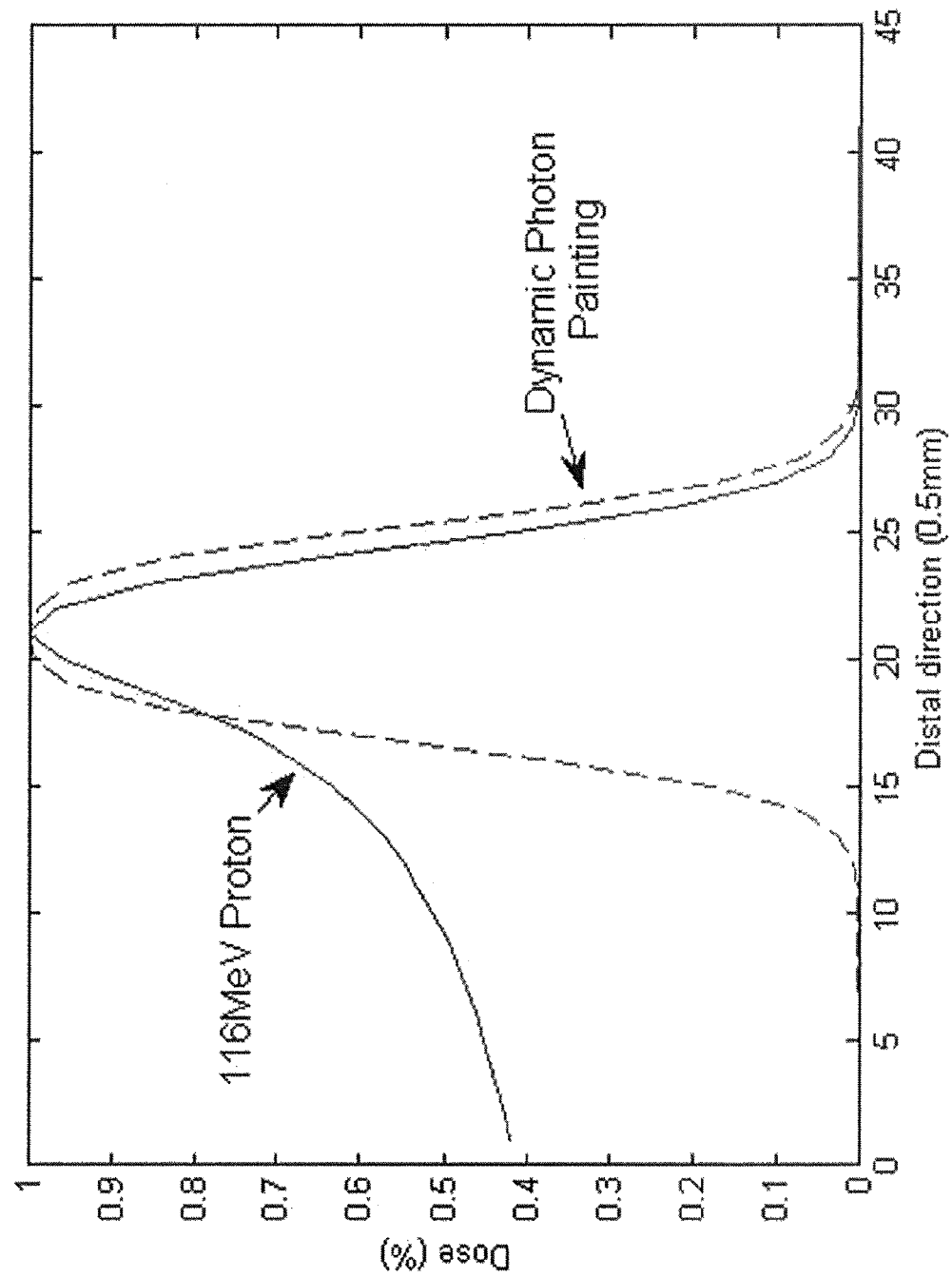
FIGS. 10(a)-(c) illustrate comparisons between the DPP kernel and 116 MeV proton according to the present invention.
Figure 10B:
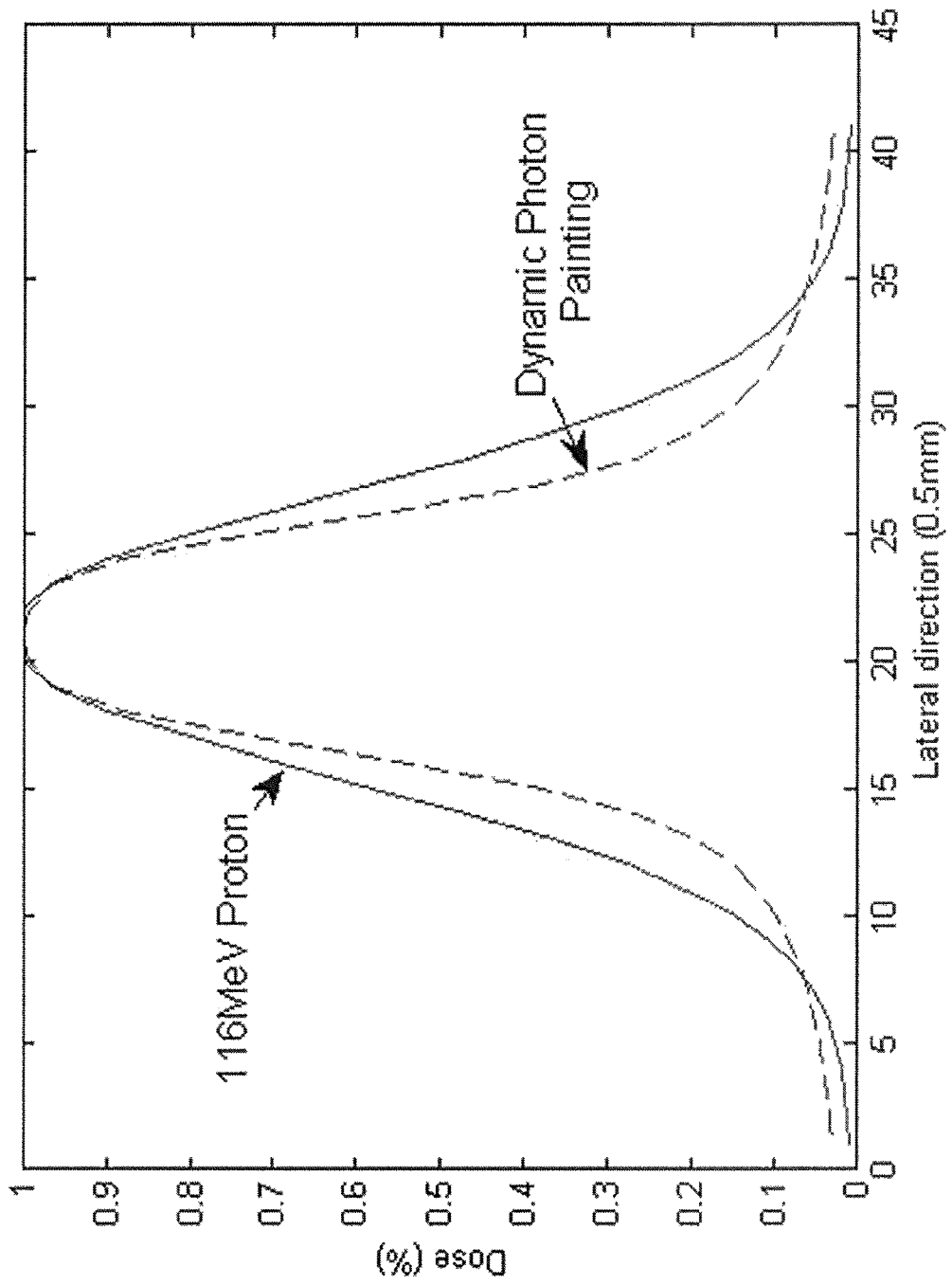
Figure 10C:
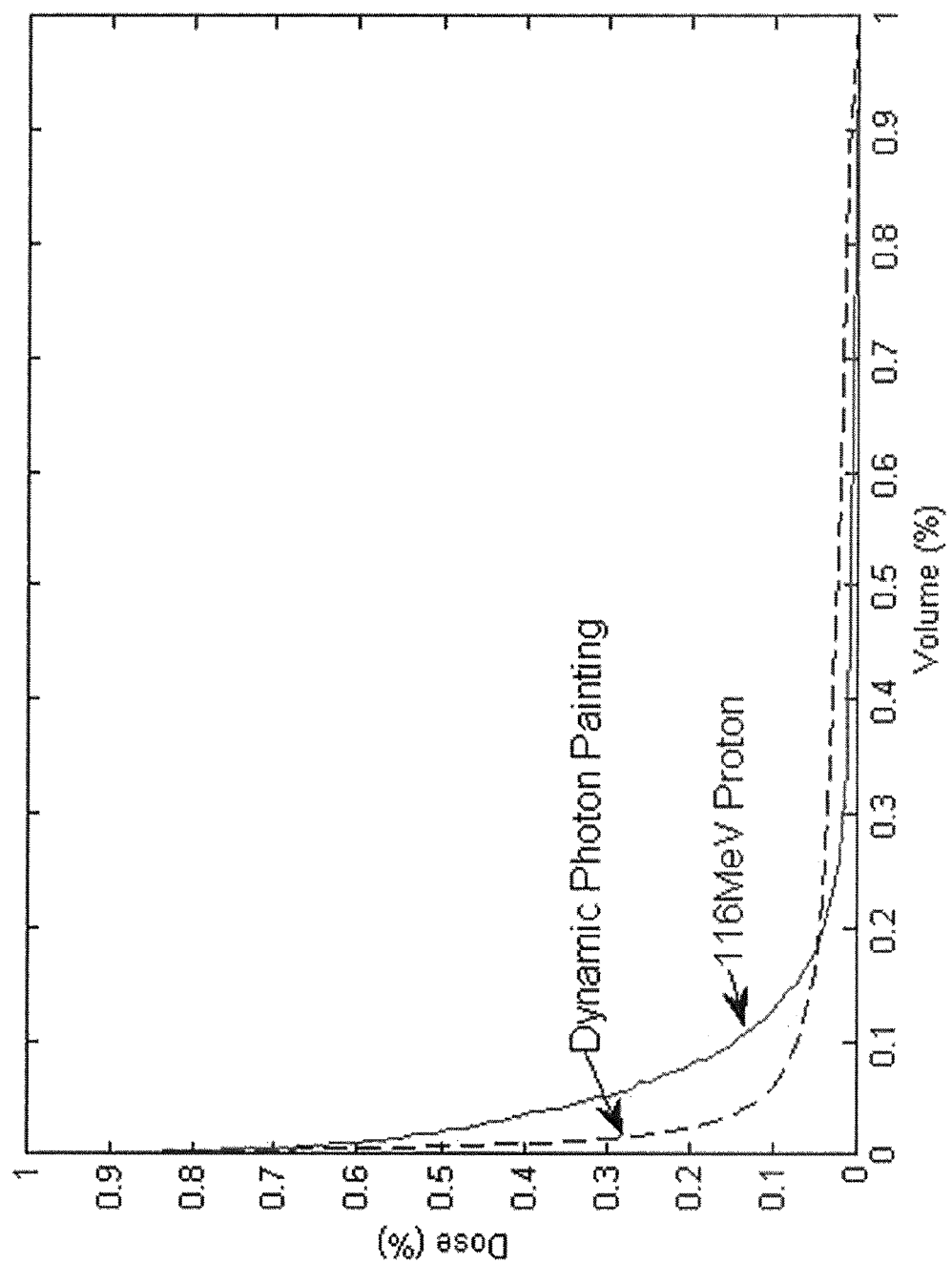

The same DPP kernels were compared with a pristine 116 MeV proton beam. The proton beam was generated in a water phantom with $10^6$ primary protons. The proton beam had a circular Gaussian profile with σ=2 mm. The kernel had a 40 mm radius and bins with 0.5 mm sides and was calculated using the Fluka simulation program. FIG. 9(a) shows the dose profile comparison in the longitudinal direction. FIG. 10(b) shows the dose profile comparison in the lateral direction. FIG. 10(c) shows the VDH comparison. As can be seen, the DPP kernel deposits most of its energy in a small region.

The impact of latitude angular ranges [$\phi_1,\phi_2$] on the dose gradient of the DPP kernels is also considered. By varying $\phi_1$ and $\phi_2$, a set of kernels is obtained and their dose profiles and isodose distributions are compared as discussed below.

Figure 11A:
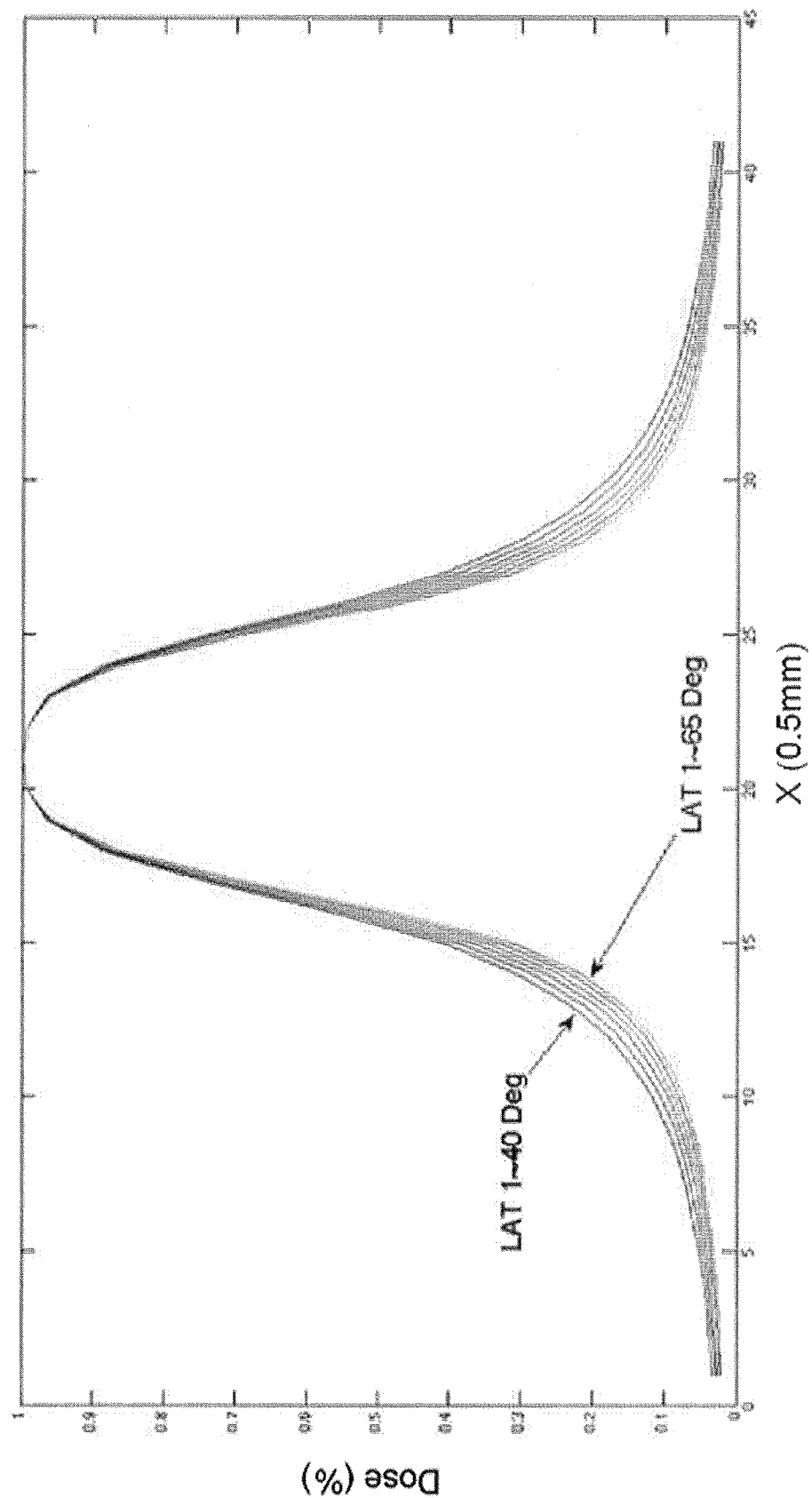
FIGS. 11(a)-(b) illustrate the impact of lateral angular range on the dose gradient of DPP kernels according to the present invention.
Figure 11B:
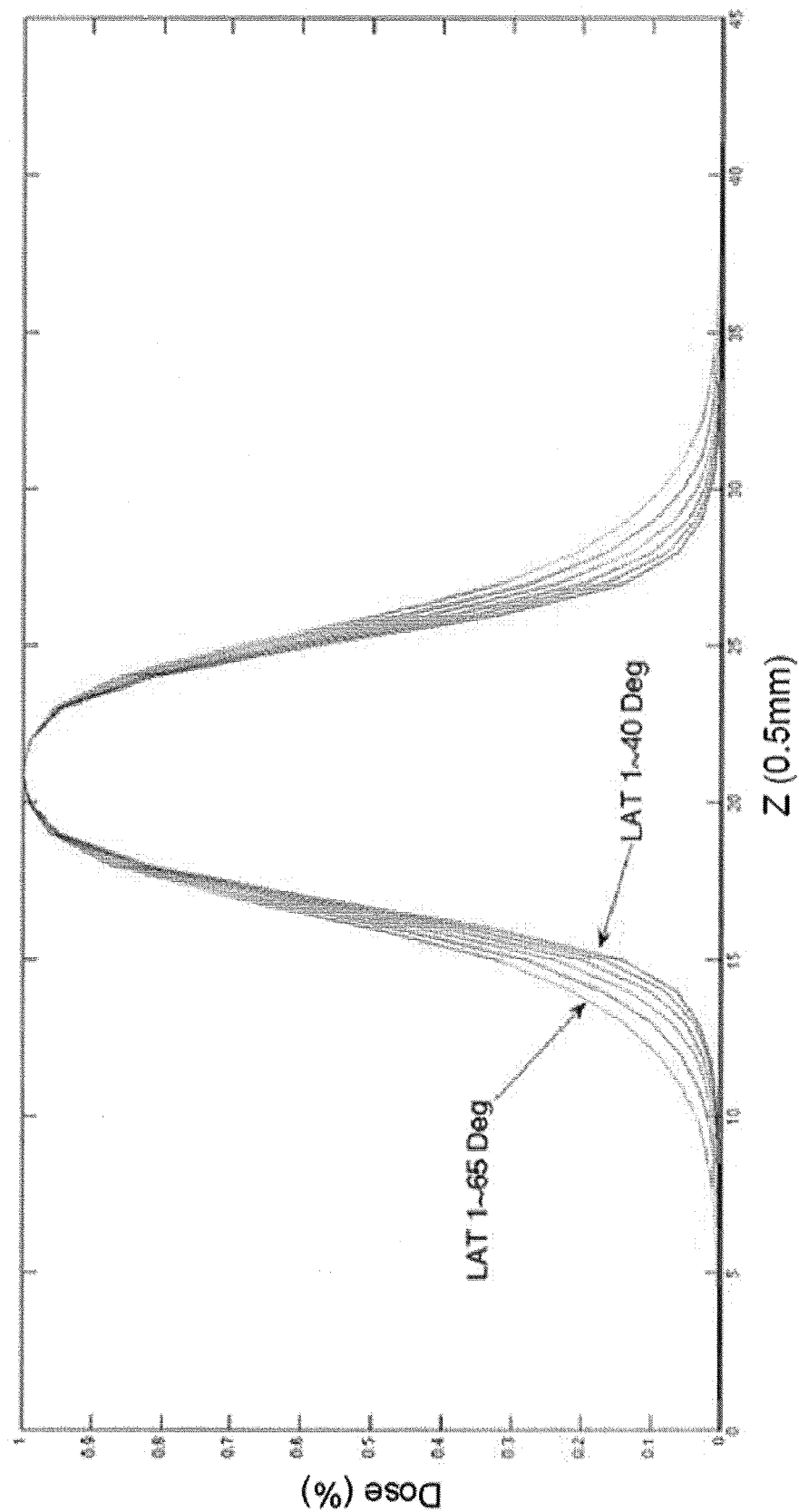

FIGS. 11(a)-(b) show the comparisons of dose profiles with latitude angular ranges of 1° to 40°, 1° to 45°, 1° to 50°, 1° to 55°, 1° to 60°, and 1° to 65°. As $\Delta\phi=\phi_1-\phi_2$ increases, the dose gradient increases in the XY plane (i.e., along the latitude direction) and decreases in the XZ plane (i.e., along the longitudinal direction). The optimal angular range is a tradeoff between the sharpness of dose in the XY plane to that in the XZ plane. In addition to the above comparisons, the impact of $\phi_1$ is considered, the starting latitude angle when $\Delta\phi$ is fixed. The comparisons of the XZ isodose distributions of DPP kernels of different latitude angular ranges are shown in FIGS. 12(a-d).

Figure 12A:
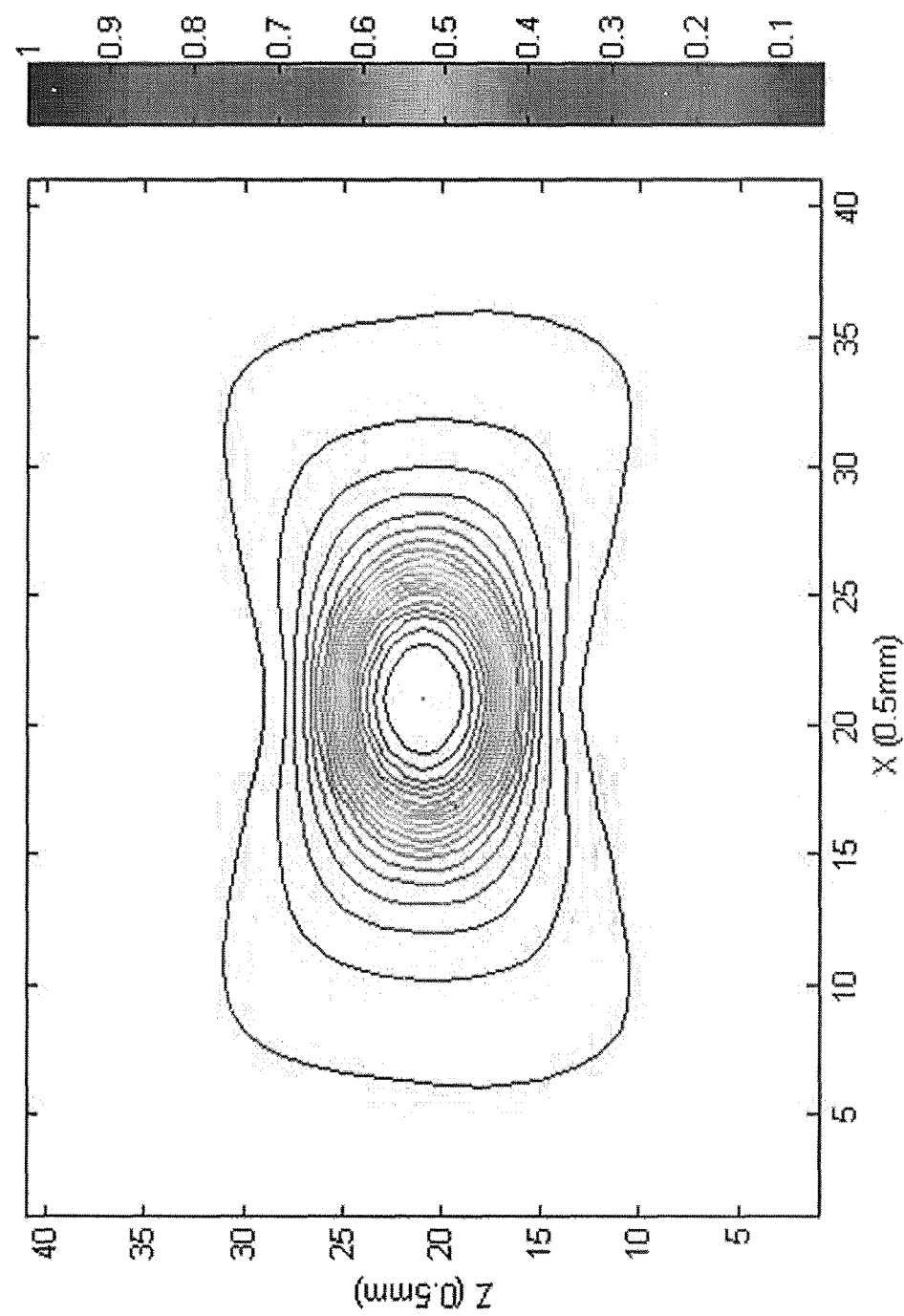
FIGS. 12(a)-(d) illustrate isodose distributions of DPP kernels of different latitude angular ranges according to the present invention.
Figure 12B:
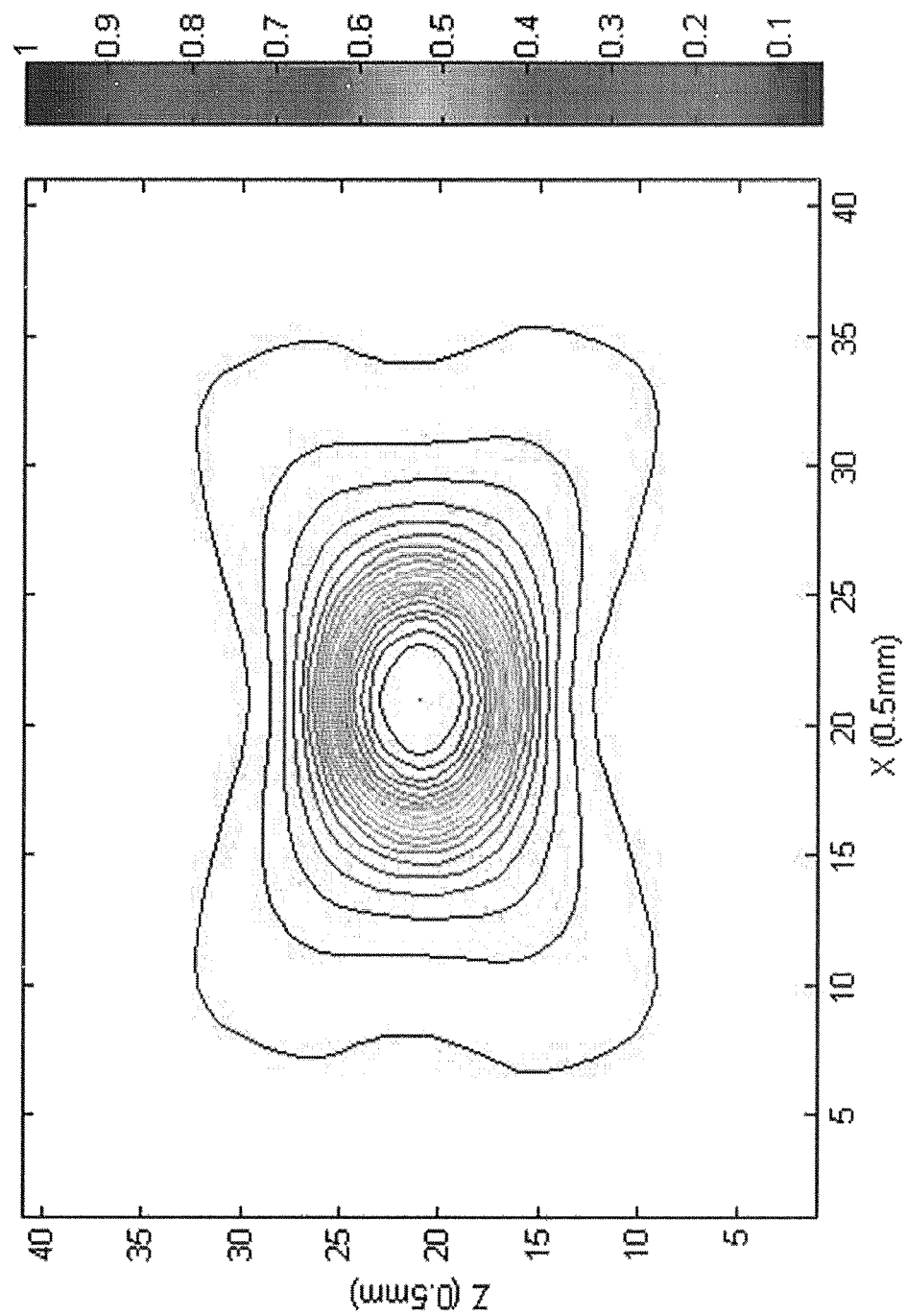
Figure 12C:
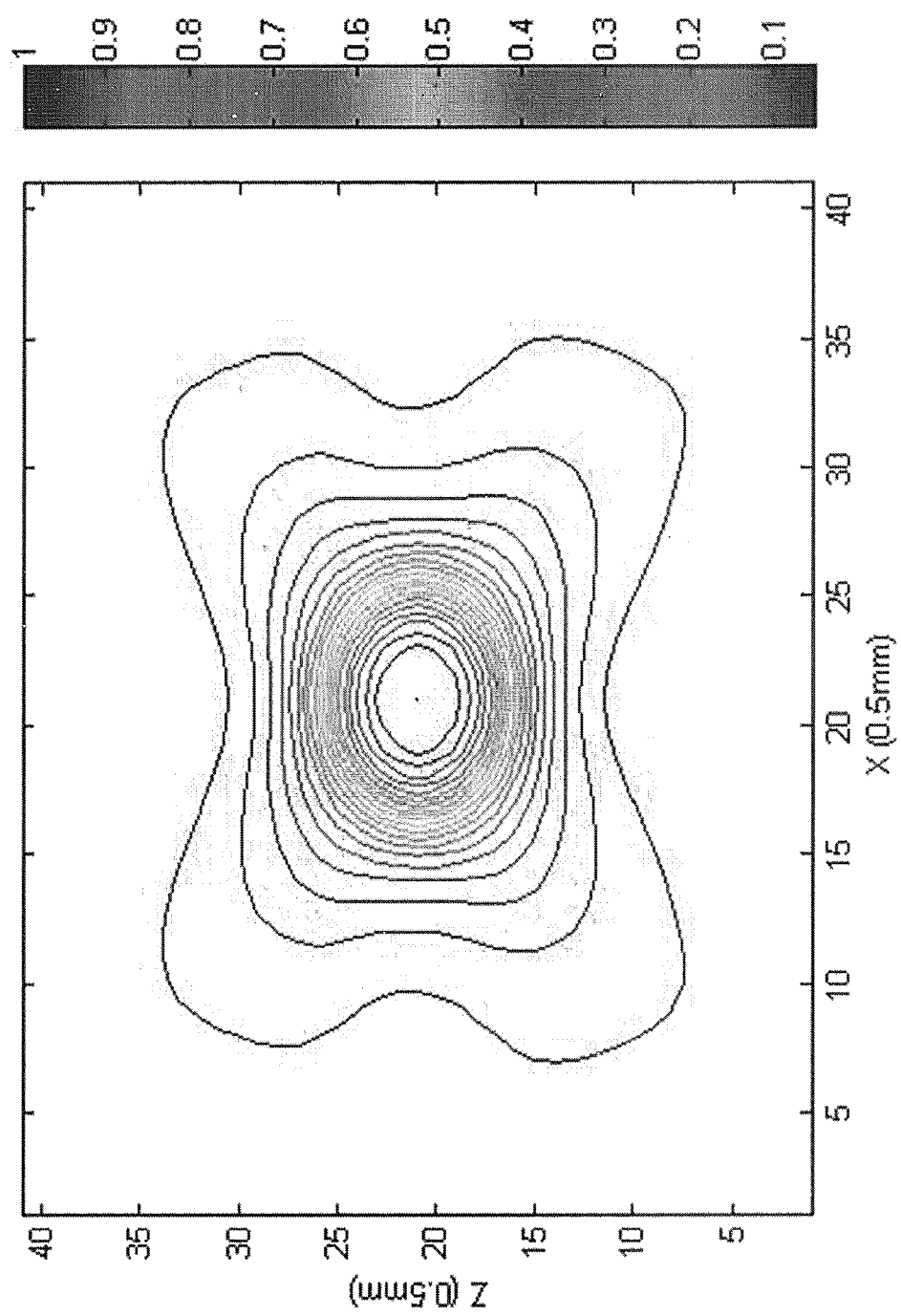
Figure 12D:
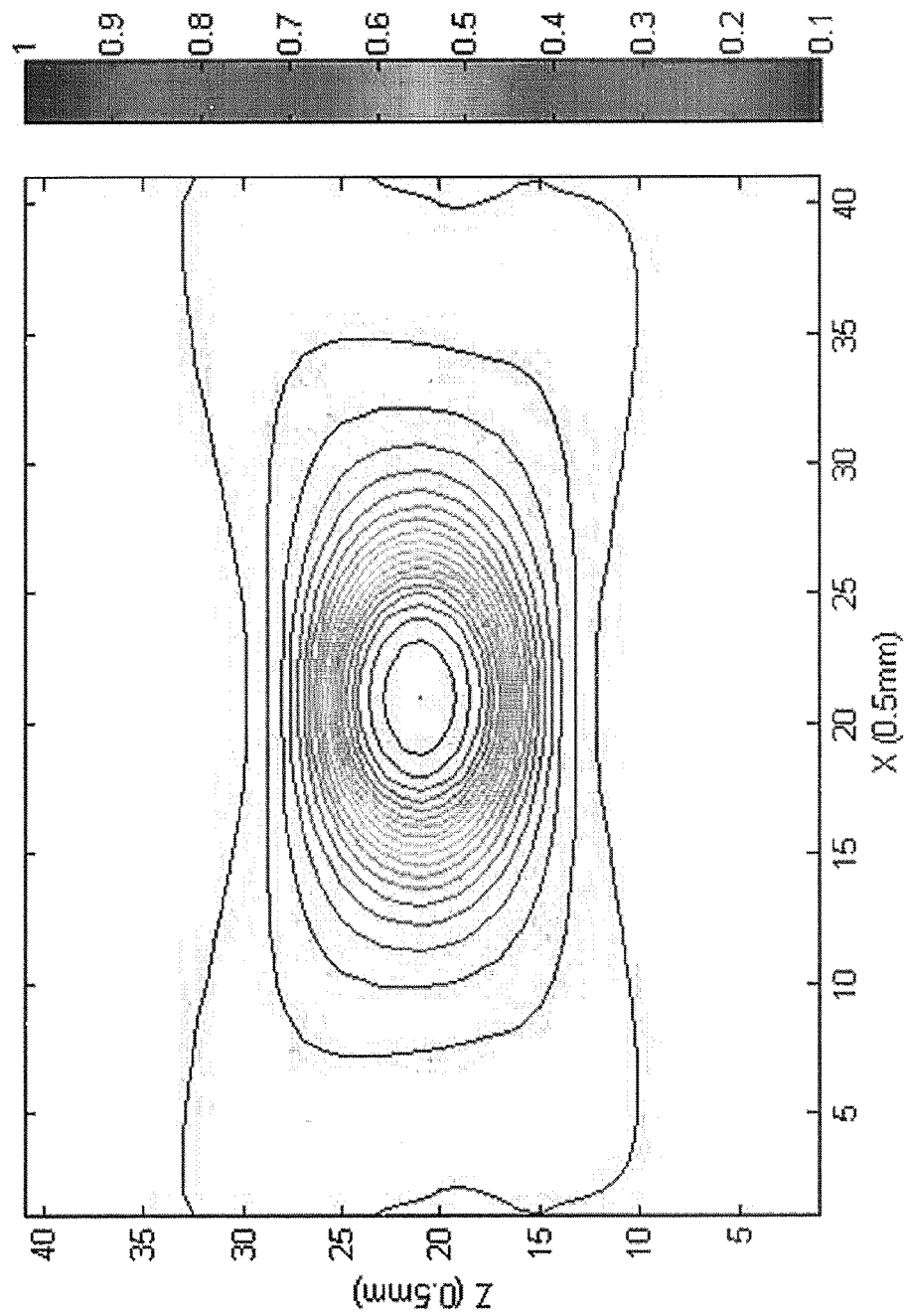

FIG. 12(a) illustrates a latitude angular range of 1° to 50°. FIG. 12(b) illustrates a latitude angular range of 5° to 55°. FIG. 12(c) illustrates a latitude angular range of 10° to 60°. FIG. 12(d) illustrates the Gamma Knife® 4 mm kernel. The plots shown contain isodose lines from 5% to 100% with 5% steps. As $\phi_1$ increases, the isodose distributions in the XZ plane become more and more irregular at low dose levels in comparison to that of the Gamma Knife® kernels. The impact of the error function (ERFC) sharpness parameter on DPP kernels is also considered as discussed below.

The Off Center Ratio (OCR) curve is fitted using function f=0.5*(erfc(a(x−b))+erfc(a(x+b))), where erfc(x) is defined as:

$$\text{erfc}(x) = \frac{2}{\sqrt{\pi}} \int_x^\infty e^{-t^2}\, dt.$$

Figure 13A:
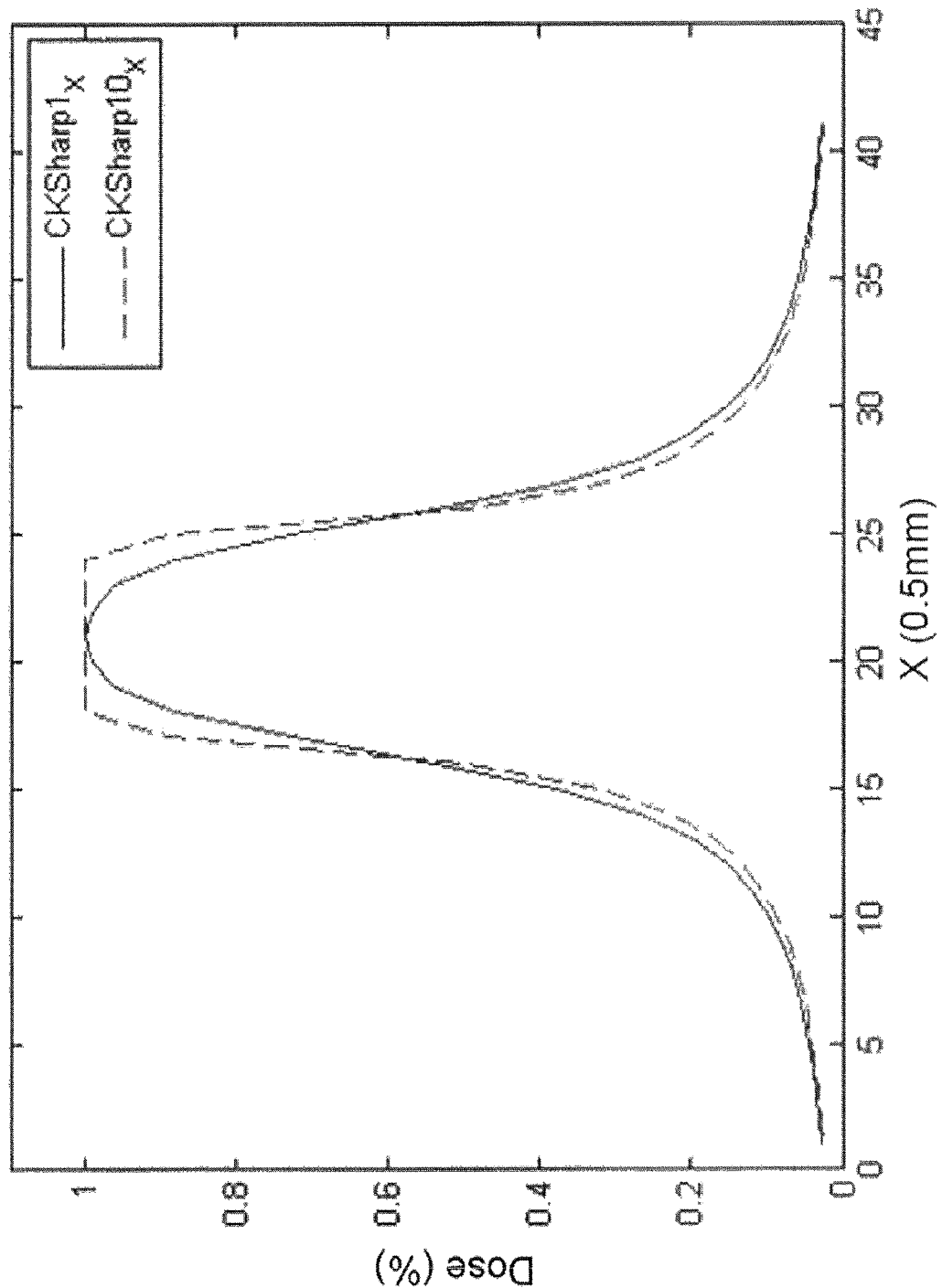
FIGS. 13(a)-(b) illustrate the impact of complementary error function (ERFC) parameter on the dose gradient of DPP kernels according to the present invention.
Figure 13B:
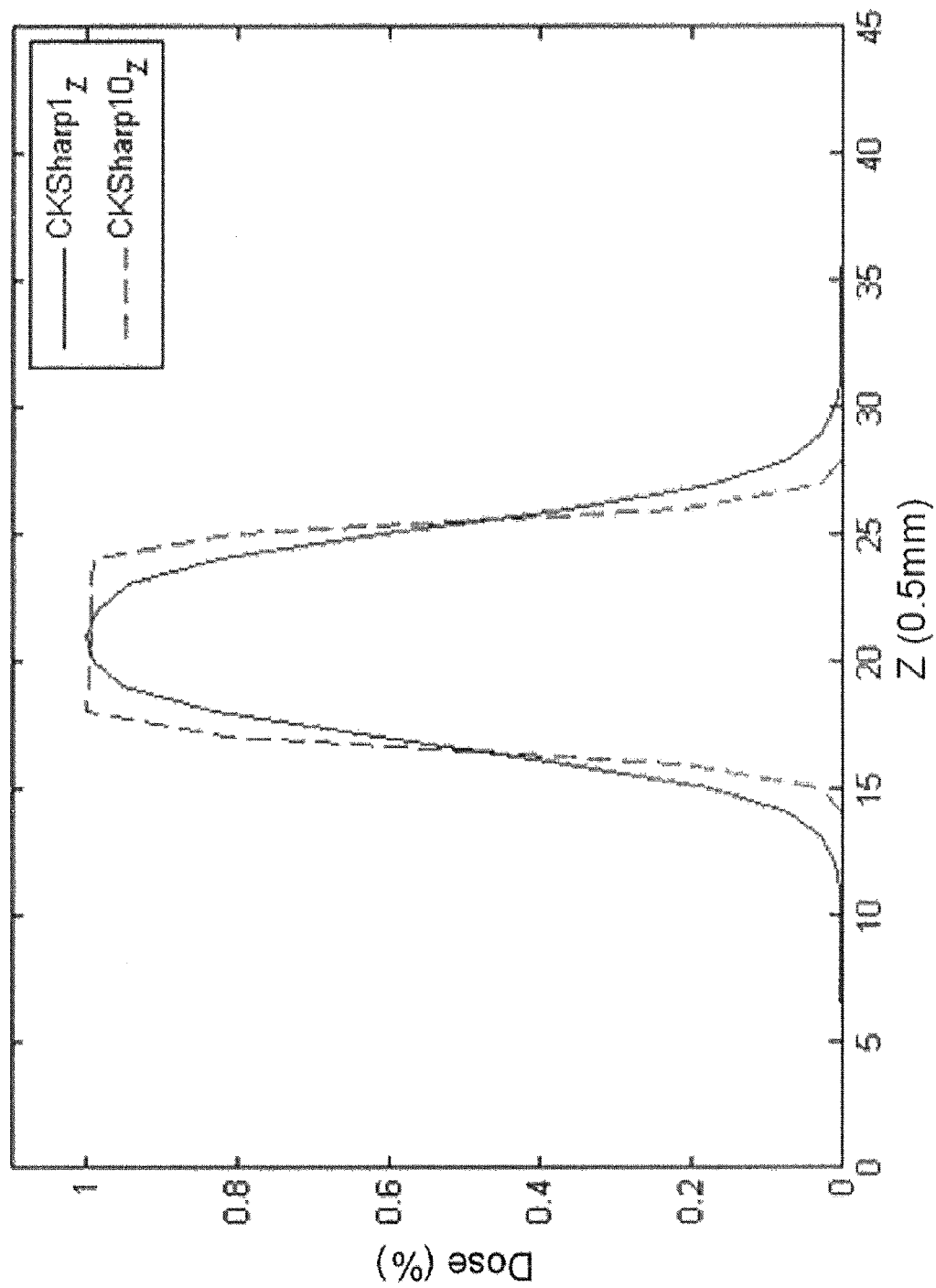
Figure 14A:
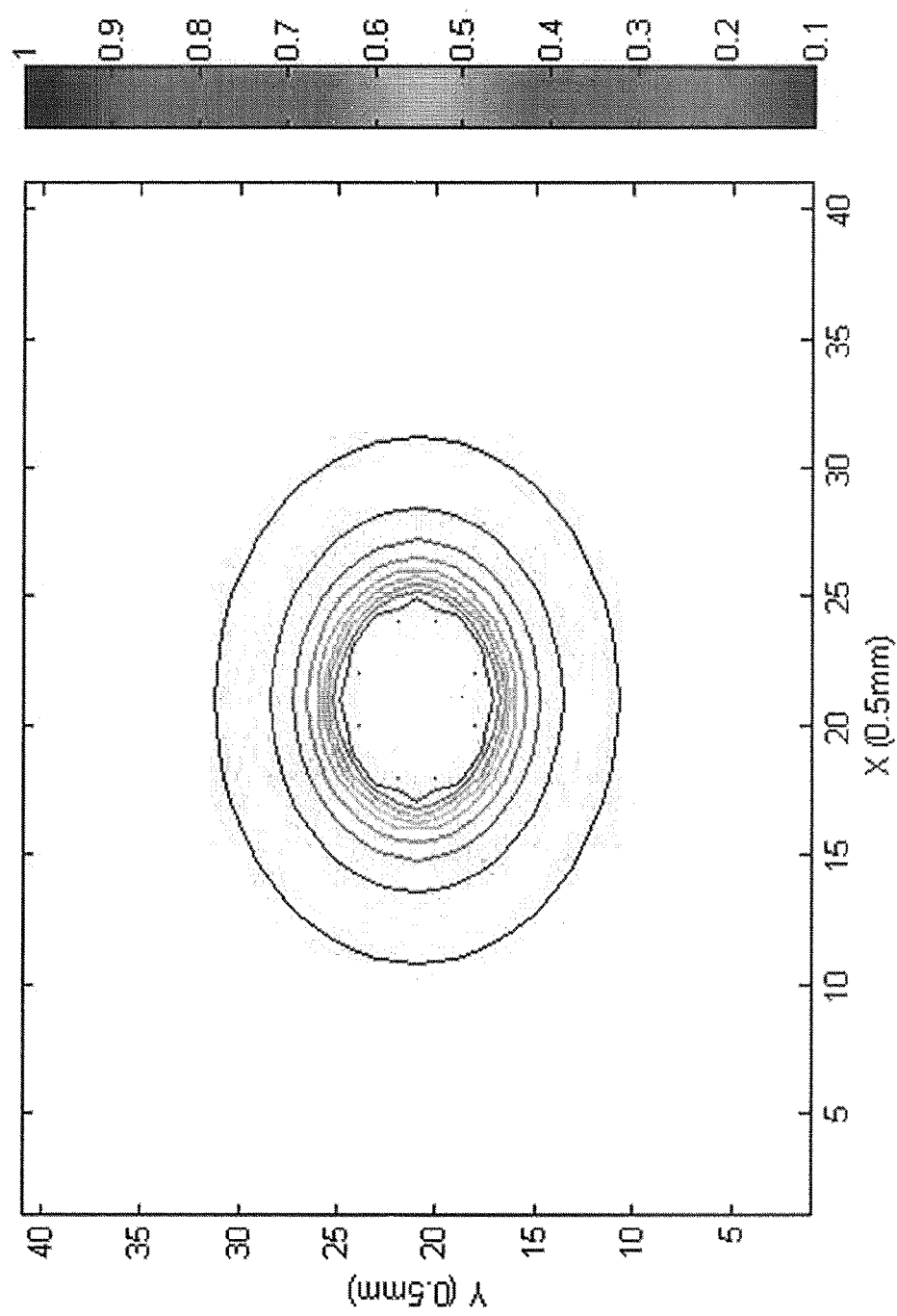
FIGS. 14(a)-(d) illustrate the isodose distributions of DPP kernels of different ERFC parameters according to the present invention.
Figure 14B:
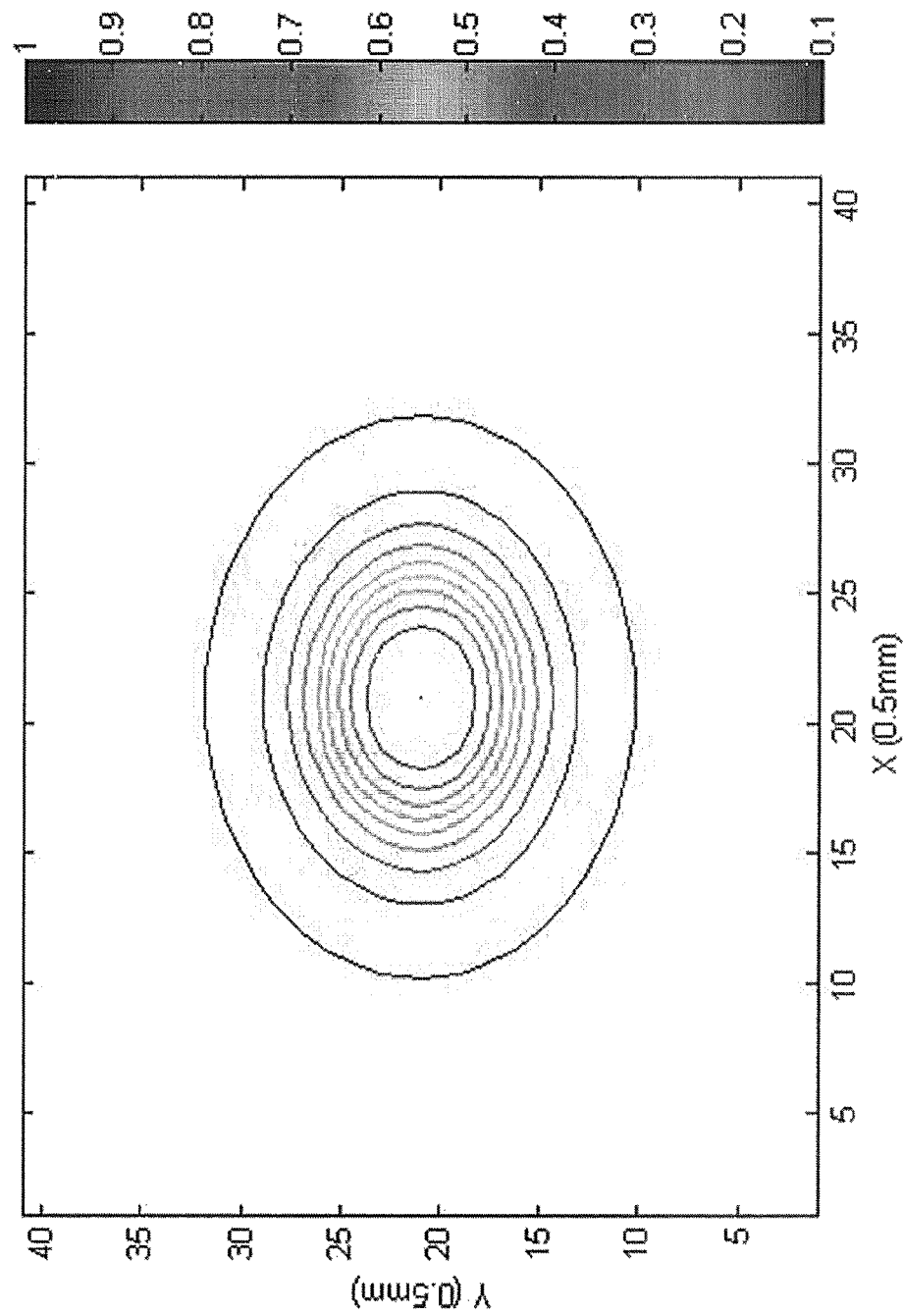
Figure 14C:
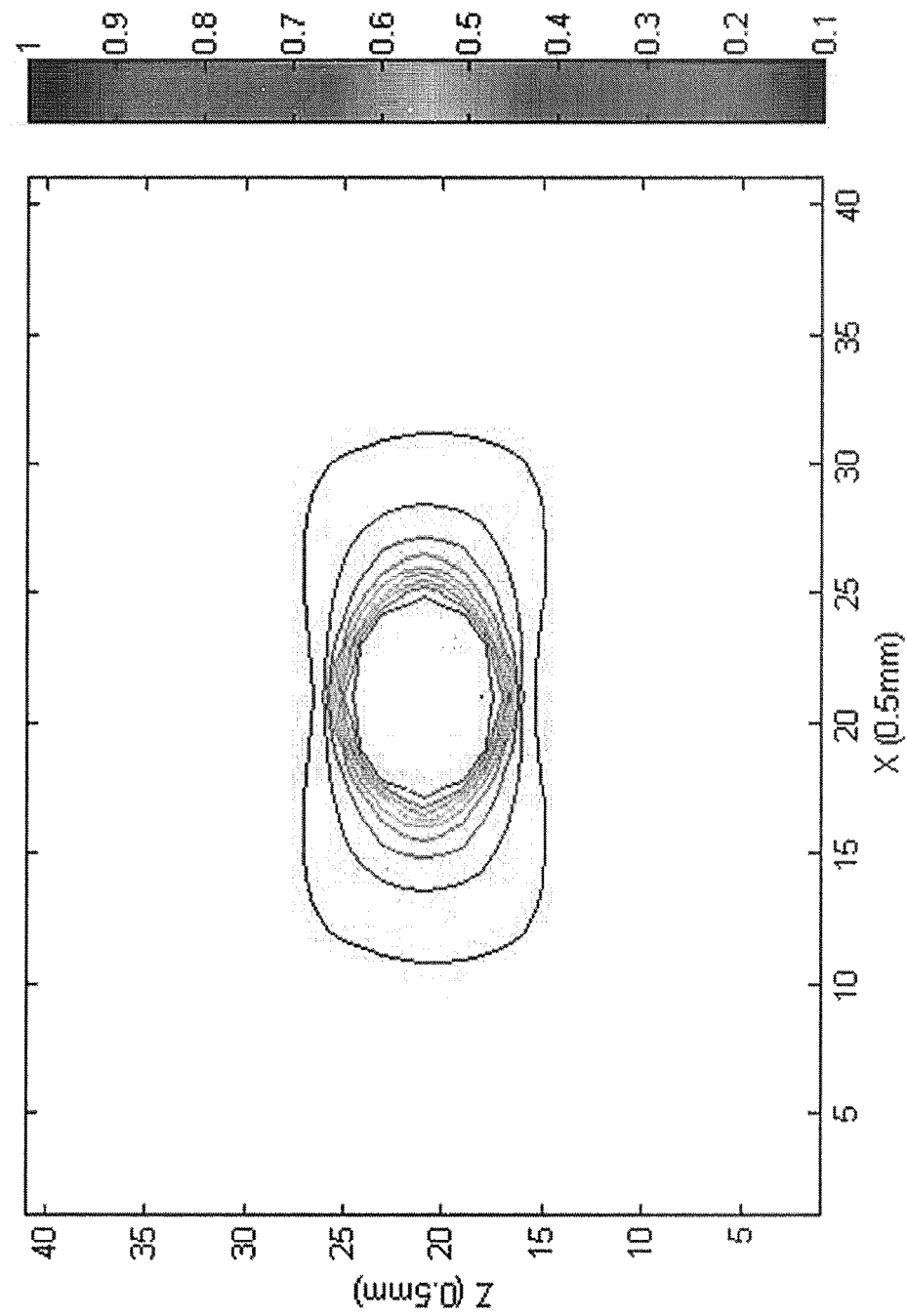
Figure 14D:
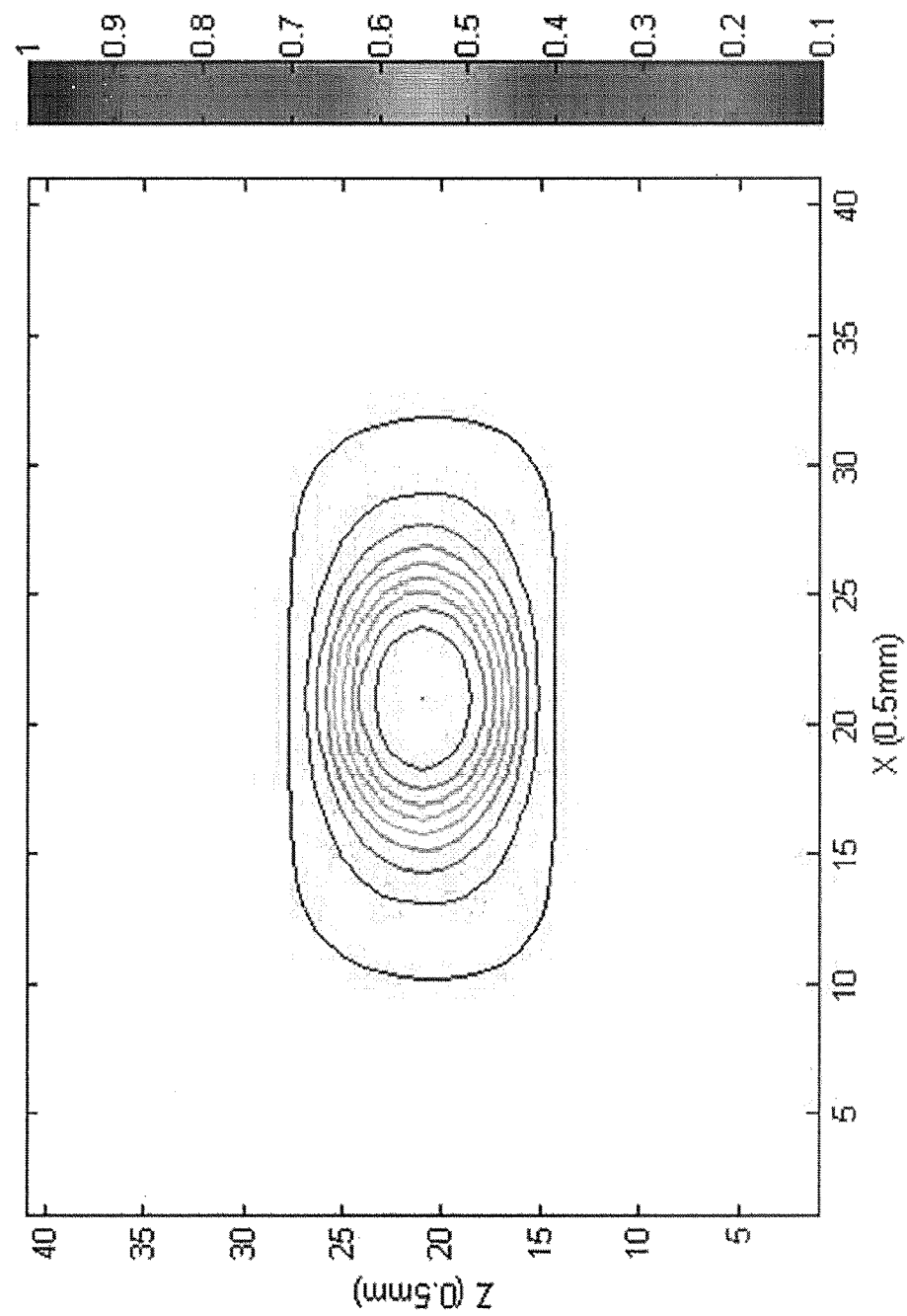
Figure 15:
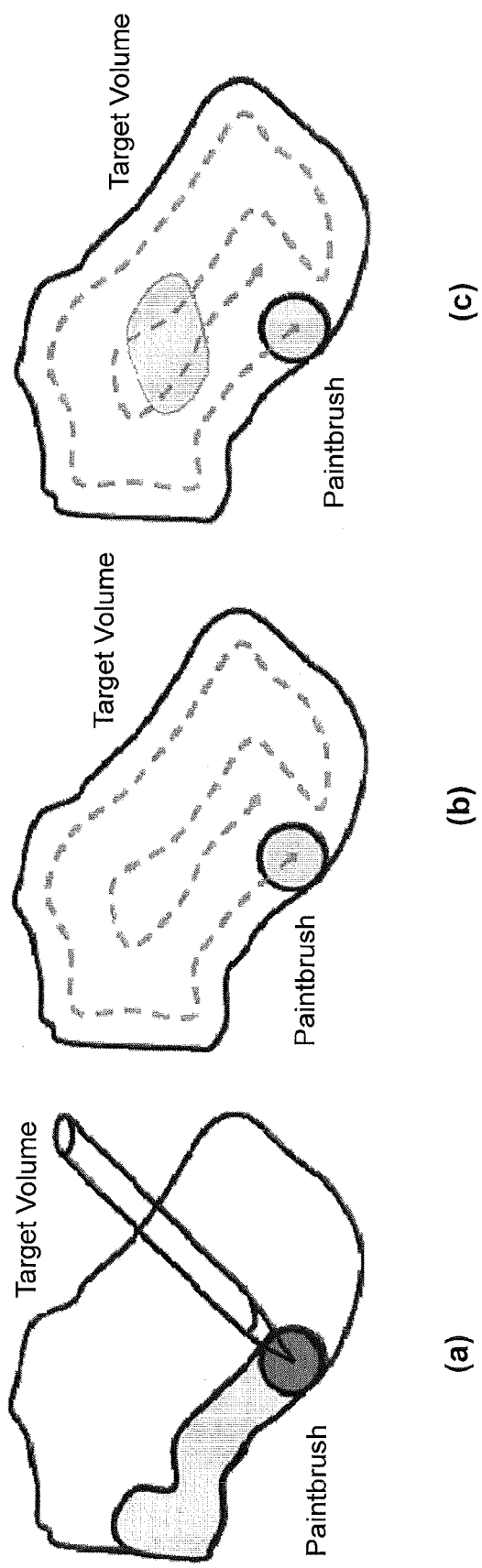
FIGS. 15(a)-(c) illustrate treatment planning of painting a three-dimensional (3D) tumor volume with a spherical "paintbrush" according to the present invention.

Mathematically, the parameter "a" reflects the sharpness, while "b" represents the width or radius of the field. FIGS. 13(a)-(b) show the comparison of dose profiles with a=1 and a=10. Specifically, FIG. 13(a) illustrates the profile comparison in the XY plane. FIG. 13(b) illustrates the profile comparisons in the XZ plane. FIGS. 14(a-d) show the isodose comparison of DPP kernels with different ERFC parameters. Specifically, FIG. 14(a) illustrates the isodose distributions of the DPP kernel with a=10 in the XY plane. FIG. 14(b) illustrates the isodose distributions of the DPP kernel with a=1 in the XY plane. FIG. 14(c) illustrates the isodose distributions of the DPP kernel with a=10 in the XZ plane. FIG. 14(d) illustrates the isodose distributions of the DPP kernel with a=1 in the XZ plane. The plots shown contain isodose lines from 10% to 100% with 10% steps. As can be seen from these figures, the dose falloff rate increases as "a" increases.

To demonstrate the advantage of DPP approach, the DPP kernels are replaced with the Gamma Knife® kernels and the resulting radiation dose distributions are compared. Gamma Knife® has long been consider the "gold standard" of various radiosurgery modalities. Since the DPP approach can outperform Gamma Knife®, the DPP approach is advancing the state of the art.

Figure 16:
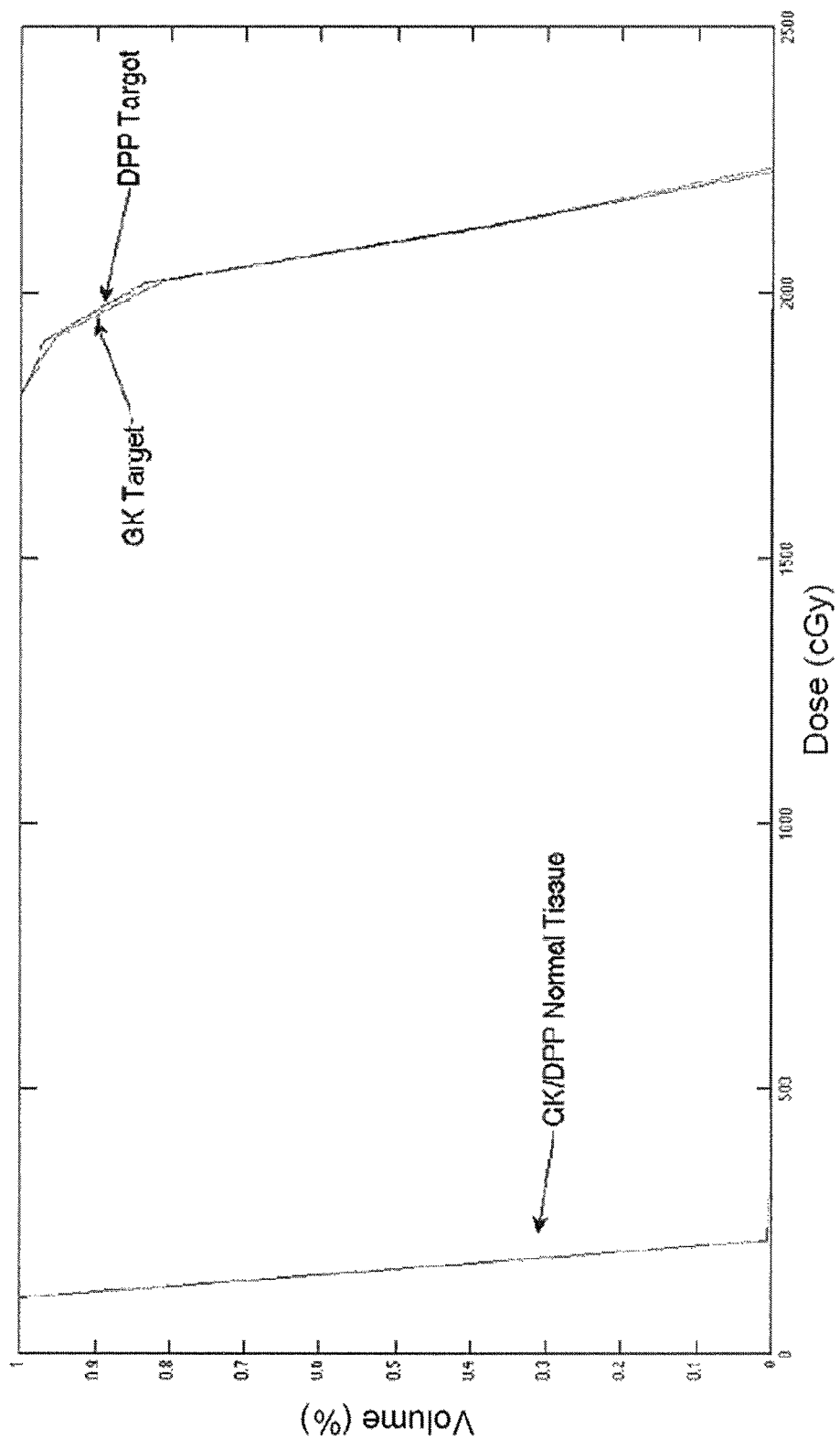
FIG. 16 illustrates comparisons of dose-volume histograms (DVH) according to the present invention.

Two examples comparing the treatment planning result when using DPP kernels versus Gamma Knife® kernels are now discussed. In the first embodiment, a 3D spherical phantom is used with a 80 mm radius and a spherical tumor with a 7.5 mm radius at the center. Both optimizations ran with identical parameters. To ensure that the best possible Gamma Knife® plan is obtained, only 4 mm shots were used in the planning phase. The current Gamma Knife® system can produce kernels ranging from 4 mm to 16 mm, with the 4 mm kernel being the sharpest kernel. FIG. 16 shows the DVH comparisons. FIGS. 17(a)-(b) and FIGS. 18(a)-(d) show the comparisons between dose profiles and isodose distributions.

Figure 17A:
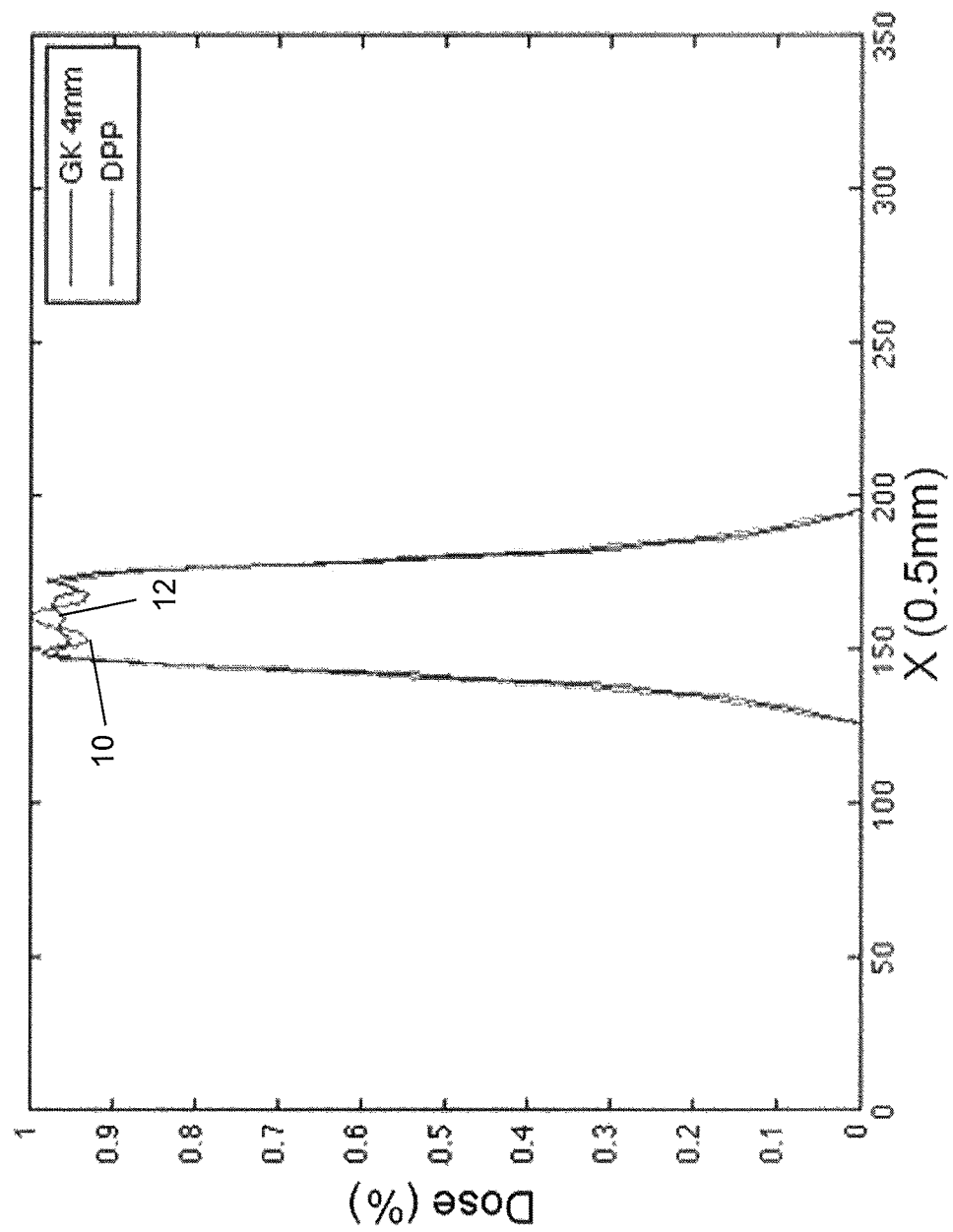
FIGS. 17(a)-(b) illustrate dose profile comparisons between a DPP plan and a Gamma Knife® plan according to the present invention.
Figure 17B:
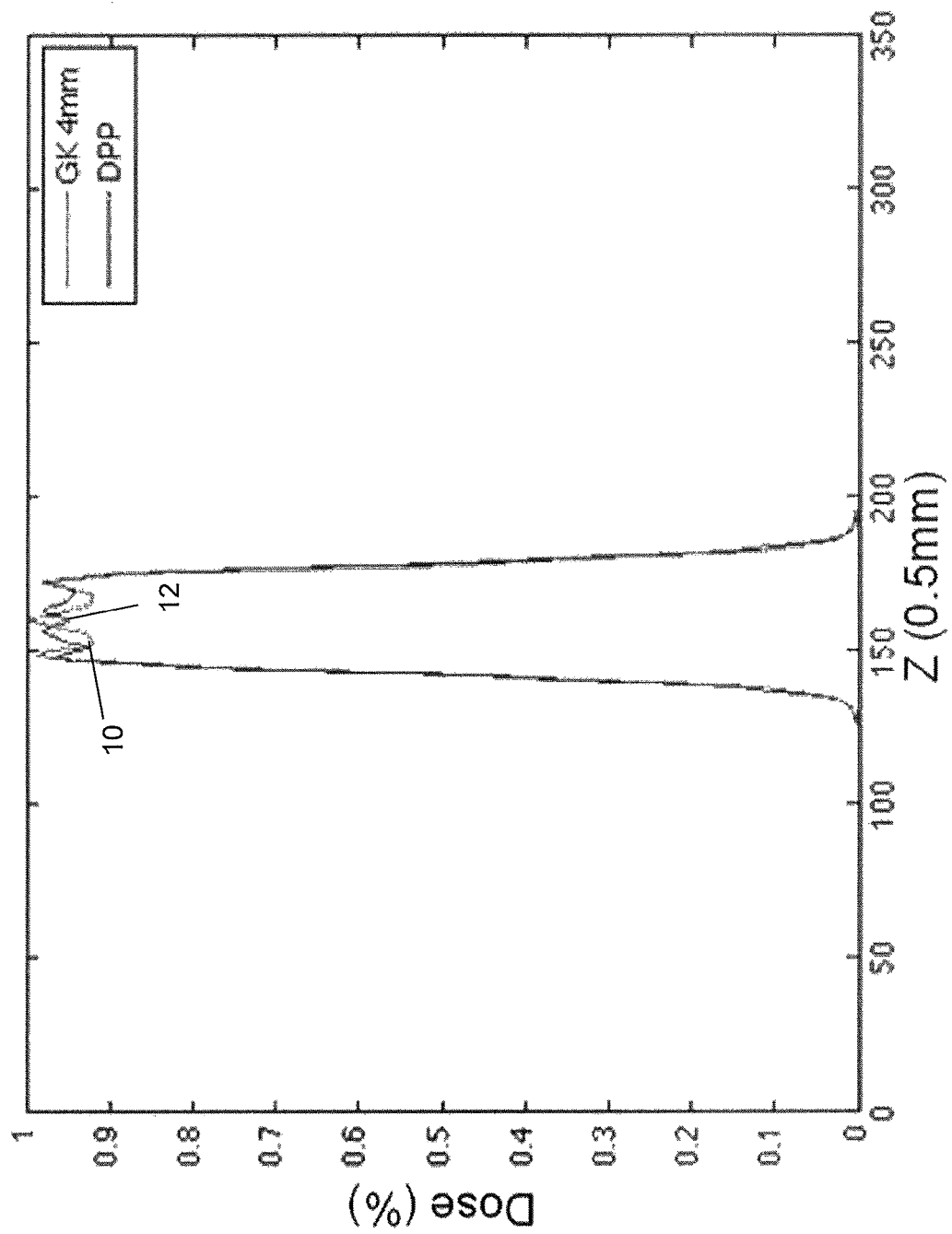
Figure 18A:
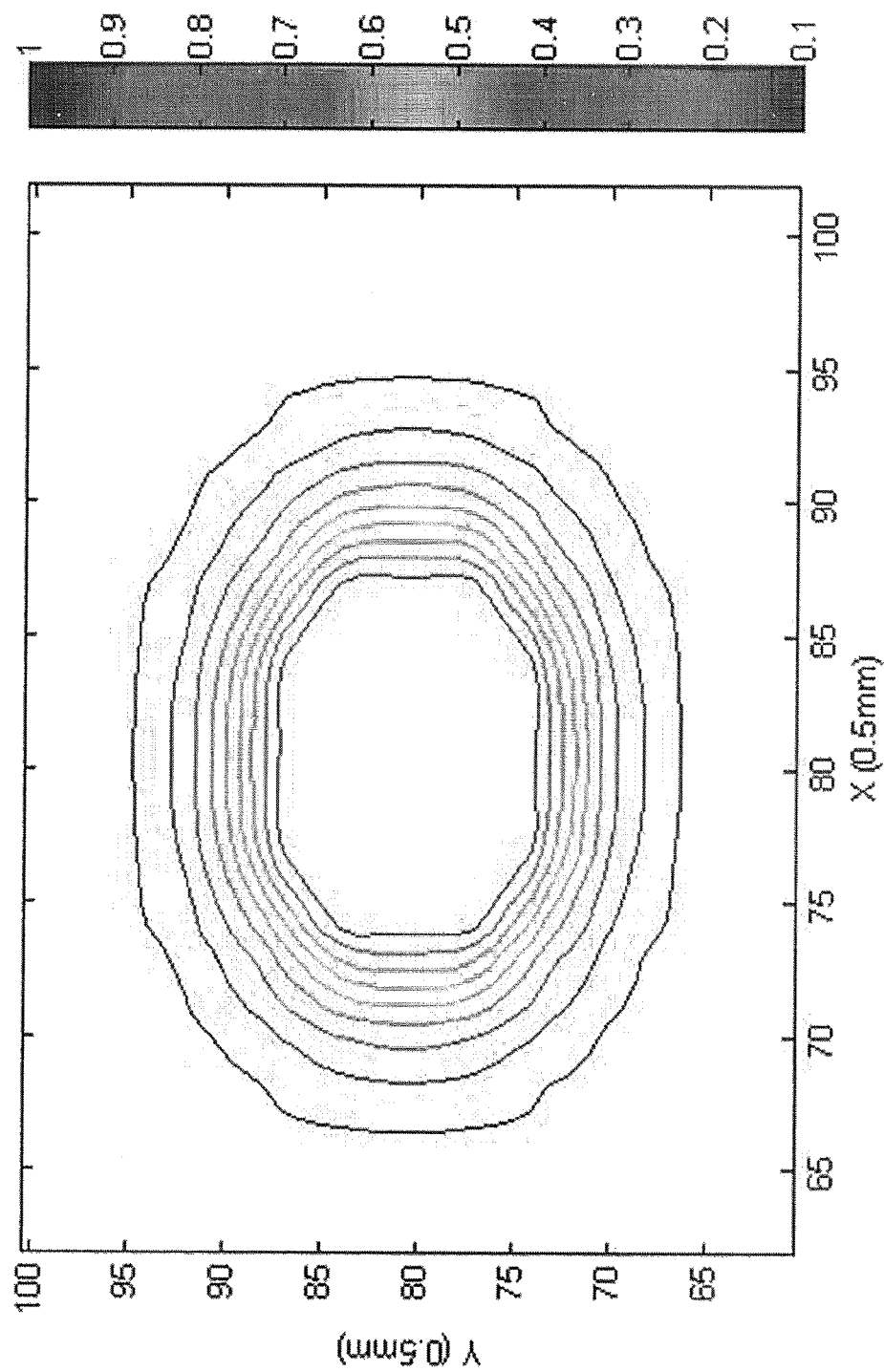
FIGS. 18(a)-(d) illustrate isodose comparisons between a DPP plan and a Gamma Knife® plan according to the present invention.
Figure 18B:
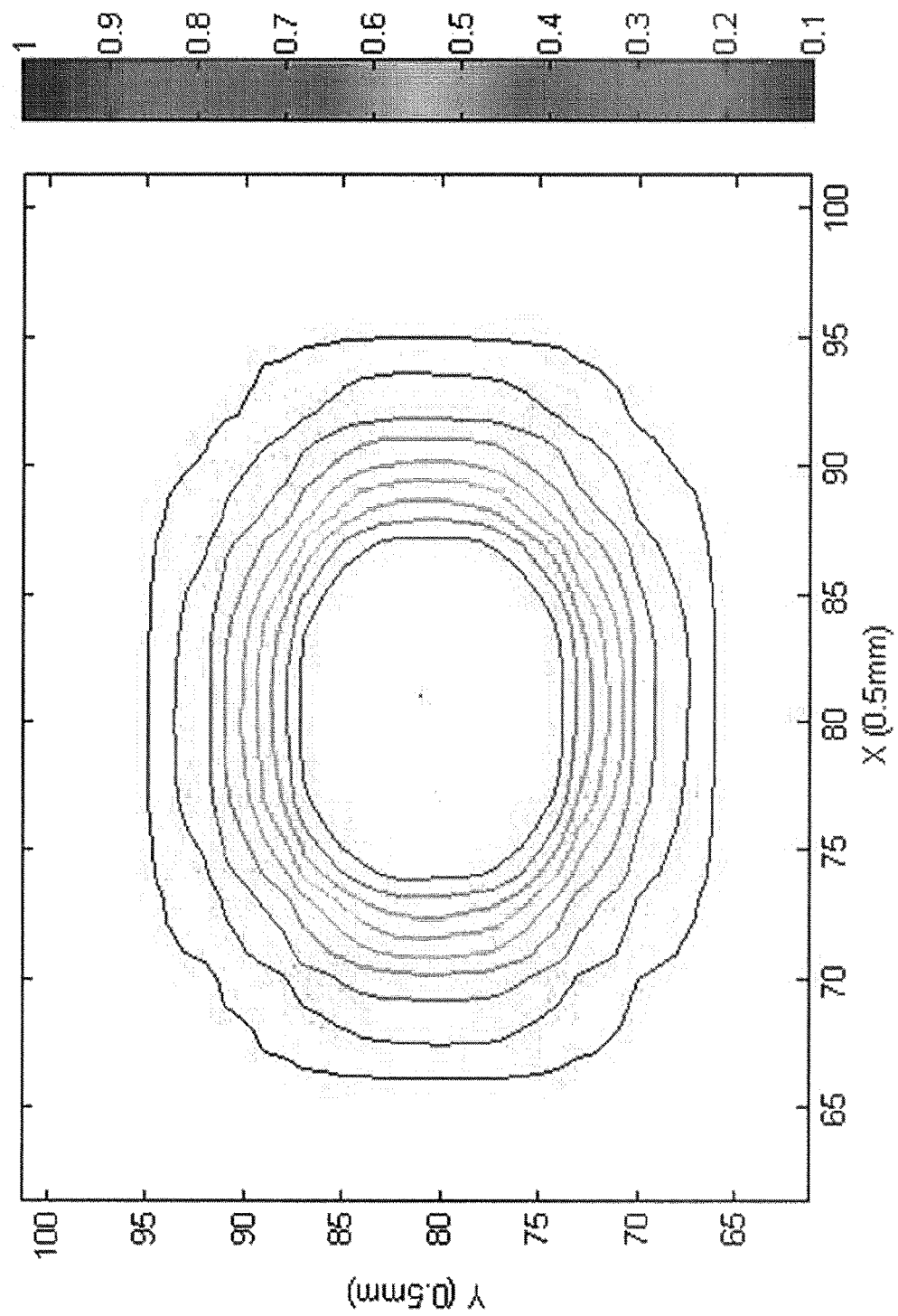
Figure 18C:
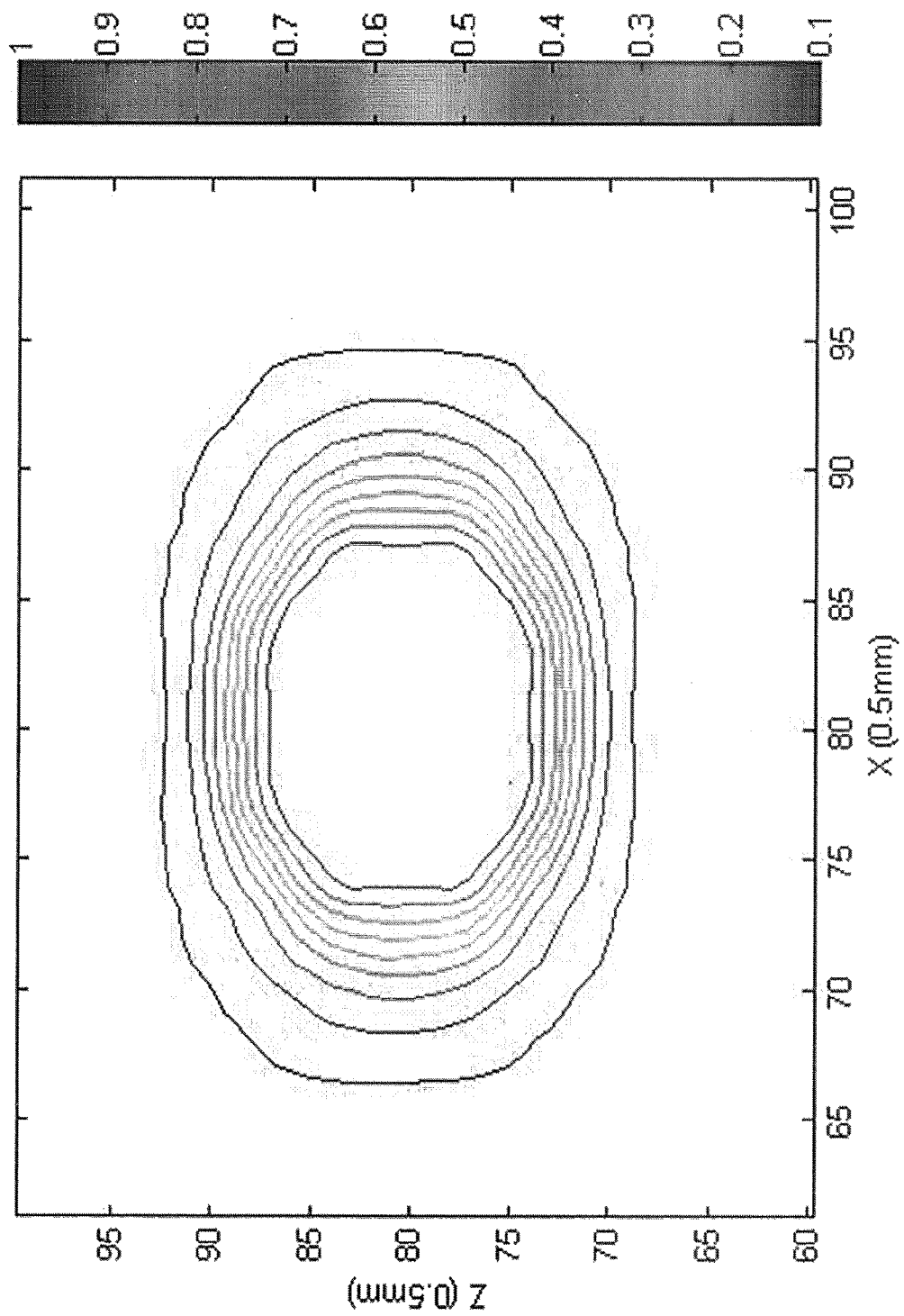
Figure 18D:
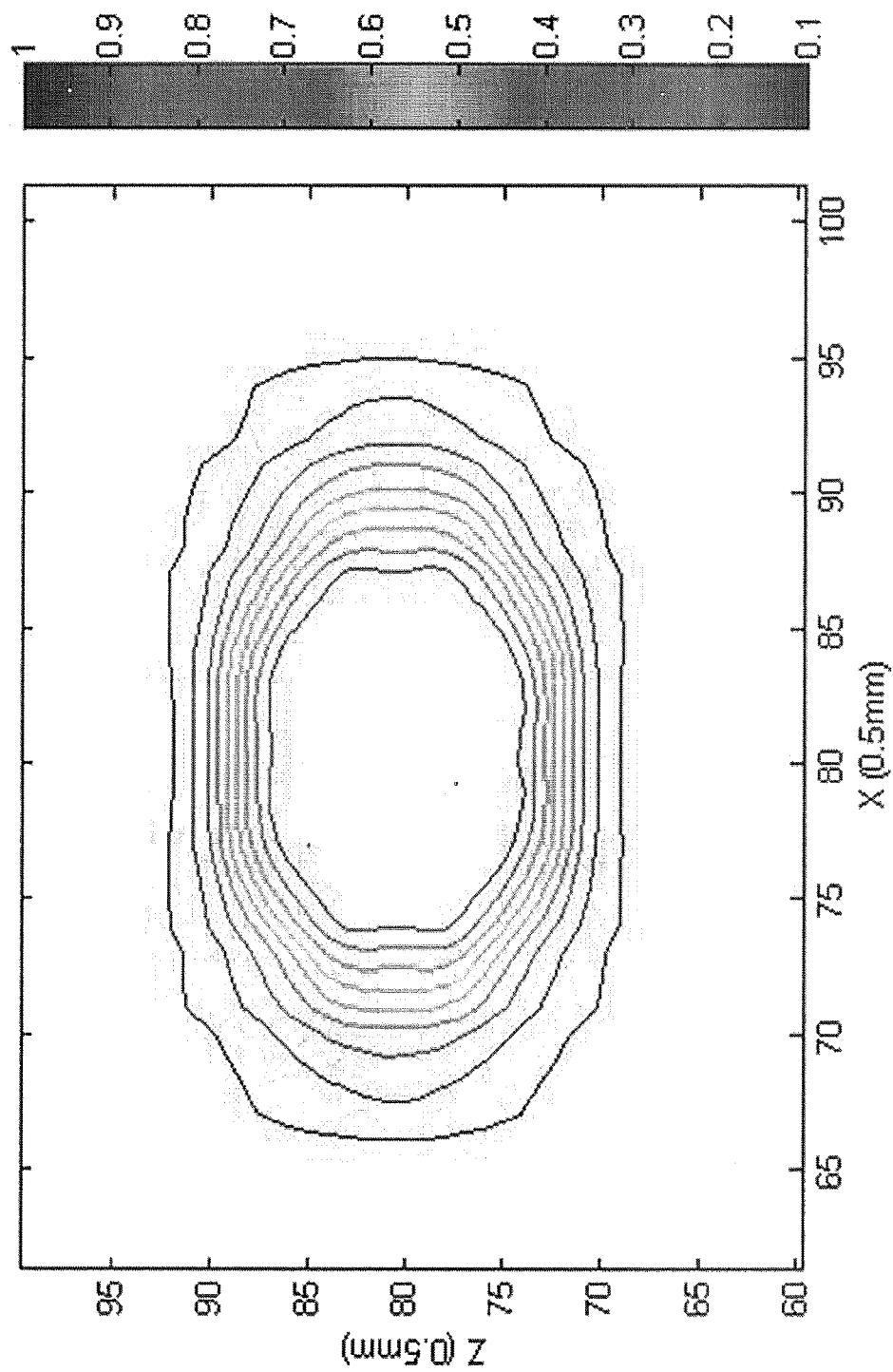

FIG. 17(a) illustrates the dose profiles in the XY plane with the DPP plan shown by line 10 and the Gamma Knife® plan shown by line 12. FIG. 17(b) illustrates the dose profiles in the XZ plane, again, with the DPP plan shown by line 10 and the Gamma Knife® plan shown by line 12. FIG. 18(a) illustrates the isodose distributions of the DPP plan in the XY plane. FIG. 18(b) illustrates the isodose distributions of the Gamma Knife® plan in the XY plane. FIG. 18(c) illustrates the isodose distributions of the DPP plan in the XZ plane. FIG. 18(d) illustrates the isodose distributions of the Gamma Knife® plan in the XZ plane. The plot shown contains isodose lines from 10% to 100% with 10% steps. As can be seen from these plots, the DPP plan and the Gamma Knife® plan are very similar with the DPP plans being slightly better and more uniform.

However, the precision of these comparisons is limited by the resolution of the Gamma Knife® kernels obtained from Zlekta at 5 mm. With such a sharp dose gradient, the numerical limit is approached. If these comparisons could be conducted at a much higher resolution, the sharper dose gradient of DPP plans of the present invention would be more pronounced.

Figure 19A:
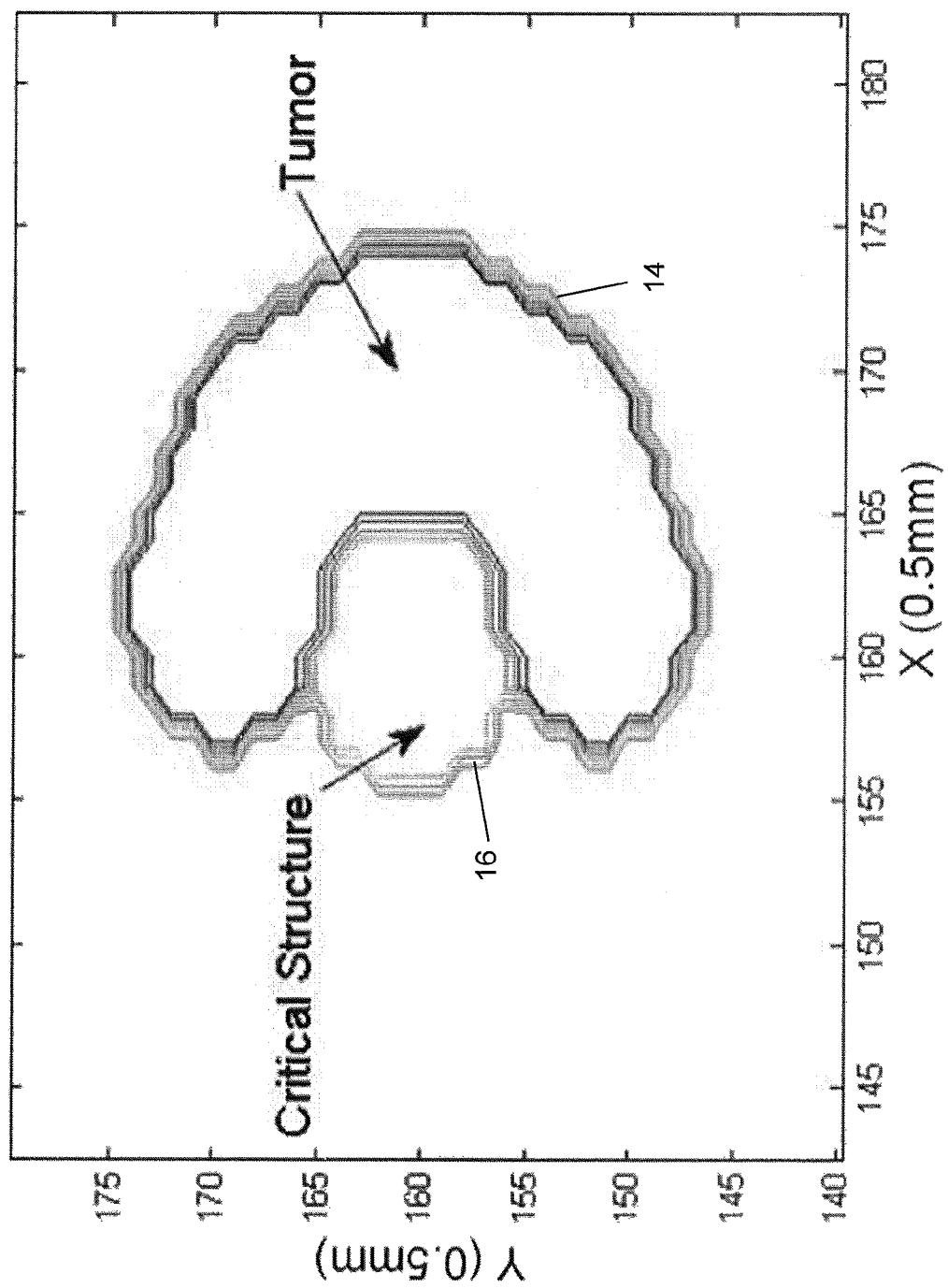
FIGS. 19(a)-(b) illustrate a plot of C-shaped tumor phantom according to the present invention.
Figure 19B:
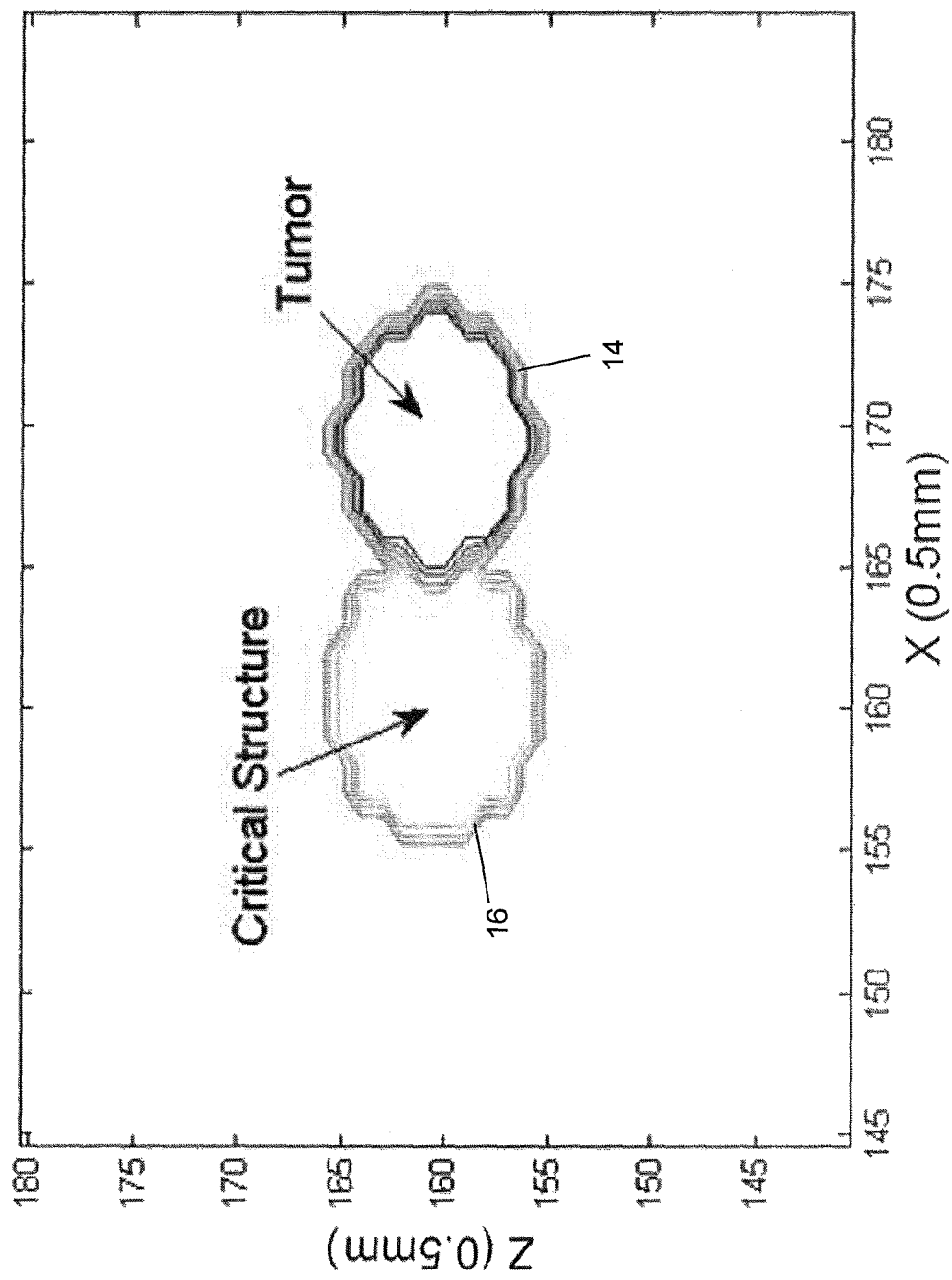

The DPP kernels and Gamma Knife® kernels are also considered for a more challenging phantom, which contains a C-shaped tumor surrounding a spherical critical structure as shown in FIGS. 19(a)-(b) with the line 14 defining the outer perimeter of the tumor, surrounding a spherical critical structure having an outer perimeter defined by line 16. Specifically, FIG. 19(a) illustrates the phantom in the XY plane and FIG. 19(b) illustrates the phantom in the XZ plane.

Figure 20:
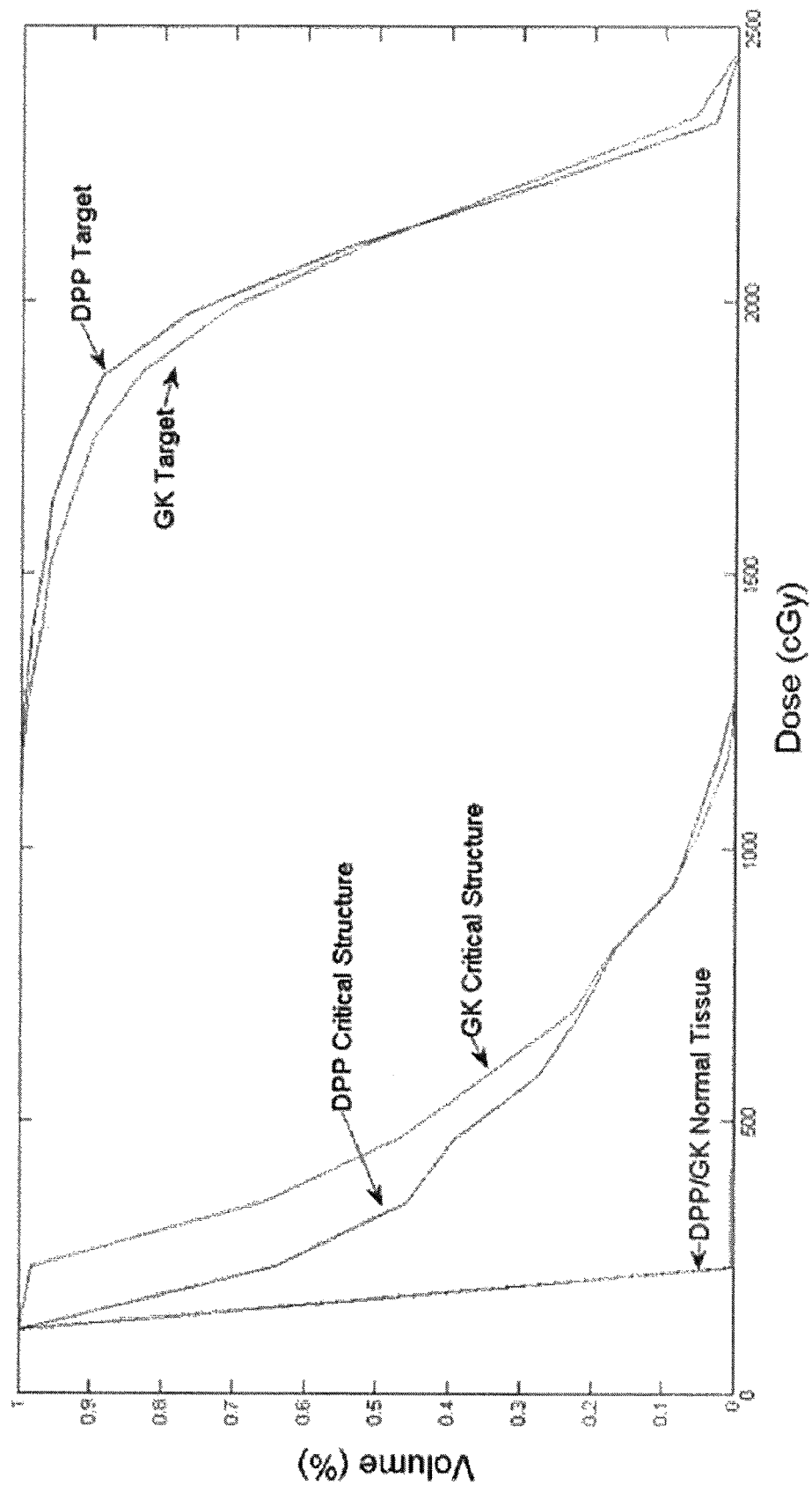
FIG. 20 illustrates comparisons of DVH according to the present invention.
Figure 21A:
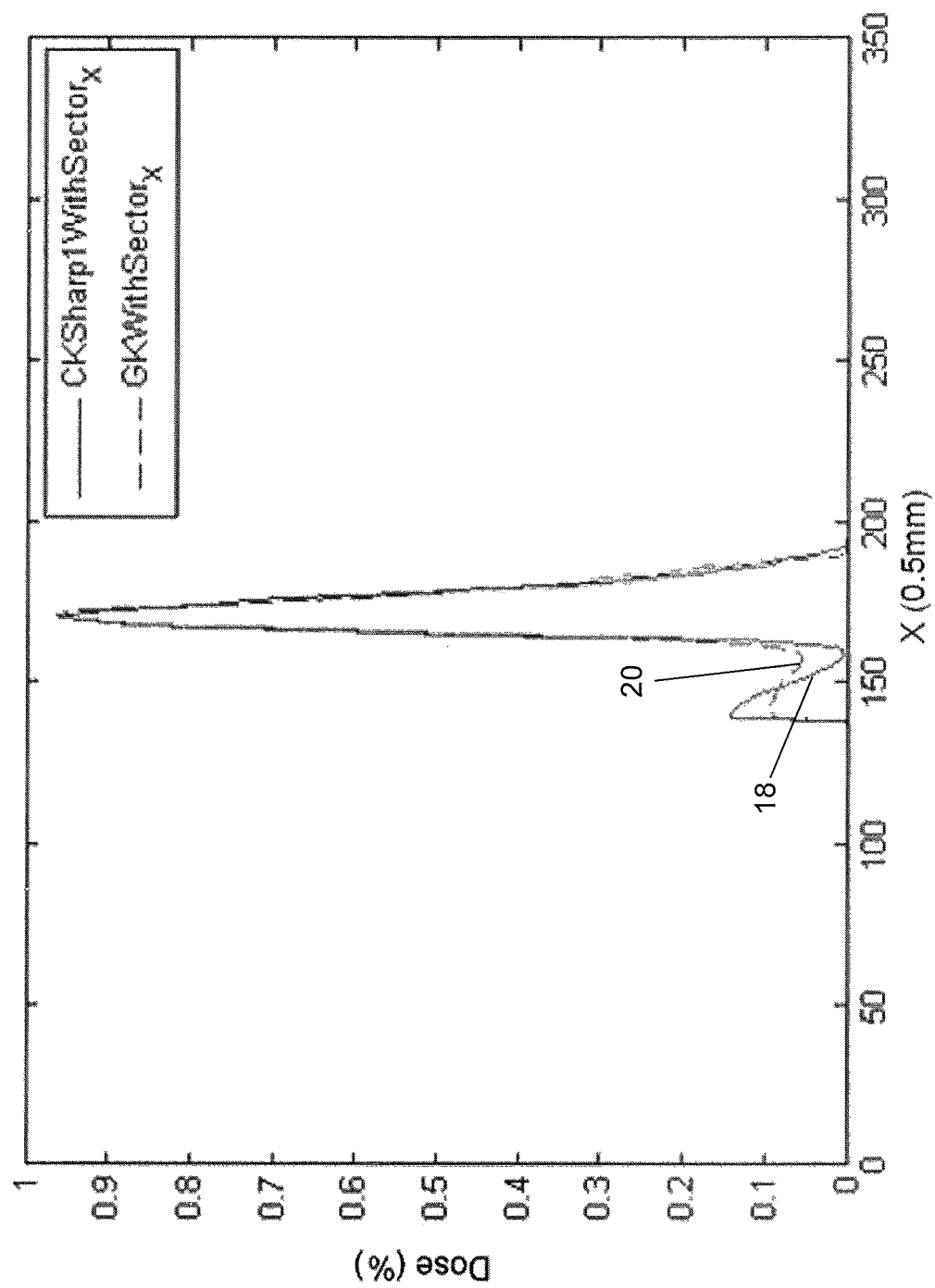
FIGS. 21(a)-(c) illustrate dose profile comparisons between a DPP plan and a Gamma Knife® plan according to the present invention.
Figure 21B:
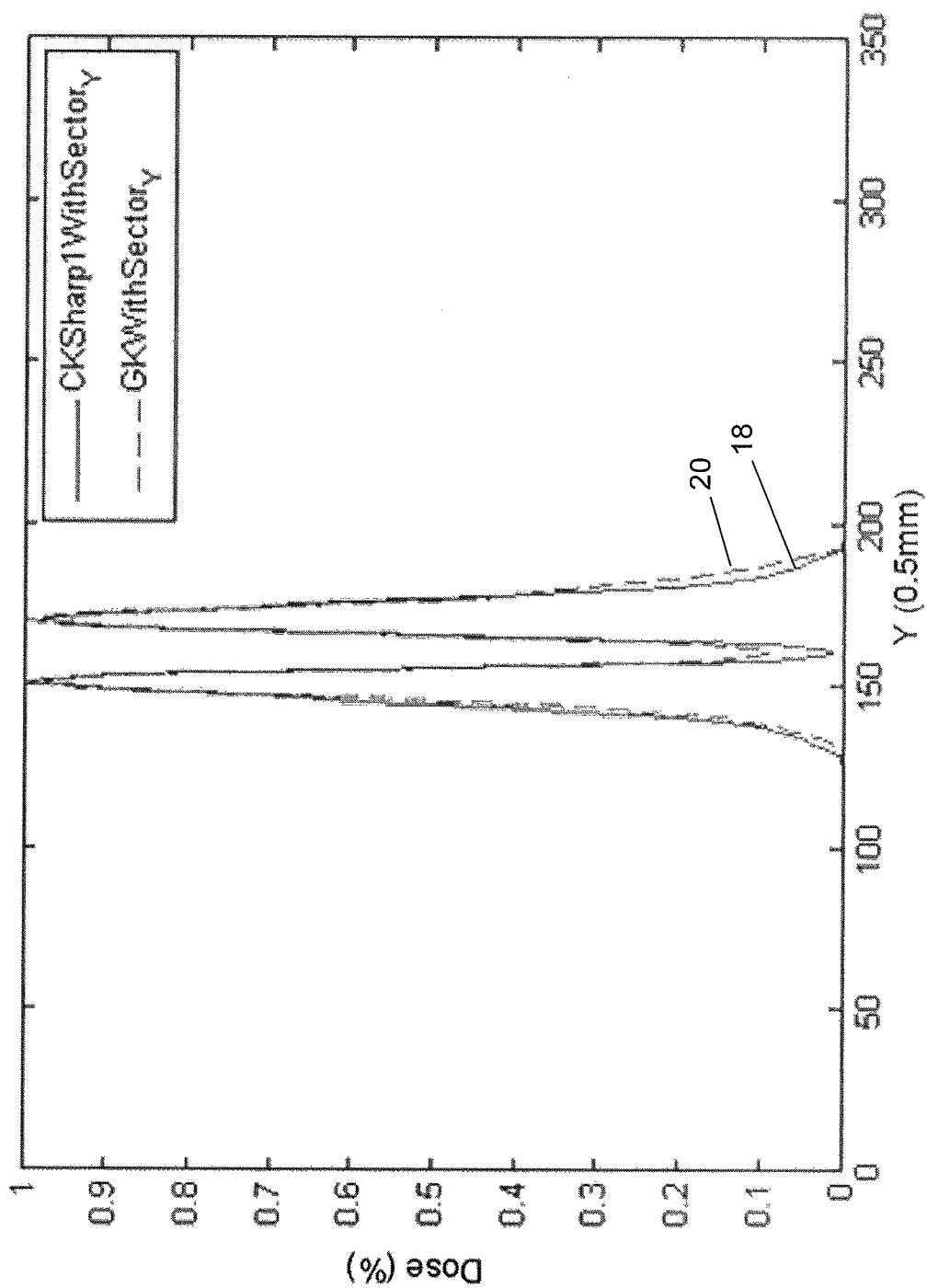
Figure 21C:
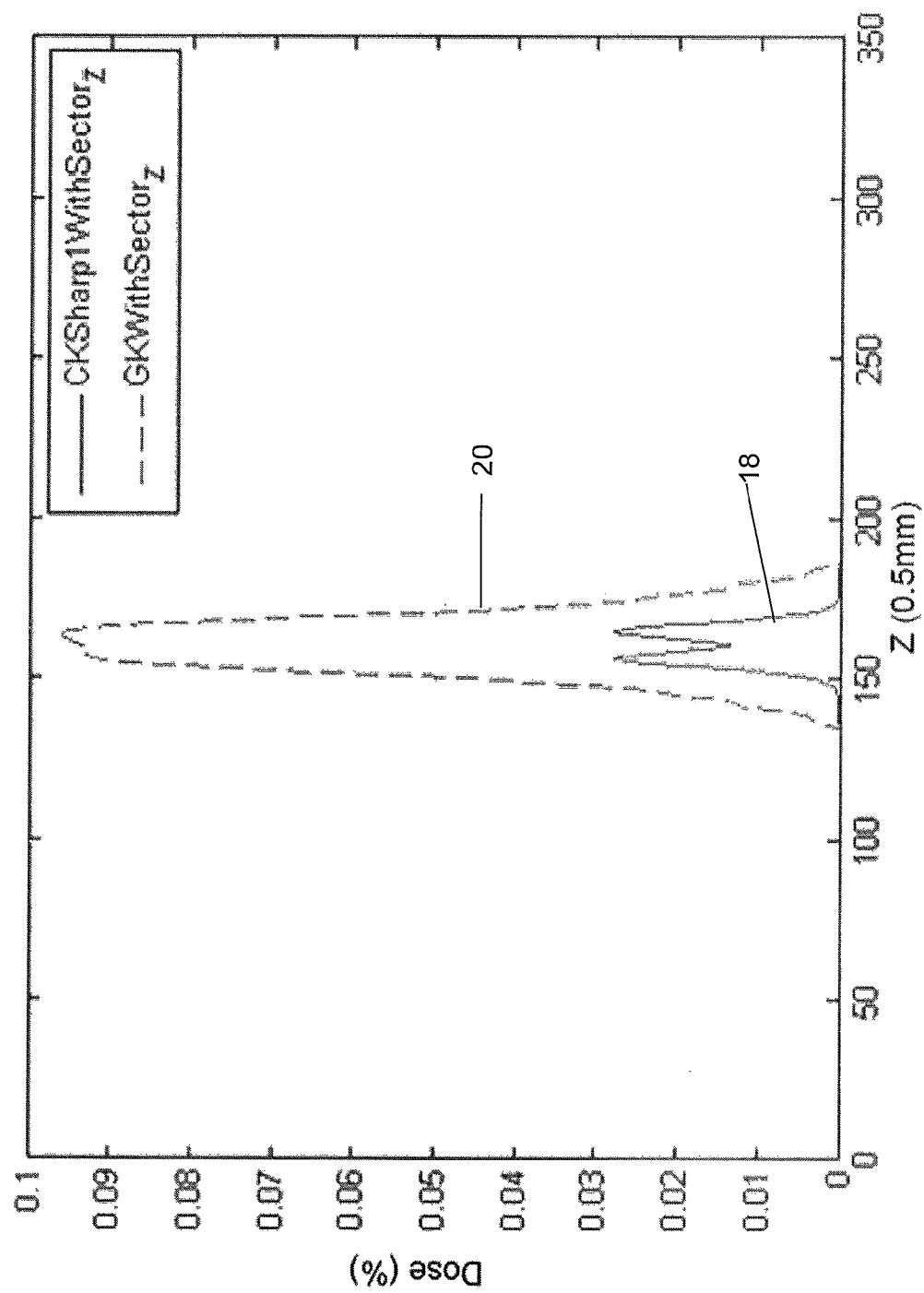
Figure 22:
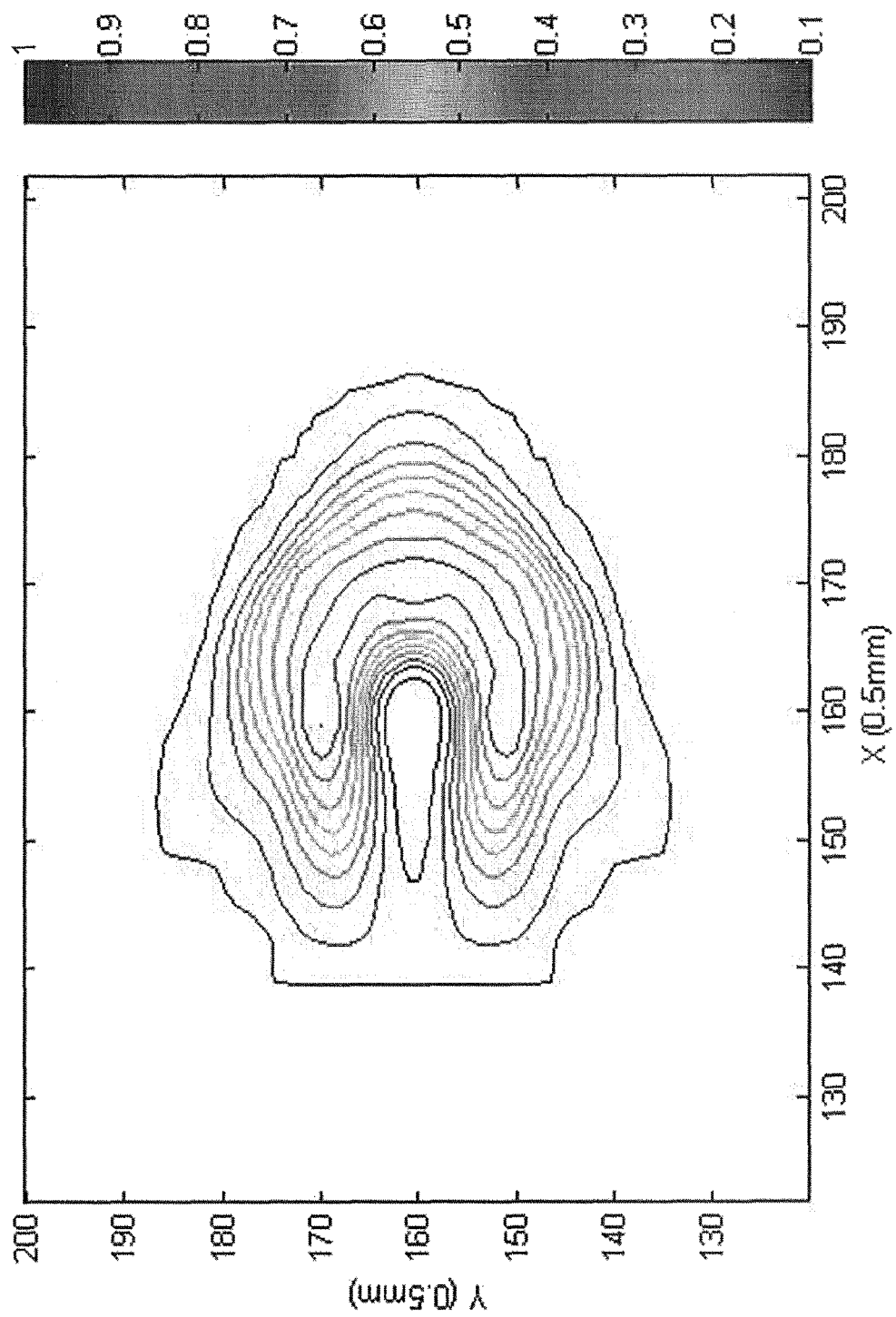
FIGS. 22(a)-(d) illustrates isodose comparisons between a DPP plan and a Gamma Knife® plan according to the present invention.
Figure 22:
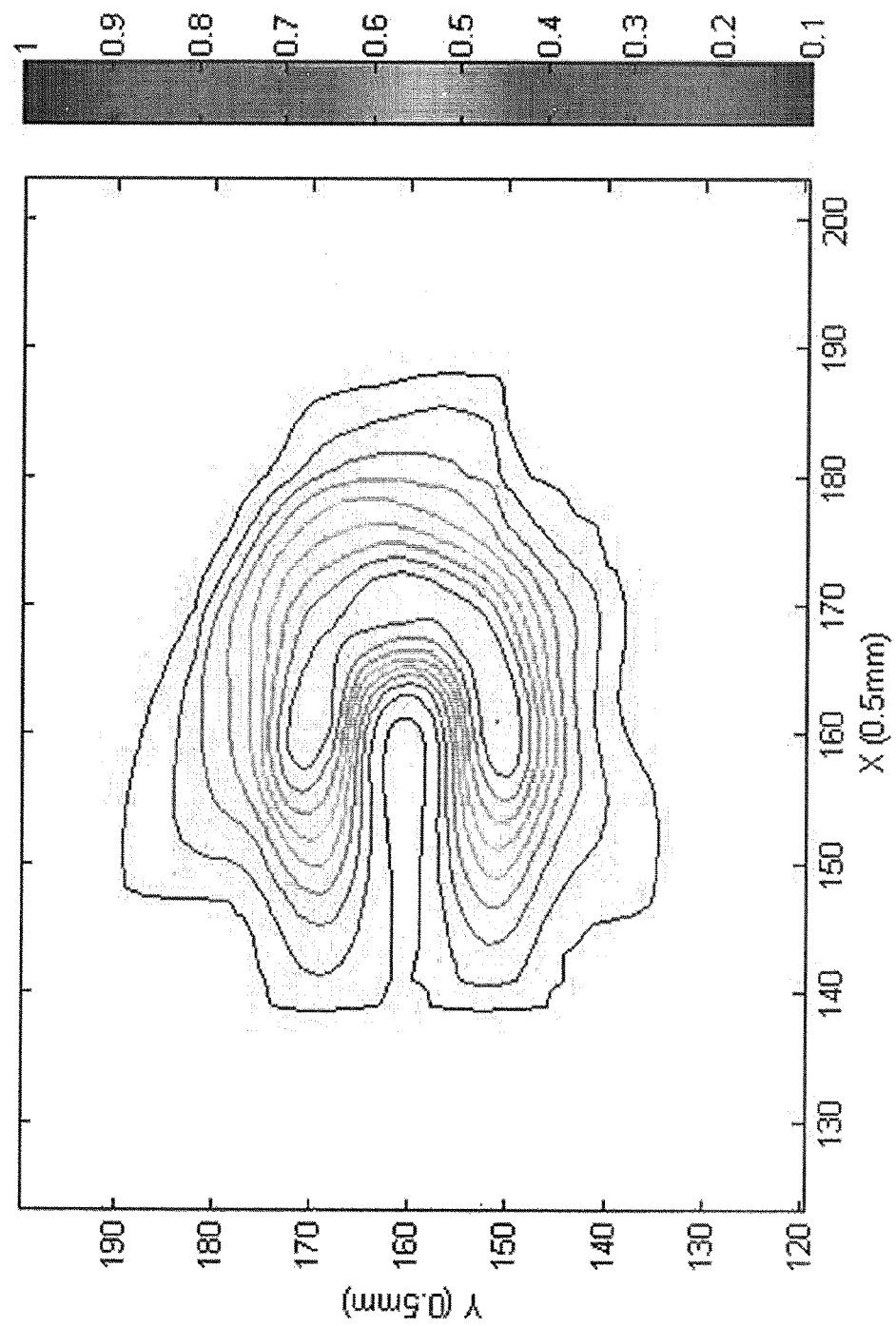
Figure 22:
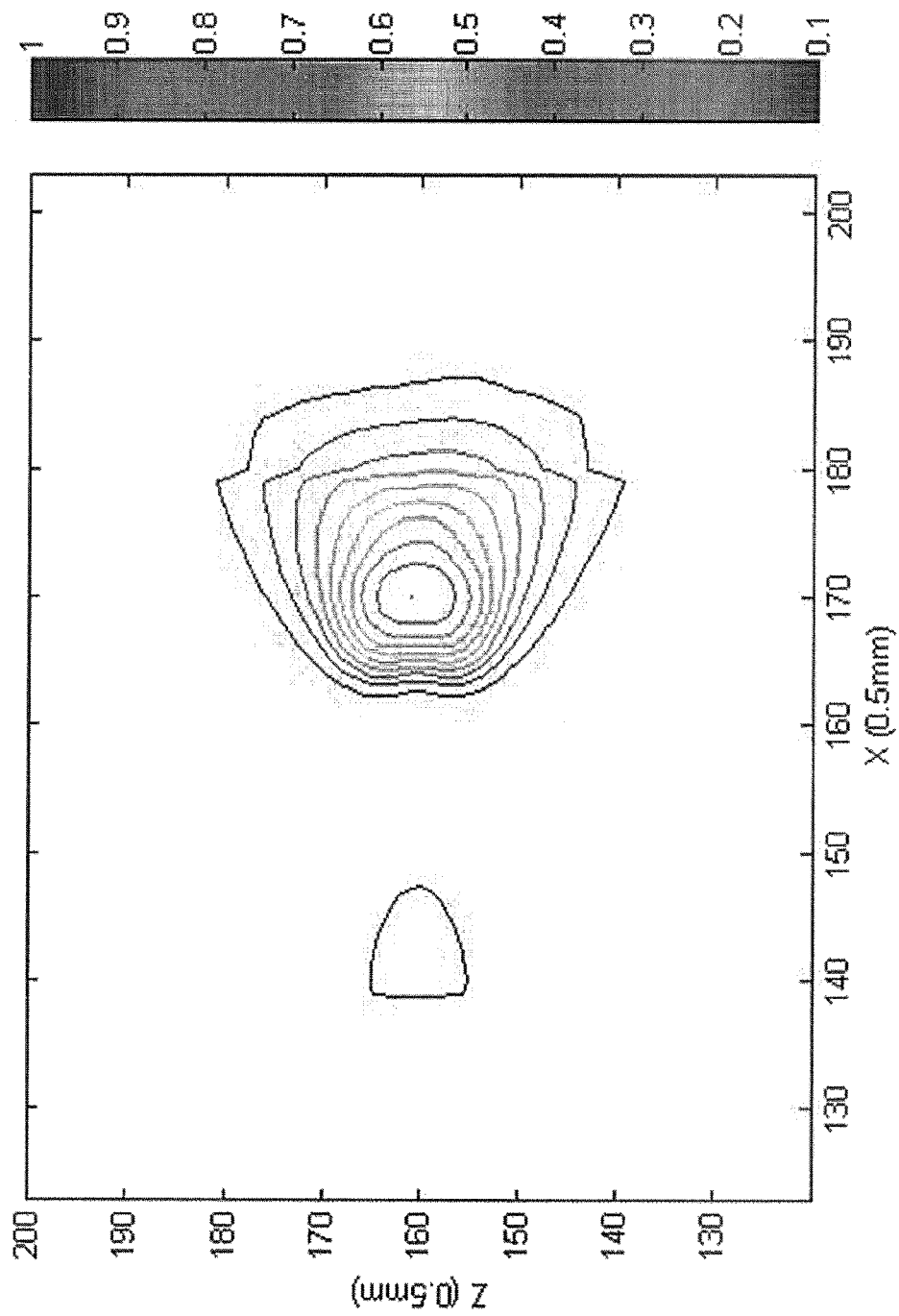
Figure 22:
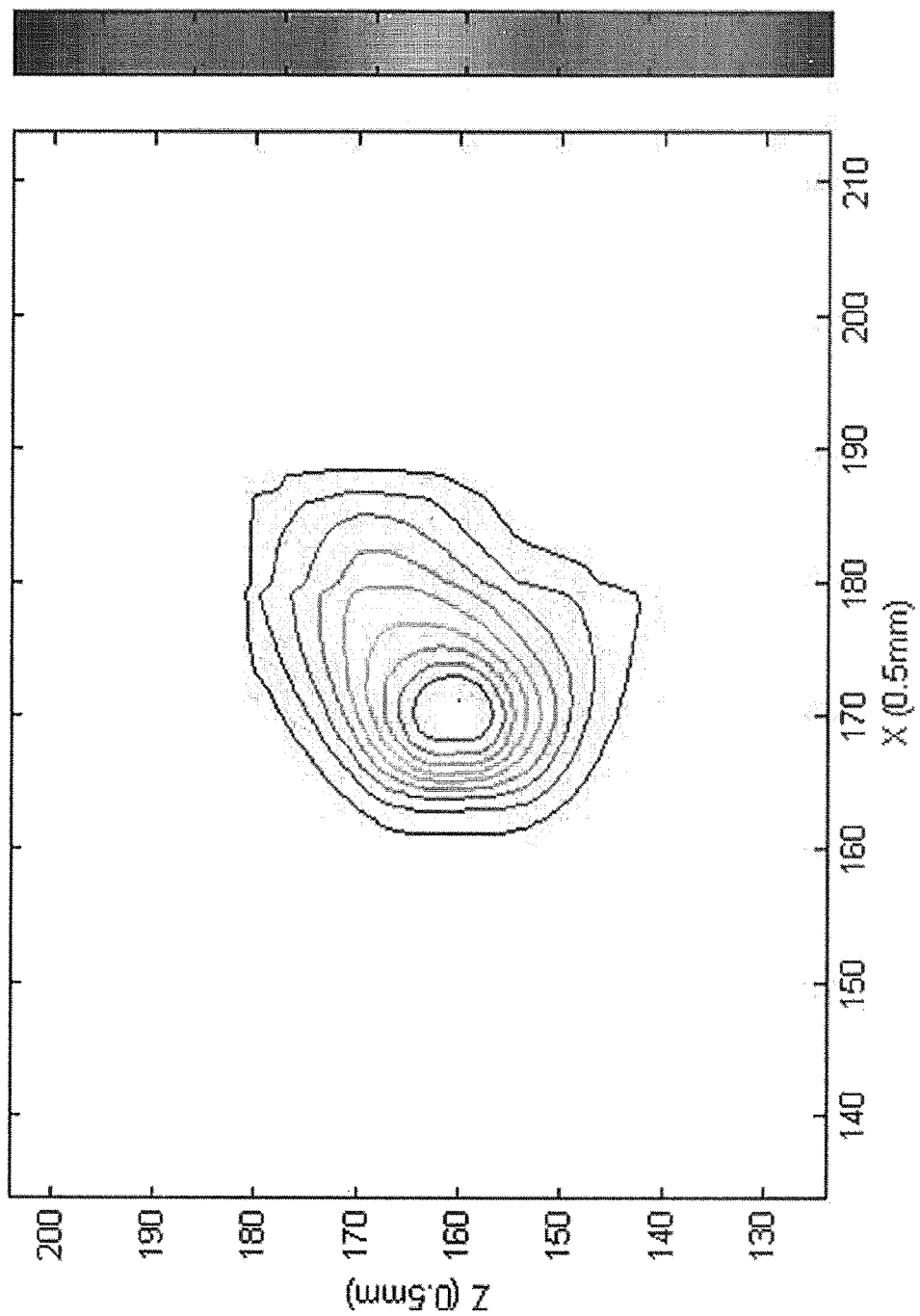

The goal is to have the tumor receive a 2100 cGy radiation dose. FIG. 20 shows the DVH comparison. FIGS. 21(a)-(c) and FIGS. 22(a)-(d) show the comparisons between dose profiles and between isodose distributions. FIGS. 21(a)-(c) illustrate the dose profiles with the DPP plan shown by line 18 and the Gamma Knife® plan shown by line 20. Specifically, FIG. 21(a) illustrates the dose provides along the X direction;

FIG. 21(b) illustrates the dose profiles along the Y direction; and FIG. 21(c) illustrates the does profiles along the Z direction. FIG. 22(a) illustrates the isodose distribution of the DPP plan in the XY plane; FIG. 22(b) illustrates the isodose distributions of the Gamma Knife® plan in the XY plane; FIG. 22(c) illustrates the isodose distributions of the DPP plan in the XZ plane; FIG. 22(d) illustrates the isodose distributions of the Gamma Knife® plan in the XZ plane. The plots shown contains isodose lines from 10% to 100% with 10% steps. The DPP plan is better than the Gamma Knife® plan. This is because, in the DPP plan, the target receives a higher dose and critical structures receive a lower dose than with the Gamma Knife® plan.

Figure 23:
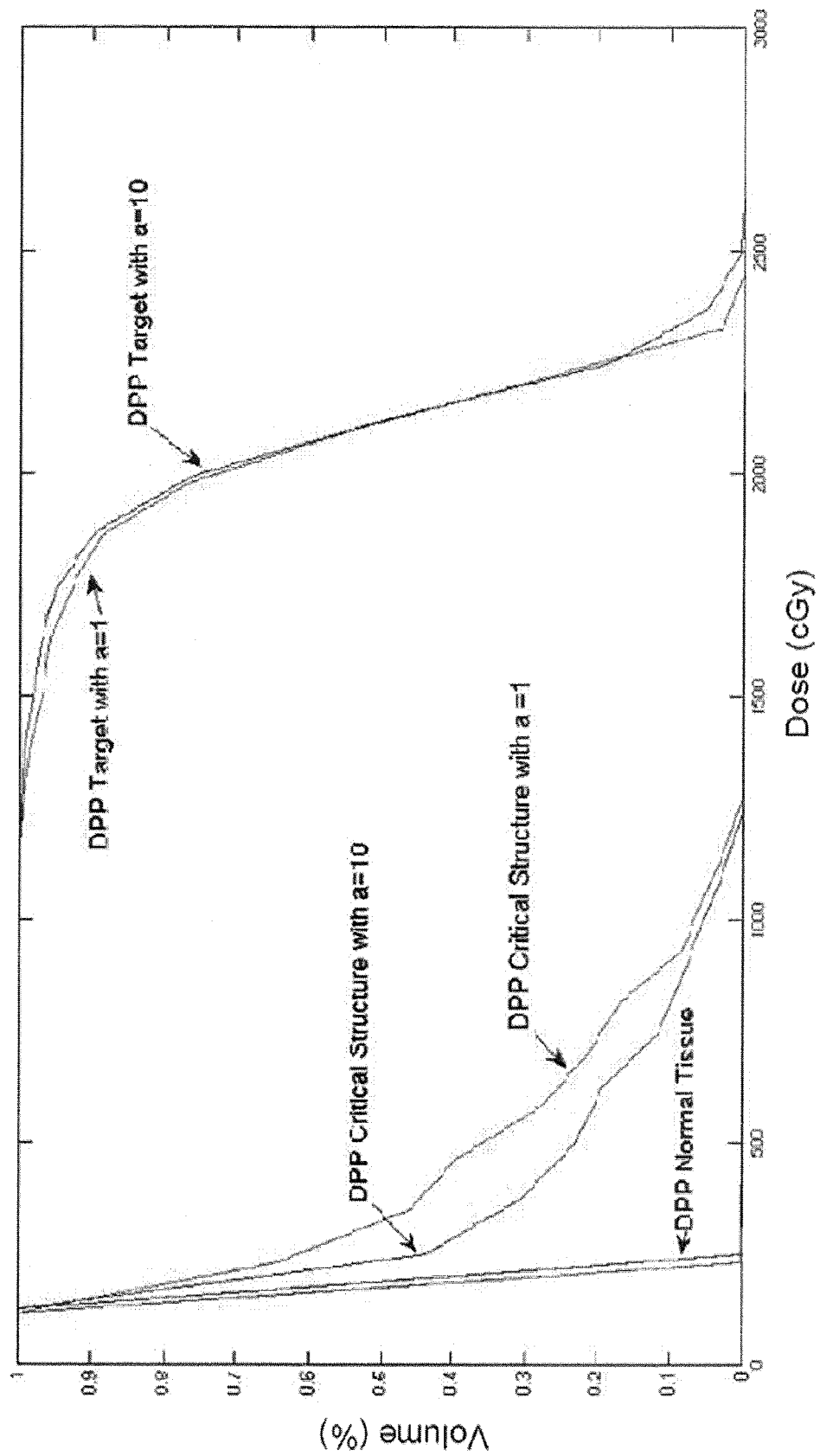
FIG. 23 illustrates comparisons of DVH according to the present invention.
Figure 24A:
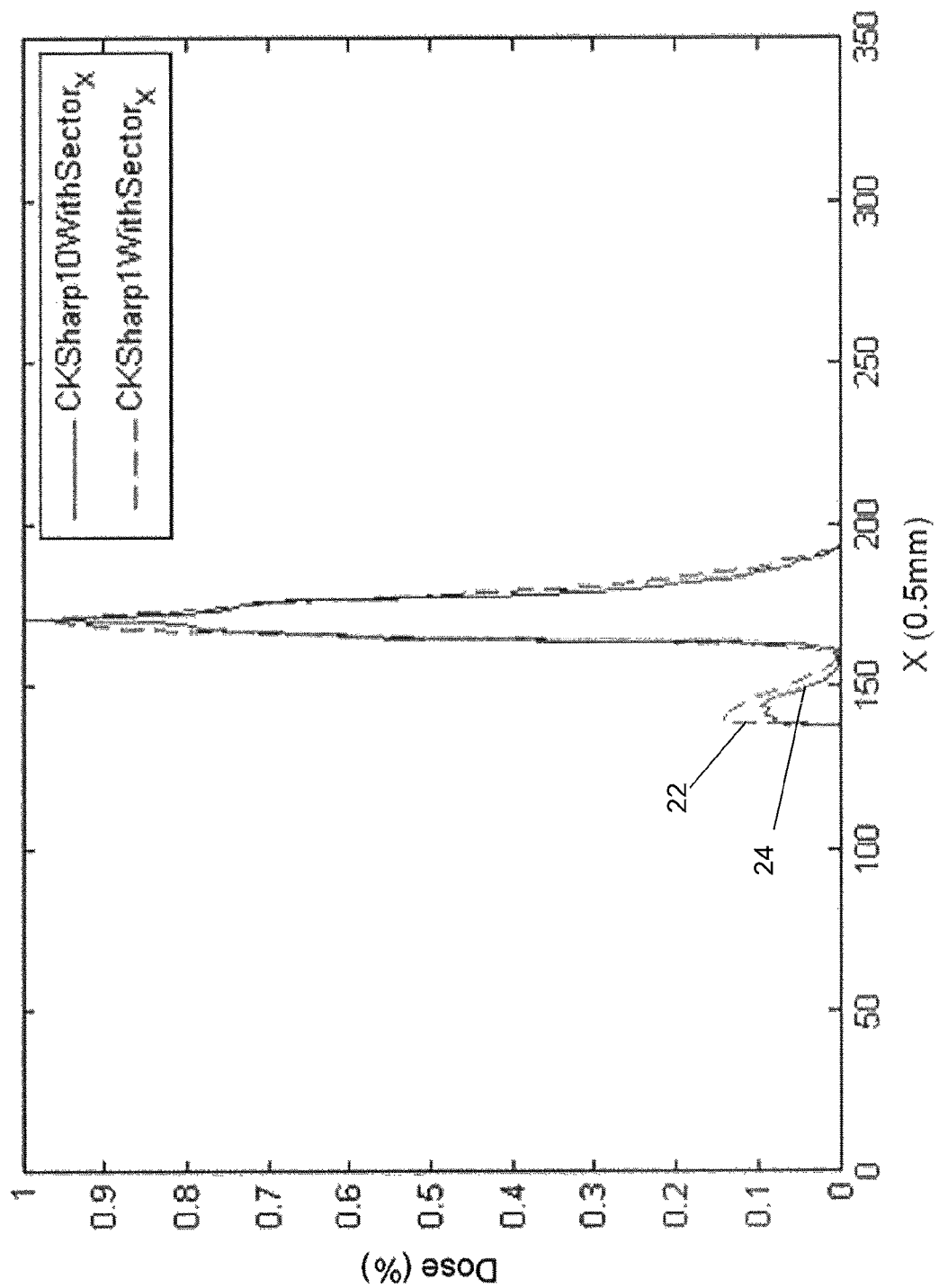
FIGS. 24(a)-(c) illustrate dose profile comparisons between various DPP plans according to the present invention.
Figure 24B:
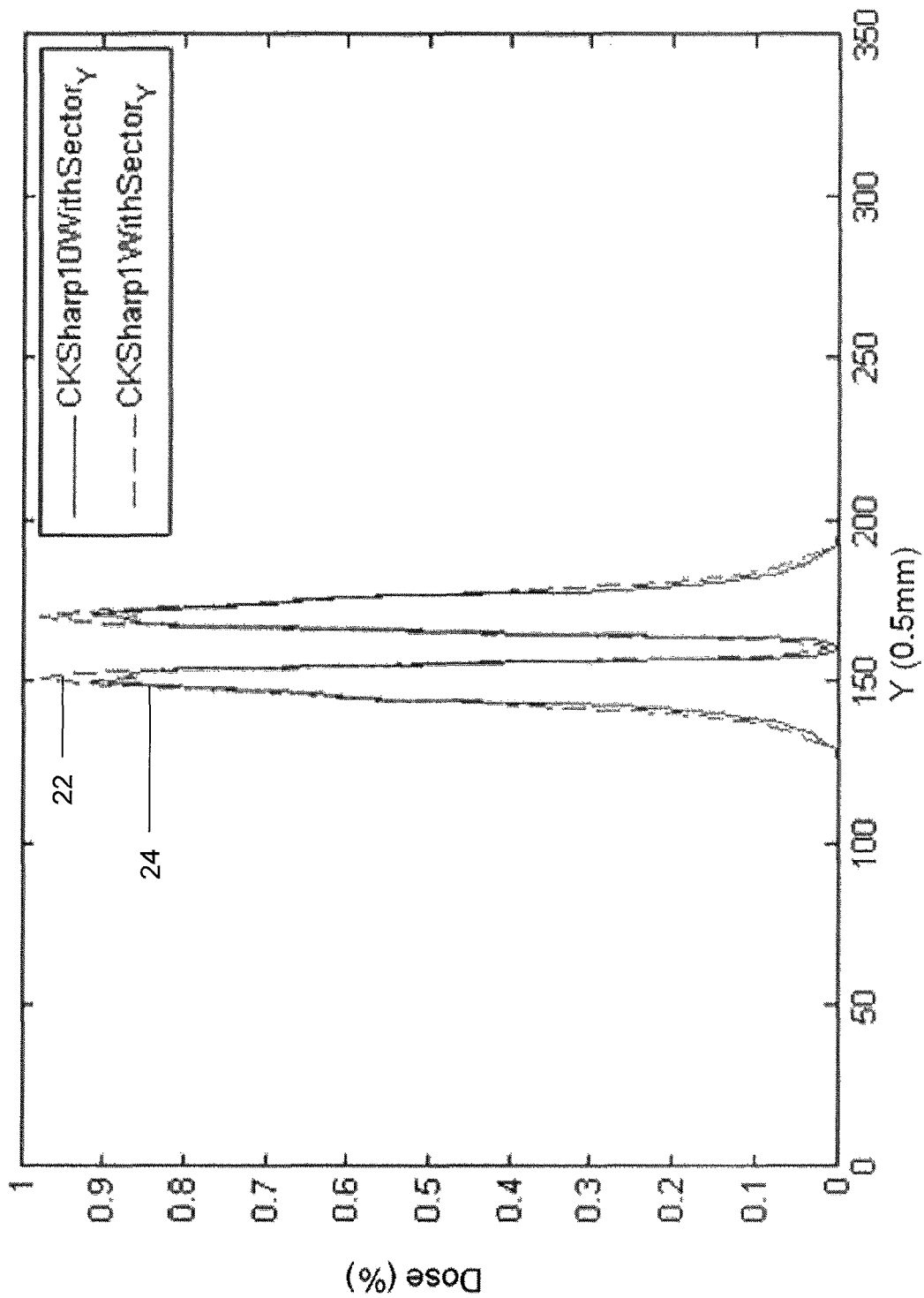
Figure 24C:
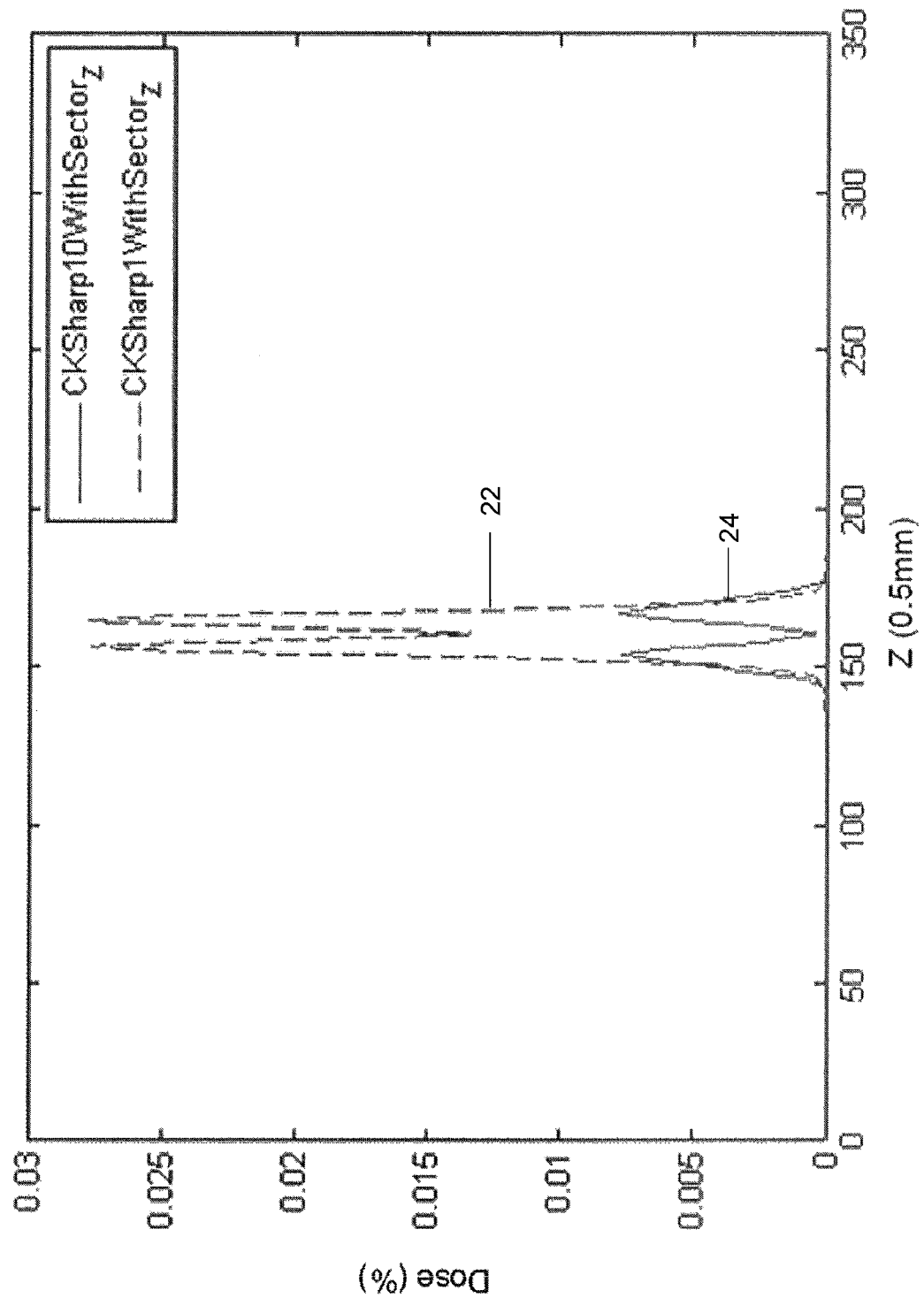
Figure 25A:
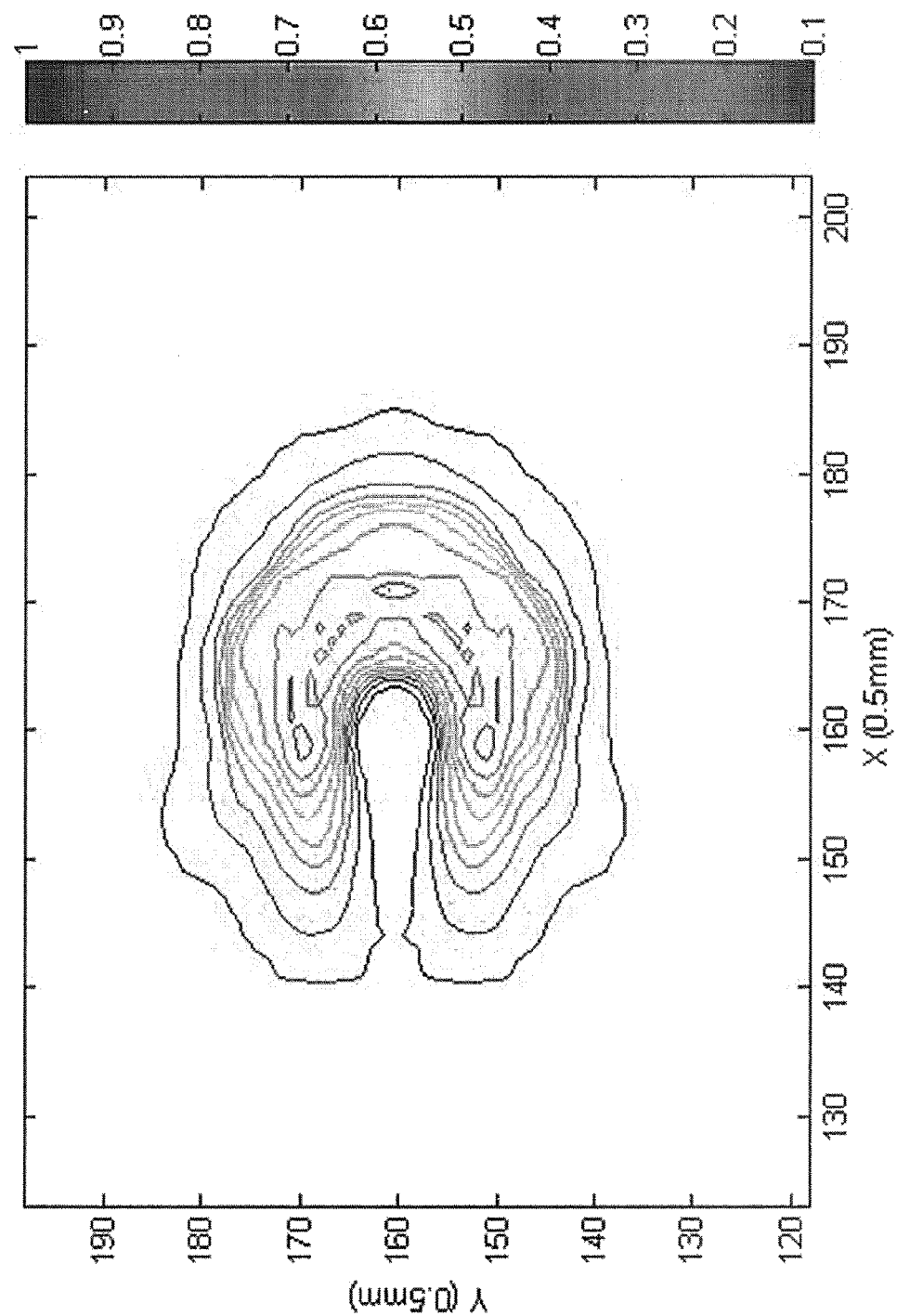
FIG. 25(a)-(d) illustrate isodose comparisons between various DPP plans according to the present invention.
Figure 25B:
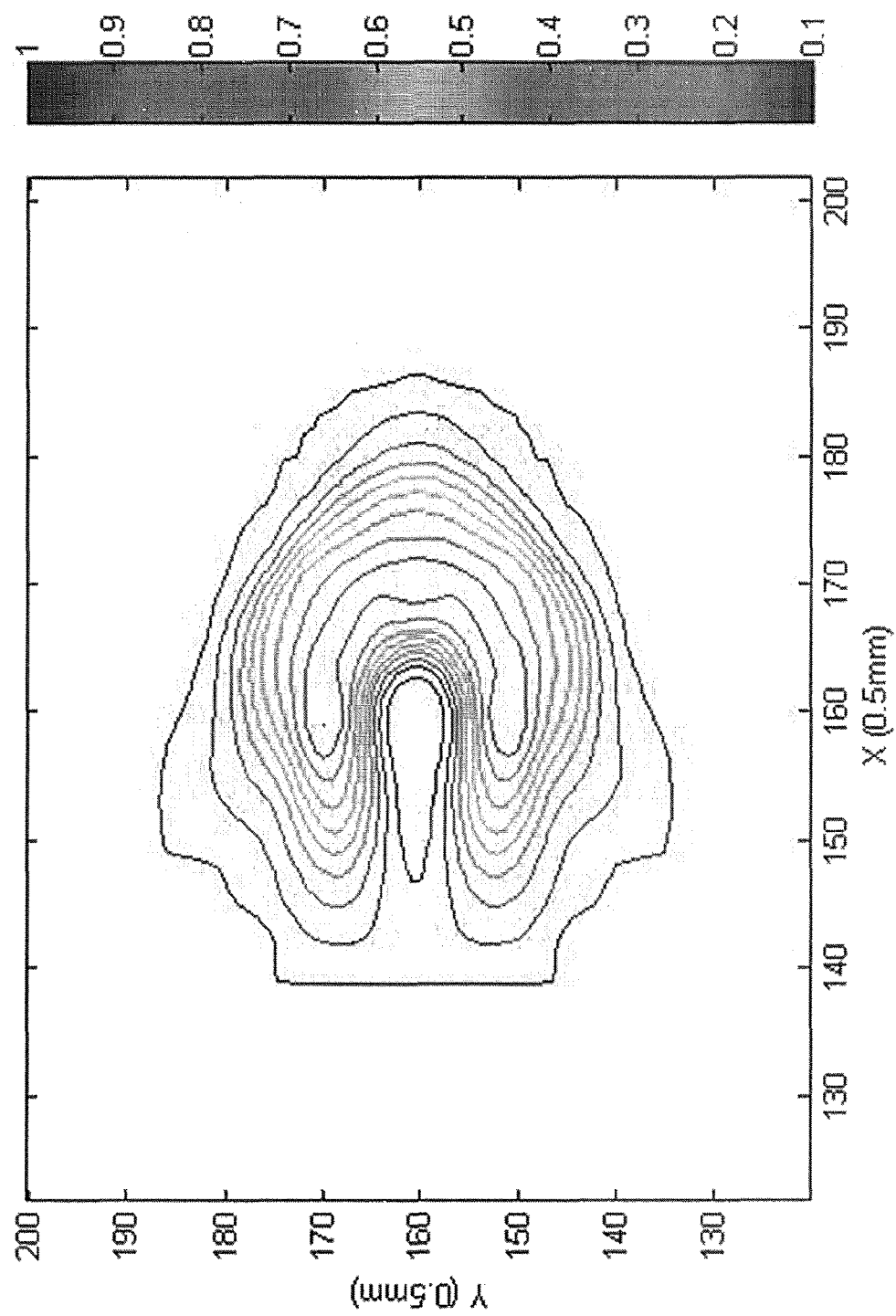
Figure 25C:
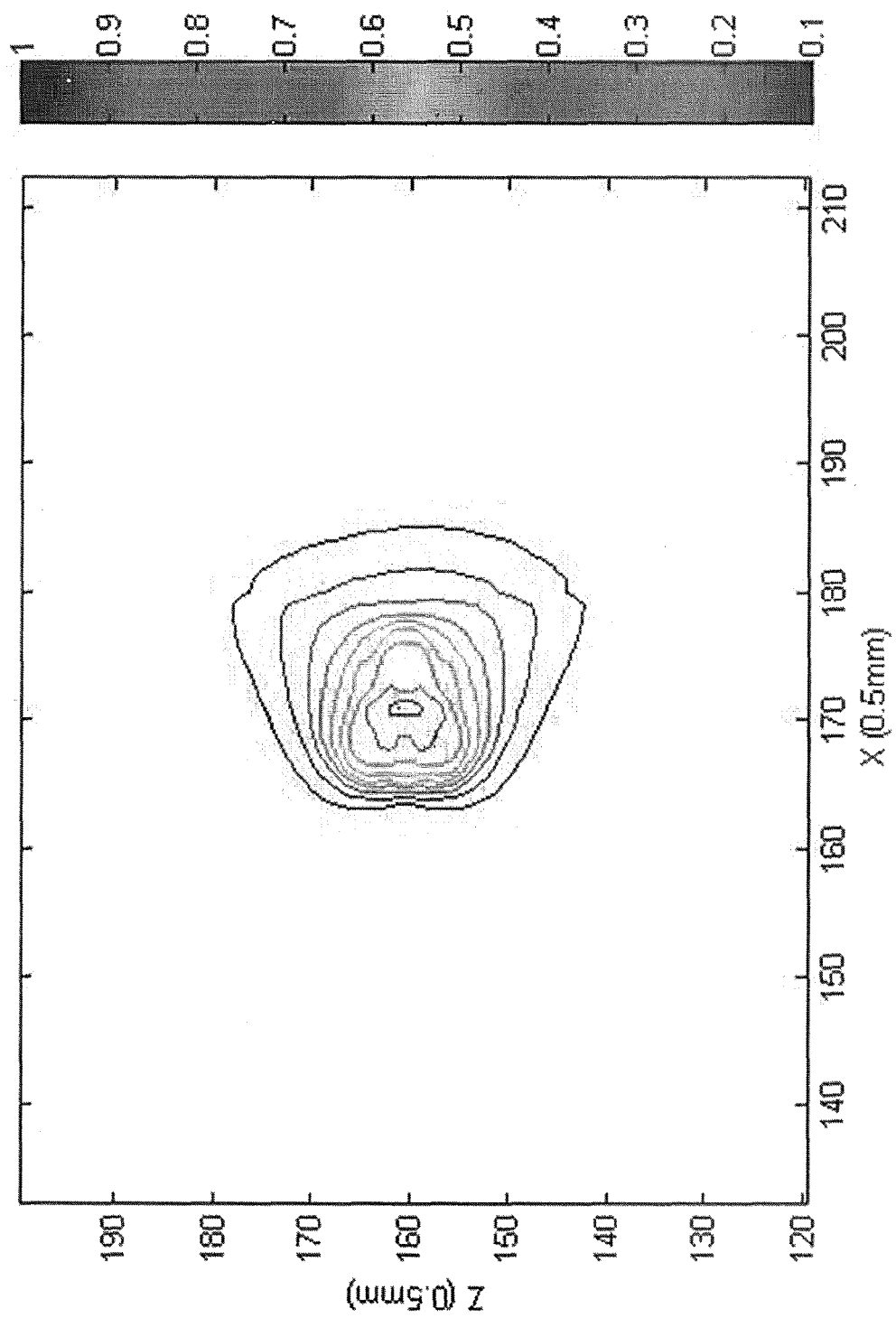
Figure 25D:
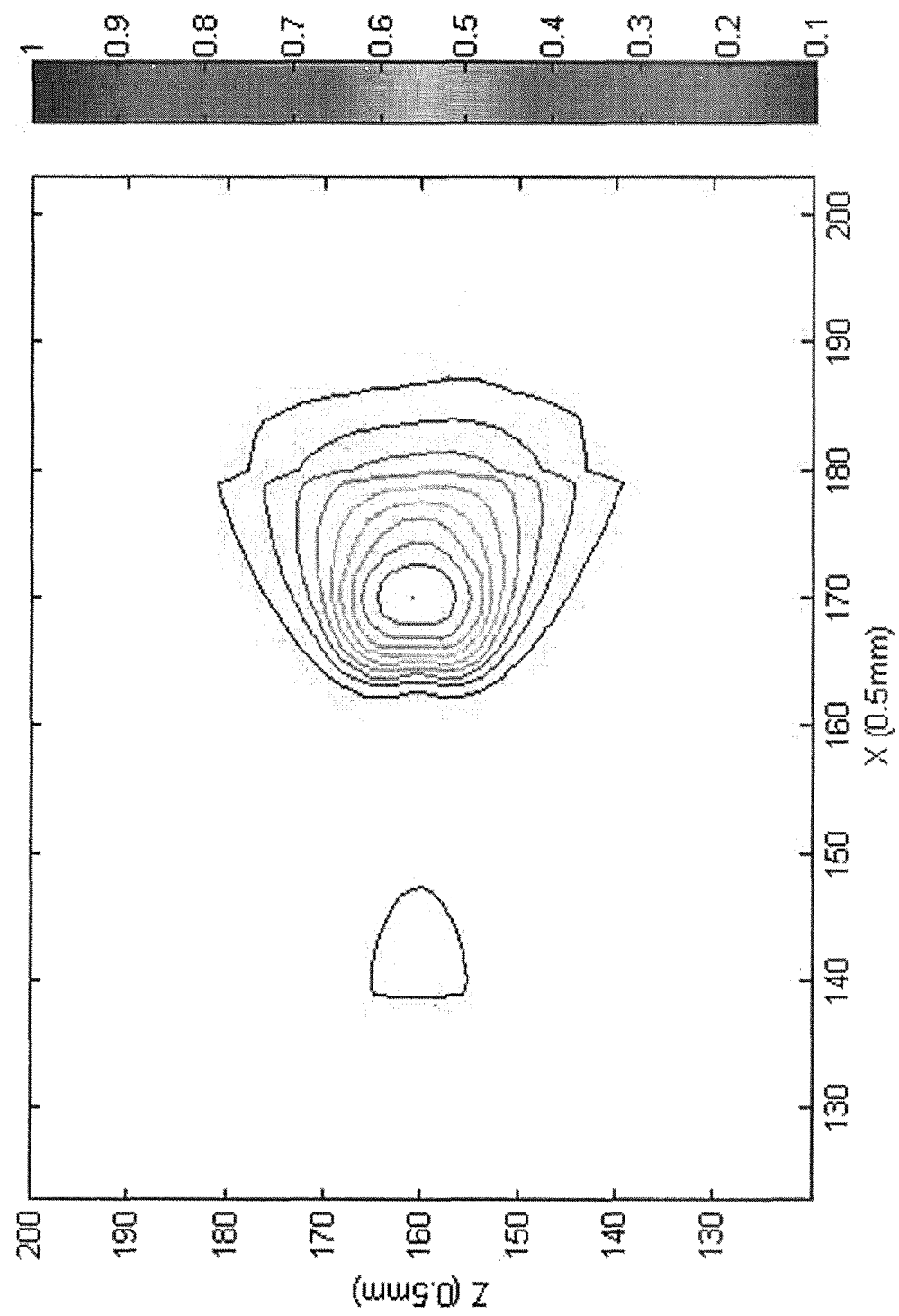

Since the DPP approach uses a single cone beam to dynamically treat a target, it is possible to modify the beam profiles of the cone beam (e.g., beam sharpness) to further improve the dose gradient. To demonstrate this, two sets of DPP kernels are created with two different ERFC sharpness parameters a=1 and a=10. These kernels are used in the Dynamic Gamma Knife® Radiosurgery Treatment Planning System. The goal is to let the tumor receive a 2100 cGy dose. FIG. 23 shows the DVH comparison. FIGS. 24(a)-(c) illustrates the dose profiles with the DPP plan shown by line 22 and the Gamma Knife® plan shown by line 22. FIGS. 25(a)-(d) show the comparisons between dose profiles and isodose distributions. FIG. 24(a) illustrates dose profiles along the X direction; FIG. 24(b) illustrates dose profiles along the Y direction; and FIG. 24(c) illustrates dose profiles along the Z direction. FIG. 25(a) illustrates the isodose distributions of the DPP plan with a=10 in the XY plane; FIG. 25(b) illustrates the isodose distributions of the DPP plan with a=1 in the XY plane; FIG. 25(c) illustrates the isodose distribution of the DPP plan with a=10 in the XZ plane; and FIG. 25(d) illustrates the isodose distribution of the DPP plan with a=1 in the XZ plane. The plots shown contain isodose lines from 10% to 100% with 10% steps. As the ERFC sharpness parameter increases, the target receives a higher dose and critical structures receive a lower dose, which results in an improved treatment plan using the present invention as compared to conventional treatment plans. In reviewing the profile comparisons shown in FIGS. 24(a)-(c), it can be seen that the DPP plan with a=10 has a lower dose at a low dose region than a DPP plan with a=1. This means the critical structure receives a lower dose as the ERFC parameter increases.

CyberKnife® robotic radiosurgery may be used to implement dynamic photon painting according to the present invention. In one embodiment, it is contemplated that the computational challenge of optimizing thousands of beams can be solved using one or more of cloud computing, GPU technologies, vector instructions, and multithreading.

Dynamic photon painting for radiation therapy and radiosurgery may be used in place of proton therapy and Gamma Knife® radiosurgeries.

Figure 26:
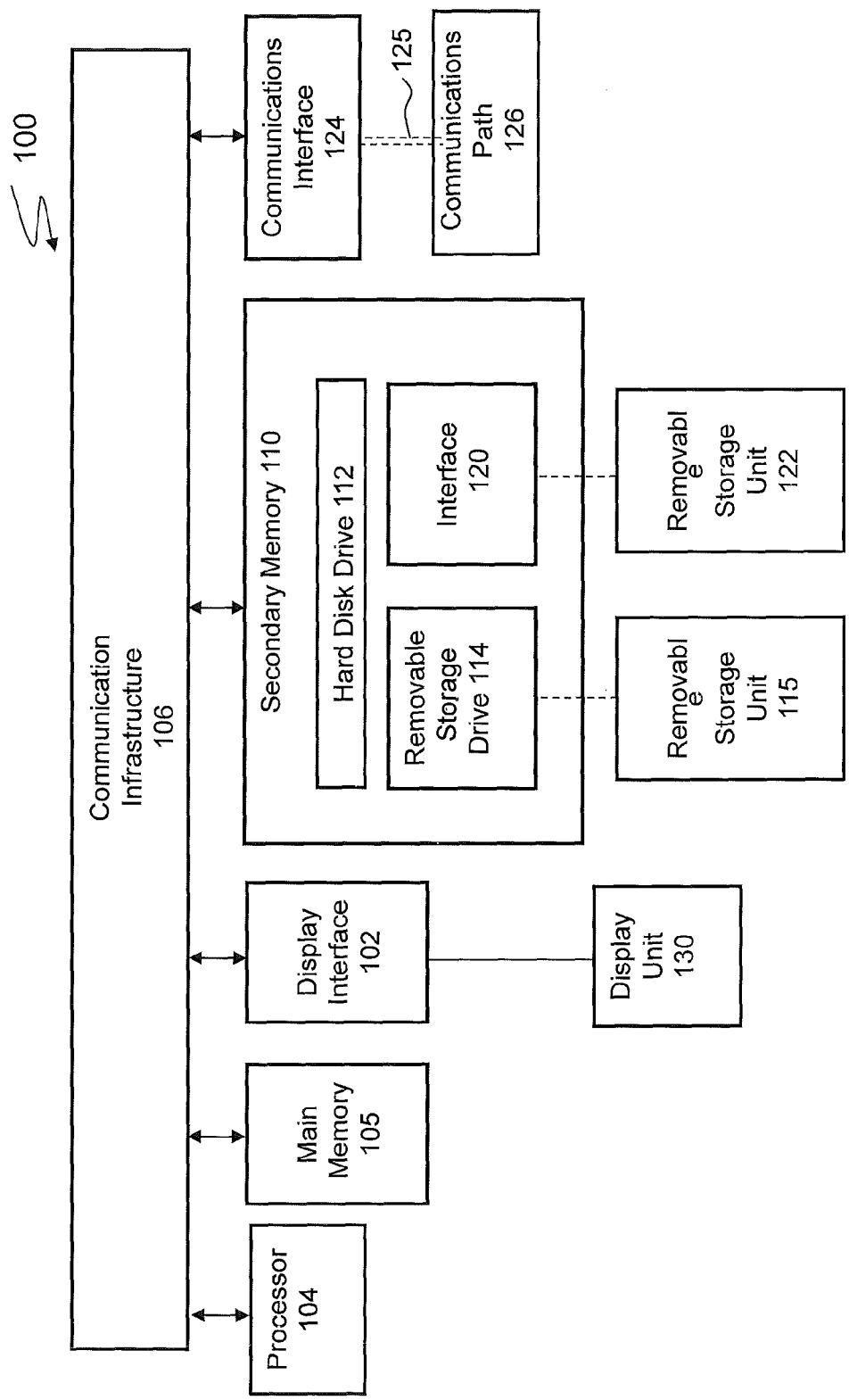
FIG. 26 illustrates an exemplary computer system, or network architecture, that may be used to implement the methods according to the present invention.

In addition to CyberKnife® robotic radiosurgery, FIG. 26 illustrates an exemplary computer system 100, or network architecture, that may be used to implement certain methods according to the present invention. One or more computer systems 100 may carry out the methods presented herein as computer code. One or more processors, such as processor 104, which may be a special purpose or a general-purpose digital signal processor, is connected to a communications infrastructure 106 such as a bus or network. Computer system 100 may further include a display interface 102, also connected to communications infrastructure 106, which forwards information such as graphics, text, and data, from the communication infrastructure 106 or from a frame buffer (not shown) to display unit 130. Computer system 100 also includes a main memory 105, for example random access memory (RAM), read-only memory (ROM), mass storage device, or any combination thereof. Computer system 100 may also include a secondary memory 110 such as a hard disk drive 112, a removable storage drive 114, an interface 120, or any combination thereof. Computer system 100 may also include a communications interface 124, for example, a modem, a network interface (such as an Ethernet card), a communications port, a PCMCIA slot and card, wired or wireless systems, etc.

It is contemplated that the main memory 105, secondary memory 110, communications interface 124, or a combination thereof function as a computer usable storage medium, otherwise referred to as a computer readable storage medium, to store and/or access computer software and/or instructions.

Removable storage drive 114 reads from and/or writes to a removable storage unit 115. Removable storage drive 114 and removable storage unit 115 may indicate, respectively, a floppy disk drive, magnetic tape drive, optical disk drive, and a floppy disk, magnetic tape, optical disk, to name a few.

In alternative embodiments, secondary memory 110 may include other similar means for allowing computer programs or other instructions to be loaded into the computer system 100, for example, an interface 120 and a removable storage unit 122. Removable storage units 122 and interfaces 120 allow software and instructions to be transferred from the removable storage unit 122 to the computer system 100 such as a program cartridge and cartridge interface (such as that found in video game devices), a removable memory chip (such as an EPROM, or PROM) and associated socket, etc.

Communications interface 124 allows software and instructions to be transferred between the computer system 100 and external devices. Software and instructions transferred by the communications interface 124 are typically in the form of signals 125 which may be electronic, electromagnetic, optical or other signals capable of being received by the communications interface 124. Signals 125 are provided to communications interface 124 via a communications path 126. Communications path 126 carries signals 125 and may be implemented using wire or cable, fiber optics, a phone line, a cellular phone link, a Radio Frequency ("RF") link or other communications channels.

Computer programs, also known as computer control logic, are stored in main memory 105 and/or secondary memory 110. Computer programs may also be received via communications interface 124. Computer programs, when executed, enable the computer system 100, particularly the processor 104, to implement the methods according to the present invention. The methods according to the present invention may be implemented using software stored in a computer program product and loaded into the computer system 100 using removable storage drive 114, hard drive 112 or communications interface 124. The software and/or computer system 100 described herein may perform any one of, or any combination of, the steps of any of the methods presented herein. It is also contemplated that the methods according to the present invention may be performed automatically, or may be invoked by some form of manual intervention.

The invention is also directed to computer products, otherwise referred to as computer program products, to provide software to the computer system 100. Computer products store software on any computer useable medium. Such software, when executed, implements the methods according to the present invention. Embodiments of the invention employ any computer useable medium, known now or in the future. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, optical storage devices, Micro-Electro-Mechanical Systems ("MEMS"), nanotechnological storage device, etc.), and communication mediums (e.g., wired and wireless communications networks, local area networks, wide area networks, intranets, etc.). It is to be appreciated that the embodiments described herein can be implemented using software, hardware, firmware, or combinations thereof.

The computer system 100, or network architecture, of FIG. 26 is provided only for purposes of illustration, such that the present invention is not limited to this specific embodiment. It is appreciated that a person skilled in the relevant art knows how to program and implement the invention using any computer system or network architecture.

The invention is also directed to computer products (also called computer program products) comprising software stored on any computer useable medium. Such software, when executed, at least in part, in one or more data processing devices, causes the data processing device(s) to operate as described herein. Embodiments of the invention employ any computer useable or readable medium, known now or in the future. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, optical storage devices, MEMS, nanotechnological storage device, etc.), and communication mediums (e.g., wired and wireless communications networks, local area networks, wide area networks, intranets, etc.). It is to be appreciated that the embodiments described herein can be implemented using software, hardware, firmware, or combinations thereof.

While the disclosure is susceptible to various modifications and alternative forms, specific exemplary embodiments thereof have been shown by way of example in the drawings and have herein been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

The invention claimed is:

1. A computer system method for radiosurgery, the method comprising the steps of:
    identifying a target;
    creating a plurality of dose kernels by convolving a plurality of radiation beams along preset three-dimensional trajectories, wherein said creating step further comprises the step of determining one or more beam characteristics of each radiation beam that increase a dose falloff rate from high dose regions inside the target to low dose regions nearby the target;
    calculating a route of each of the dose kernels, wherein the route covers the target;
    obtaining an individual trajectory for each of the dose kernels by de-convolving each of the dose kernels along the route;
    connecting the individual trajectory for each of the dose kernels that increase the dose falloff rate to obtain a dynamic trajectory;
    moving a radiation beam source along the dynamic trajectory; and
    applying to the target a radiation beam from the radiation beam source to irradiate the target.

2. The computer system method for radiosurgery according to claim 1, wherein the radiation beam is a cone radiation beam.

3. The computer system method for radiosurgery according to claim 1, wherein the radiation beam source rotates around a center of the target.

4. The computer system method for radiosurgery according to claim 1, wherein the one or more beam characteristics include a beam shape, a beam profile and a beam trajectory.

5. The computer system method for radiosurgery according to claim 1, further comprising the step of creating a library of the plurality of dose kernels.

6. The computer system method for radiosurgery according to claim 5, wherein the library comprises one or more different beam shapes, one or more different beam profiles and one or more different beam trajectories.

7. The computer system method for radiosurgery according to claim 1, wherein the dynamic trajectory is described by a latitude angular range parameter, a longitude angular range parameter, and a source to axis distance parameter.

8. The computer system method for radiosurgery according to claim 1, wherein the radiation beam source includes beam profiles and cross sections that can change or be any predetermined shape.

9. The computer system method for radiosurgery according to claim 1, wherein at least one selected from the group of speed, direction and dose rate of the radiation beam dynamically varies during said applying step.

10. The computer system method for radiosurgery according to claim 1, wherein the dynamic trajectory is a helical trajectory.

11. The computer system method for radiosurgery according to claim 1, wherein the dynamic trajectory is a predetermined trajectory.

12. The computer system method for radiosurgery according to claim 1, wherein the target is a brain tumor.

13. The computer system method for radiosurgery according to claim 1, wherein the radiation beam includes photons.

* * * * *